United States Patent
Tischfield et al.

(12)

(10) Patent No.: US 6,232,524 B1
(45) Date of Patent: May 15, 2001

(54) LIVE MOUSE MUTAGENESIS SYSTEMS FOR TESTING MUTAGENIC AGENTS IN VIVO

(76) Inventors: Jay A. Tischfield, 604 Allison Rd., Piscataway, NJ (US) 08854-8082; Peter J. Stambrook, 1000 Advondale Ave., Cincinnati, OH (US) 45229

( * ) Notice: Subject to any disclaimer, the term of this patent is extended or adjusted under 35 U.S.C. 154(b) by 0 days.

(21) Appl. No.: 09/363,600

(22) Filed: Jul. 29, 1999

Related U.S. Application Data

(63) Continuation of application No. 08/461,607, filed on Jun. 5, 1995, now Pat. No. 6,054,633, which is a continuation of application No. 08/379,105, filed on Jan. 27, 1995, now abandoned, which is a continuation of application No. 07/874,974, filed on Apr. 27, 1992, now abandoned.

(51) Int. Cl.[7] .......................... A01K 67/027; A01K 69/00
(52) U.S. Cl. .................................... 800/18; 800/3
(58) Field of Search ................... 800/3, 14, 18, 800/25

(56) References Cited

U.S. PATENT DOCUMENTS 6,054,633 * 4/2000 Tischfield et al. .................... 800/18

* cited by examiner

*Primary Examiner*—Deborah Crouch
(74) *Attorney, Agent, or Firm*—Jenkens & Gilchrist, A Professional Corporation

(57) ABSTRACT

Novel transgenic nonhuman animals for detecting and characterizing mutations in vivo are disclosed. When detecting reverse mutations, the transgenic nonhuman animal now afford the unique advantage of detecting and characterizing mutations in vivo without having to sacrifice the animals as required heretofore. Moreover, since the transgenic nonhuman animals do not need to be sacrificed, they provide the unique opportunity to correlate the incidence and location of tumors (carcinogenesis) with the incidence and location of mutagenesis. Also disclosed are novel constructs, cell lines and chimeric animals for producing the novel transgenic animals. Novel methods for detecting and characterizing the mutations in vivo and producing animals for use in accordance with the methods of the instant invention are disclosed.

1 Claim, 3 Drawing Sheets

LIVE MOUSE MUTAGENESIS SYSTEMS FOR TESTING MUTAGENIC AGENTS IN VIVO

This application is a continuation of prior application Ser. No. 08/461,607, filed on Jun. 5, 1995, U.S. Pat. No. 6,054,633 entitled Live Mouse Mutagenesis Systems for Testing Mutagentic Agens In Vivo, which was a continuation of application Ser. No. 08/379,105, filed on Jan. 27, 1995, now abandoned, which was a continuation of application Ser. No. 07/874,974, filed Apr. 27, 1992, now abandoned.

FIELD OF THE INVENTION

The present invention relates to novel transgenic animals for detecting mutagenic agents and characterizing the nature of the mutations thereby induced in vivo. The present invention further relates to novel constructs, cell lines and chimeric animals for producing the transgenic animals. The present invention further relates to novel methods for detecting and characterizing forward and reverse mutations in vivo.

BACKGROUND

The impact of environmental chemicals on human health has been clearly recognized and extensively reviewed. See, for example, Fishbein, L. pp. 329–363. In D. B. Walters, Ed. *Safe Handling of Chemical Carcinogens, Mutagens, Teratogens and Highly Toxic Substances.* Vol. I, Ann Arbor, Mich.: Ann Arbor Science (1980); and *Identifying and Estimating the Genetic Impact of Chemical Mutagens,* National Academy Press, Washington, D.C. (1983). There are more than 70,000 synthetic chemicals in current commercial use, including pharmaceuticals, food additives, industrial chemicals, and pesticides. *Identifying and Estimating the Genetic Impact of Chemical Mutagens,* National Academy Press, Washington, D.C. (1983) and Hollstein, M. et al.: *Mutat. Res.,* 65:133–226 (1979). About a quarter of these are believed to be produced in abundance, with additional new chemicals introduced at a rate of about 1,000 per year. These numbers represent an alarming statistic when one considers the strong correlation between somatic cell mutagenesis and carcinogenesis, and between germ cell mutagenesis and heritable disease. McCann, J. et al.: *Proc. Nat. Acad. Sci. USA,* 72:5135–5139 (1975). Exposure to many of these compounds is believed to pose a significant environmental health risk. In particular, somatic mutation, incurred as a consequence of exposure to environmental mutagens, is currently thought to produce an increased risk for the development of cancer.

Assessment of the mutagenicity of compounds or environments is extremely important for establishing a rational basis for reducing human exposure to those compounds that prove mutagenic. To this end, numerous short-term mutagenicity assays have been devised. See, for example, Waters, M. D. pp. 449–467. In A. W. Hsie, P. J. O'Neil and U. K. McElheny, Eds. *Mammalian Cell Mutagenesis: The Maturation of Test Systems.* Banbury Report 2. New York: Cold Spring Harbor Laboratory (1979). For example, the Salmonella/liver microsome test which was pioneered by Ames and his colleagues, has the ability to detect some mutagens. See, for example, McCann, J. et al.: *Proc. Nat. Acad. Sci. USA,* 72:5135–5139 (1975), Waters, M. D. pp. 449–467. In A. W. Hsie, P. J. O'Neil and U. K. McElheny, Eds. *Mammalian Cell Mutagenesis: The Maturation of Test Systems.* Banbury Report 2. New York: Cold Spring Harbor Laboratory (1979), and Ames, B. N. et al.: *Science,* 176:47–48 (1972); Maron, D. M. and Ames, B. N.: *Mut. Res.,* 113:173–215 (1983); Ashby, J. pp. 1–33. Mutagenicity: New Horizons in Toxicology. Ed. J. A. Heddle, N.Y., Academic Press (1982); and McCann, J. and Ames, B. N.: *Proc. Nat. Acad. Sci. USA,* 73:950–954 (1976). In addition to the Ames bacterial test, there are short-term tests that utilize fungi, cultured mammalian cells, Drosophila and mice. While many of these short-term tests measure mutation at one or more genetic loci, others exploit end-point criteria such as clastogenesis, aneuploidy, DNA repair, micronucleus production, mitotic recombination, sister chromatid exchange or the formation of DNA adducts.

Unfortunately, the short-term mutagenicity assays are not without certain limitations and drawbacks. One major problem with the Ames bacterial test is believed to be its inability to recognize a significant number of known carcinogens. Another major problem with the existing short-term mutagenicity assays stems from tissue-specific differences in the ability to metabolize various chemicals. See, for example, *Identifying and Estimating the Genetic Impact of Chemical Mutagens,* National Academy Press, Washington, D.C. (1983). For instance, some mutagens are direct-acting and are active in their parental (nonmetabolized) forms; however, most require metabolic conversion by one or more P450 enzymatic activities. There are numerous P450 activities, which constitute a large subset of monooxygenases, and many appear to have overlapping substrate specificities. See, for example, *Identifying and Estimating the Genetic Impact of Chemical Mutagens,* National Academy Press, Washington, D.C. (1983); and Lu, A. Y. H. and Est, S. B.: *Pharmacol. Rev.,* 31:277–295. The genes and cDNAs for some have been cloned and characterized. See, for instance, Gonzalez, F. J. et al.: *Mutation Research,* 247:113–127 (1991). While subcellular fractions, freshly prepared cells or long-term cell cultures may retain several P450 activities, many are lost. See, for example, *Identifying and Estimating the Genetic Impact of Chemical Mutagens,* National Academy Press, Washington, D.C. (1983). Because of these problems, current in vitro mutagenicity assays are believed to be unable to precisely reproduce the spectrum of complex metabolic activities found in intact animals, tissues or differentiated cells and, as a consequence, rely upon compromises. Also, data from in vitro mutagenicity assays are difficult to correlate with carcinogenic potency in whole animals as measured by the incidence of tumors and the required dose of carcinogen.

In addition to these in vitro short-term mutagenicity assays, there are, for example, two in vivo assays that rely upon transgenic mice as mutagen detectors, which are marketed by Strategene and Hazelton. Both have adopted a similar approach. Their basic strategy has been to incorporate a bacterial reporter gene (lacZ or lacI) into a bacteriophage lambda, and to render mice transgenic for these constructs by pronuclear injection. The recombinant lambda prophage DNA integrates into the host genome as a tandem array, and can be rescued as particles infectious for *E. coli* by incubation with an extract that provides lambda phage capsid and tail proteins. In carrying out these in vivo assays, the mice are exposed to mutagens/carcinogens, and two or three days later (or longer) they are sacrificed. Individual organs (e.g. brain, liver, kidney, etc.) are recovered and DNA is extracted. The purified DNA is incubated with the lambda phage packaging extract, and infectious particles containing the packaged reporter gene are added to *E. coli.* If the lacZ gene is the reporter gene, wild-type lacZ will produce blue colored plaques when stained for beta-galactosidase activity.

Conversely, mutant lacZ will produce colorless plaques. When lacI is used as the reporter gene, the color scheme is reversed. Wild-type lacI will produce colorless plaques and mutant lacI will produce blue plaques in the appropriate *E. coli* host. By counting plaques with mutant reporter genes, both groups, Strategene and Hazelton, estimate the relative mutagenicity of each compound for different organs.

Like the in vitro short-term mutagenic assays, these two in vivo assays are not without drawbacks. For example, it is difficult to separate mutation frequency from contributions by mitotic activity. In other words, if a cell with a mutant reporter gene is stimulated to proliferate, one would observe multiple mutant plaques as a consequence of a single mutagenic event. As a further drawback, the animals must be sacrificed and dissected for analysis, and their DNAs must be extracted and packaged before infecting the reporter *E. coli*. This requirement of dissection restricts the inherent power of the system to resolve which cell types or specific tissues are susceptible to mutagenesis. As a further disadvantage, the need to destroy the animals for detection of mutagenesis obviates the ability to follow the fates of mutagenized cells through the life cycle of the animals. Moreover, the possibility of correlating mutagenesis with carcinogenesis in the same animal is obviated.

In yet another drawback, the above in vivo transgenic systems rely upon the mutagenesis of a bacterial gene within a bacteriophage context. Bacterial genes are different from typical mammalian genes in terms of specific nucleotide content, codon usage, lack of introns and consensus splice sequences and other features. Moreover, because these transgenic systems rely upon the introduction of exogenous bacterial genes, the exogenous genes may interfere with the local chromatin structure within recipient chromosomes. Consequently, such interference may adversely impact upon the reliability of these in vivo transgenic systems. Thus, important and frequent types of mutations in eukaryote cells, such as those that destroy proper mRNA splicing, will not be detected by the above system. Further, the mutagenesis of the bacterial gene is subject to the effects (position effects) of the particular mammalian DNA context or chromosome site within which it resides. For example, whether or not the adjacent mammalian DNA is transcriptionally active or associated with heterochromatin could affect the mutagenesis of the inserted bacterial gene. Furthermore, in different, independently produced animals, utilizing the same or different bacterial genes, each introduced gene (transgene) is likely to be located within a different region of the host genome. Thus, different introduced genes will be subject to different position effects and their mutagenesis cannot be easily compared. Finally, the transgenic animals must be dissected, the DNA must be extracted, DNA must be packaged, and DNA must be sequenced to determine the molecular nature of mutagenesis. These requirements severely limit the number of mutagenic events that can be characterized. Moreover, the requirements render these in vivo systems incapable of identifying the specific cell types that undergo mutation.

Consequently, there clearly is a need for an in vivo mutation assay which does not require the animals to be sacrificed in order to detect the mutations of interest, which does not require a large number of animals to be used in order to detect a large number of mutagenic events, which permits the fate of mutant cells and their progeny to be followed during the life cycle of the animals utilized, which has the ability to quantitate the mutagenesis of the endogenous genes, which has the ability to quickly establish tissue specific susceptibility to mutation after exposure to a mutagen, and which has the ability to characterize the mechanisms of mutation without having to sequence the DNA.

SUMMARY OF THE INVENTION

In brief, the present invention alleviates certain of the above-mentioned problems and shortcomings of the present state of the art through the discovery of novel live model mutagenesis systems for rapidly detecting mutagenic agents in vivo. The live model systems of the instant invention will not only identify agents which are mutagenic and potentially carcinogenic, but will also reveal or characterize the type of mutations, such as base substitutions and frame shifts, thereby induced. The live model mutagenesis systems of the instant invention are comprised of genetically engineered nonhuman animals (transgenic nonhuman animals), such as mice, that include as part of their genetic material, exogenous reporter genes, such as an APRT gene, having known mutations. In accordance with the instant invention, animals, such as mammals, fish and birds, may be used to form the live model systems for the detection of natural or synthetic mutagens and potential carcinogens. Assays including transgenic nonhuman animals are provided by the present invention for identifying mutagenic agents in vivo and for characterizing the molecular nature of the mutations induced thereby.

The live model systems of the instant invention are uniquely designed to test for mutagenic and potentially carcinogenic agents by detecting either forward mutations in heterozygous or hemizygous functional reporter genes, or reverse mutations in mutant reporter genes, preferably having known mutations. By "forward mutation(s)," it is meant herein to refer to the inactivation of the wild type target reporter gene. By "reverse mutation(s)," it refers herein to the reversion of a mutant gene to a gene which encodes a functional product. It should be understood to those versed in this art that while it is preferable to perform the reverse mutation with the mutant reporter gene in its natural location, the present invention also contemplates performing the reverse mutation with the mutant reporter gene in an ectopic location.

By the term "reporter gene(s)," it is used herein in a broad sense and is meant to define any gene or portion of a sequence that encodes a functional enzyme or product which binds a ligand or catalyzes the metabolism of a substrate (molecule) to a form which, when metabolized to the changed form, is selectively retained in a cell, such as those genes or sequences which encode for the salvage pathway enzymes. For example, the $APRT^+$ gene codes for functional adenine phosphoribosyltransferase which metabolizes adenine (an uncharged molecule) to adenylate (a charged molecule) which cannot exit cells. Examples of reporter genes which are contemplated by the instant invention include adenine phosphoribosyltransferase (aprt), hypoxanthine phosphoribosyltransferase (hprt), thymidine kinase (tk) and the like.

The assays of the instant invention uniquely rely upon certain biochemical reactions which take place in virtually every cell of an animal. More particularly, the assays of the present invention are premised upon the realization that certain functional enzymes or products encoded by the reporter genes catalyze intracellularly the transfer of a ribose phosphate group to substrates like purines (adenine, guanine or hypoxanthine) or a phosphate group to nucleosides (thymidine) to form nucleotides. For example, in the case of a "reverse mutation," the reversion of a mutated reporter gene, such as APRT⁻, endows the cell or group of cells with the reverted gene, e.g., reverted from APRT⁻ genotype to APRT⁺ genotype, with the genetic ability to produce a functional product which can metabolize a substrate such as adenine or an analog thereof to adenylate or a derivative thereof. When the substrate is in an unmetabolized form, such as adenine, the membrane of the APRT⁻ cells is permeable to it, and thus the adenine cannot accumulate in those cells. In APRT⁺ cells with functional APRT enzyme, however, the substrate is metabolized to contain a ribose-phosphate and is unable to exit the cells. The metabolized product is selectively retained within the cells and incorporated into the nucleic acids of those cells. Thus, when the substrate to be administered to the transgenic animals following exposure to a mutagen is labeled or tagged in accordance with the present invention, those cells that have undergone a reverse mutation within the mutated reporter genes are uniquely marked for subsequent detection and/or imaging.

Accordingly, when transgenic nonhuman animals having mutated reporter genes are produced in accordance with the instant invention, the above-described biochemical reactions cannot take place unless the mutated reporter genes first undergoes a mutagenic event to revert to the wild type gene or to a functional gene, i.e., a "reverse mutation," such as from APRT⁻ genotype to APRT⁺ genotype. Consequently, prior to exposing the transgenic nonhuman animals of the instant invention to mutagens, their cells cannot express the functional enzymes or products responsible for metabolizing the substrates to the phosphorylated forms resulting in the elimination of the unmetabolized substrates from the transgenics. However, after exposing the transgenic nonhuman animals of the present invention to a selected mutagen to thereby induce the mutated reporter genes to undergo mutation to the wild or functional type, i.e., "reverse mutation," the reverted cells are now capable of expressing the appropriate functional enzymes to catalyze the biochemical reactions. Thus, when labeled or tagged substrates, e.g., labeled purines, pyrimidines or analogs thereof, are administered to the transgenic nonhuman animals of the present invention following exposure of the transgenic nonhuman animals to a mutagen to induce reverse mutation of the reporter genes to a functional condition, e.g., the wild or functional type, the labeled substrates can then be phosphorylated intracellularly and used in nucleotide and nucleic acid biosynthesis. Those cells which have incorporated the labeled or tagged substrates in vivo can then be detected and/or visualized in vivo to confirm which mutated reporter genes have undergone the mutagenic event. Moreover, because the mutations required for reversion in the mutated reporter genes are known, the assays of the instant invention will automatically reveal the type of mutation induced in vivo by the mutagen.

With respect to the "forward mutation" of a gene, such as aprt, in a cell heterozygous or hemizygous at that locus, e.g., from APRT⁺ genotype to APRT⁻ genotype, in accordance with the instant invention, it will render those cells incapable of metabolizing the substrate, such as adenine or adenine analogs like 2,6-diaminopurine (DAP) and 2-fluoroadenine (2-FA) whose metabolic products are toxic to the cells. Thus, when transgenic nonhuman animals having heterozygous or hemizygous reporter genes are produced in accordance with the present invention, their cells will be capable of expressing the appropriate enzymes to metabolize the substrates intracellularly. However, after exposing the transgenic nonhuman animals of the instant invention to a selected mutagen to thereby induce the reporter genes to mutate, the mutated cells will no longer be capable of catalyzing the biochemical reactions intracellularly. Thus, as a further feature of the present invention, cells derived from animal tissues that have undergone forward mutations at the reporter genes, e.g., from APRT⁺ genotype to APRT⁻ genotype cells, can be placed into tissue culture and subsequently selectively grown in for example DAP or 2-FA, and those APRT cells that have incurred no mutation will be selectively killed, so that the APRT⁻ cells can be identified. As an alternative, DAP or 2-FA can be administered to the transgenic nonhuman animals following exposure to such a mutagen to selectively ablate those APRT cells that have not undergone a forward mutation at the APRT⁺ locus to identify in vivo the APRT⁻ cells.

In carrying out the assays of the present invention, the transgenic nonhuman animals are first exposed to a selected mutagen or environment for a sufficient period of time to induce the mutagenic event within the mutant or heterozygous reporter genes. The interval between mutagen administration and analysis can range from about one day to about one year or more and preferably from about one to about two weeks. Mutagens may include chemicals, such as benzo[a]pyrene (Bp), beta-naphylamine, N-ethyl-N-nitrosourea (ENU), and cyclophosphemide (Cp), complex mixtures like cigarette smoke or the like, or radiation. They may be administered to the animal by, for example, inhalation, injection, mouth, or exposure in an amount effective to induce the desired forward or reverse mutation. As an alternative, mutagens may also include temperature and pressure changes, differences in oxygen concentrations or environments to elicit the desired forward or reverse mutation. Following administration of or exposure to a mutagen or a potentially mutagenic environment, appropriate labeled or tagged substrates are administered in suitable amounts to the transgenics. The transgenic nonhuman animals are then observed for a selected period of time, approximately a 24-hour period, to permit them to clear unmetabolized labeled substrates from their systems. After the selected period of time has passed, in the case of reverse mutations, the transgenics may be exposed to, for example, NMR, MRI or PET or other monitoring systems, or sacrificed or sampled and their radioactivity counted to detect the labeled substrates incorporated intracellularly in the cells of the transgenics to confirm the mutagenic event. In the case of forward mutations, the transgenics can then be sacrificed or sampled to detect calls in vitro which are incapable of metabolizing substrate analogs, such as adenine analogs, whose metabolic products are toxic to the cells with functional enzyme.

Quite amazingly, the action of a mutagenic agent on an endogenous target reporter gene can now be assessed in vivo when following the teachings of the instant invention. For example, forward mutation of an endogenous reporter gene, like aprt, will identify the preferred tissues and cell types in which a substance exerts a mutagenic effect in vivo. Further, it will allow for the determination of the preferred types of mutation within the same gene in different tissues by, for example, DNA sequencing. Reverse mutation within a mutant reporter gene, like aprt, in an animal homozygous compound heterozygous or hemizygous for a known mutation in that mutated reporter gene will identify the tissues and cell types in which a mutagenic agent has reverted the mutated reporter gene to wild type in vivo, and with what efficiency. In both embodiments, the mutagenic action of an agent upon an endogenous gene in its proper chromosomal location is determined, as is the preferred cell type(s) or tissue(s) in which the mutations will occur. In connection with the detection of forward mutations, it may require invasive techniques, such as removing tissue from the animals or sacrificing the animals, to detect the forward mutations. However, when detecting reverse mutations in accordance with the instant invention, it uniquely affords the added advantage of facilitating non-invasive methods for the in vivo detection of the mutations in the reporter genes by methodologies, such as MRI, NMR, PET and the like.

It is believed that when following the teachings of the instant invention, one can uniquely establish which tissues in the animals respond to a given agent or environment, and whether or not the route of administration (i.e., oral, inhalation, injection, topical, etc.) affects the distribution of tissues that respond, and whether or not the agent or its metabolic products cross the placenta and/or the blood-brain barrier.

In accordance with the present invention, the genetically engineered nonhuman animals may be bred from chimeric nonhuman animals that are produced through the use of gene targeting in animal embryonic stem cells (ES cells). An example of a novel genetically engineered nonhuman animal of the instant invention is an APRT-deficient animal, such as an APRT-deficient mouse. Such an APRT-deficient animal can be produced following successful gene targeting in animal embryonic stem cells in accordance with the instant invention. The APRT-deficient animals are believed to be suitable to aid in the study of the in vivo regulation, function and structure of the APRT gene, provide a unique live system for whole-animal studies and detection of mutagenesis and potential carcinogenesis, and enable fate mapping of cells.

Importantly, the present invention provides for the non-invasive detection of reverse mutations in nonhuman animals (e.g., mice) to determine which organs/tissues/cells have undergone mutagenic events. The nature of the instant invention uniquely affords the opportunity to follow the fate of these cells through the life of the animals. Thus, for example, periodic examination for the presence of tumors throughout the life of the animals affords the unique opportunity to correlate the incidence and location of tumors (carcinogenesis) with the incidence and location of mutagenesis. Further, in one embodiment of the instant invention, the incidence and location of tumors can be correlated with the occurrence of specific types of mutations.

The advantages of the present invention over the existing state of the art are numerous. For example, in the case of reverse mutations, animals no longer need to be sacrificed, since the end results of the reverse mutations of interest can be visualized in whole, living animals by, for example, magnetic resonance imaging (MRI), nuclear magnetic resonance (NMR), or positron emission tomography (PET) imaging, or other whole body monitoring methodology. The aforementioned imaging techniques are believed to afford a high degree of resolution with regard to localizing said mutations, especially as compared to dissection of tissues prior to analysis for mutation. Thus, it is believed to now be possible to detect mutagenesis in specific, small segments of tissues or organs in vivo. This is especially important in resolving areas of mutagenesis in embryos or newborns. In the alternative, it is believed that the present invention permits cells that have sustained a mutation at the target locus to be subsequently visualized at an extremely high level of resolution, e.g., one cell in histologic sections, by virtue of their specifically incorporating a labeled or identifiable substance, e.g., autoradiography, reacting with a histochemical dye, reacting with a specific antibody, or being detected with imaging technology. In yet another alternative, the present invention permits the detection of mutation by measurement of total incorporation of a labeled substrate, such as labeled adenine, guanine, hypoxanthine or xanthine, in the whole animal or tissues of the animal. This can be accomplished by, for example, disintegrating the sacrificed animal or removing tissue therefrom following a.) exposing the animal to a mutagen, b.) administering the labeled substrate to the animal, and c.) detecting the labeled substrate retained after an appropriate time period in the whole animal, organs or tissues.

In addition, high resolution of mutagenesis enables the detection of many mutagenic events in a single genetically engineered animal, thereby eliminating the need to resort to a large number of animals. For example, a mouse is comprised of about $10^{12}$ cells. If a single mutagenized cell can be detected, one can, in principle, derive $10^{12}$ data points from a single mouse. If an imaging technique has the resolving power the size of the radius of a mass of 1,000 cells, then $10^9$ data points are available from a single animal with the present invention. Conventional animal tests such as those discussed earlier in the Background rely upon exposing large numbers of animals, e.g., 10,000, to a suspected mutagen. Subsequent to exposure, these animals must be maintained for extended periods to observe mutations. However, in accordance with the present invention, far fewer animals need be exposed, e.g., 10, to obtain many more data points. Further, unless one wishes to maintain the animals in order to screen for subsequent carcinogenic affects, the animals need not be maintained after imaging. Thus, much of the expense, time and effort of conventional animal assays is eliminated.

As a further advantage, the fate of the mutant cells and their progeny can be followed during the life cycle of the animals as a function of time, since the animals are not sacrificed when monitored. Thus, the present invention allows one to follow the developmental fate, as in "fate mapping," of cells, and progeny of cells, that have undergone mutation at the target locus. Thus, one can observe the subsequent fate of embryonic cells that sustain a mutation at the target locus. The normal cell or tissue derivatives of the "marked" cells, as well as any abnormal derivatives, can be determined by periodic observation of the animal. In addition, the present invention allows one to follow the developmental fate of cells in which an introduced functional gene, such as the APRT gene, is directed by a tissue specific or developmentally regulated promoter.

In yet another advantage, the assays of the instant invention permit the quantitation of the mutagenesis of an endogenous gene within its proper context. For example, one may evaluate mutagenesis within the murine APRT gene at its normal locus. In still another advantage, in one or more embodiments of the present invention, the mechanism of mutagenesis is revealed, e.g., whether mutagenesis is caused by a specific substitution, transition, transversion or frameshift. Further, the mechanism is revealed without having to sequence any DNA in those situations where, for example, aprt activity is generated only by same site reversion.

The present invention also contemplates applications in the area of gene and enzyme therapy. For instance, when following the teachings of the current invention with respect to gene and enzyme therapy, data may be gathered which is believed at present to be unavailable and may have importance to the design of gene therapy protocols for treating inherited diseases and cancer. For example, in one such embodiment, the genetically engineered nonhuman animals (e.g., mice) described herein are believed to be useful to test the efficacy of vectors that deliver therapeutic genes, such as normal genes, to combat genetic disorders wherein the normal genes are defective such as in adenosine deaminase deficiency, cystic fibrosis, Lesch-Nyhan syndrome, APRT deficiency, etc. In the alternative, the genetically engineered nonhuman animals described herein are believed to be further useful to test the efficacy of vectors that deliver therapeutic genes, such as il-2 (interleukin-2), tnf (tumor necrosis factor)) or nucleic acids (e.g., antisense RNA), to malignant cells. To determine the tissue or tissues targeted by a vector, such as a virus (e.g., retrovirus, adenovirus, poxvirus, parvovirus, etc.), liposomes, etc., a reporter gene as described herein (e.g., aprt, hprt, tk) is incorporated into the DNA or RNA or interior of the vector. After treating the nonhuman animal with the vector by a preferred route of administration, the animal is examined for the expression of the reporter gene by administration of a proper labeled substrate and use of one of the various methods described herein, such as MRI or PET imaging, sectioning followed by autoradiography, or disintegration followed by counting of radioactivity. It is believed that the pattern of label incorporation in the nonhuman animals will reveal the areas to which the gene (or nucleic acid) is delivered and expressed. Further, it is believed that the use of noninvasive imaging techniques will allow the nonhuman animals to be periodically examined such that a temporal pattern of gene expression may be determined. This information may be suitable to design and test vectors for the effective delivery of therapeutic genes or enzymes or other molecules to specific tissues or cells within the animal.

In another such embodiment with respect to gene therapy, a method may be used to gain information on the fate of cells that are introduced into an animal. For example, in instances of cancer or genetic disease, it is often desirable to replace diseased cells in tissues with either normal cells that have been genetically altered to a normal phenotype, or cells containing an introduced gene whose expression is therapeutic. For example, diseased marrow cells may be replaced by an autologous or heterologous transplant, muscle cells (myoblasts) or liver cells may be introduced, or cells containing a therapeutic gene (e.g., tnf or il-2) may be introduced. It is important to know whether or not said cells will populate certain tissues (e.g., marrow) and whether or not they or their progeny will survive in the recipient for extended periods of time. To aid in resolving these issues, cells containing an expressed reporter gene (e.g., aprt, hprt, tk) are introduced into an animal such as described herein (e.g., an Aprt⁻, Hprt⁻, or Tk⁻ mouse) and, after a period of time, their fate is examined by administering a suitable labeled substrate (e.g. labeled adenine, hypoxanthine, or thymidine). As in the previous example, the animals are sectioned, disintegrated or subjected to imaging by methods such as MRI or PET to determine the fate of the introduced cells. As in the previous example, periodic imaging can provide information on cell survival and on the mitotic expansion of introduced cells.

The present invention also contemplates those nonhuman animals which are heterozygous, homozygous or compound heterozygous for a mutated reporter gene that have been produced by methods other than gene targeting. For example, the present invention contemplates producing such nonhuman animals by selecting ES cells heterozygous for a reporter gene resulting from a spontaneous or induced mutation in one allele of the reporter gene locus in conditions such that those ES cells with two functional alleles of the reporter gene cannot survive. Alternatively, the present invention contemplates producing nonhuman animals by selecting ES cells which are homozygous, compound heterozygous or hemizygous resulting from spontaneous or induced mutations in both alleles of the reporter gene in conditions such that those ES cells that contain at least one functional allele of the reporter gene do not survive. Once the mutated ES cells have been selected they can be used to generate nonhuman germline chimerics and ultimately nonhuman transgenic animals in which the mutated reporter gene has been incorporated into all of the germ and somatic cells of the transgenic nonhuman animals. When producing nonhuman animals in accordance with these methods, the ES cells which are homozygous, compound heterozygous or hemizygous for the mutated reporter gene can be identified by cultivating them in certain selection media which are toxic to ES cells having at least one functional allele of a reporter gene. Likewise, when producing nonhuman animals with these methods, the ES cells which are heterozygous or hemizygous for the mutated reporter gene can be identified by cultivating them in certain selection media which are toxic to ES cells having more than one functional allele of the reporter gene. For instance, if the reporter gene is aprt, the ES cells can be cultivated in a medium containing an adenine analog, such as DAP or 2-FA, to identify those surviving ES cells wherein the APRT gene has undergone the mutagenic event. More particularly, for selecting ES cells that are homozygous or compound heterozygous for a mutated APRT gene, it is believed that a concentration of, for example, about 50 micrograms of DAP per ml of culture medium or about 5 micrograms of 2-FA per ml of culture medium can be used to selectively kill ES cells having at least one functional allele of a APRT gene. For selecting mutated heterozygous ES cells having a single functional APRT allele, it is believed that a concentration of, for example, about 5 micrograms of DAP per ml of culture medium can be used to selectively kill ES cells having at least two functional APRT alleles. Such mutated ES cells can then be used to develop the nonhuman germline chimerics and nonhuman transgenics as described herein. It should be understood by those versed in this art that the above-described ES cells may result from spontaneous or induced mutation by, for example, exposing the ES cells to a single mutagen or a plurality of mutagens. Likewise, it should be appreciated, the ES cells may be exposed once or repeatedly to the mutagen(s). The nonhuman animals having a mutated reporter gene may be produced by 1.) breeding the nonhuman germline chimerics and nonhuman transgenics to produce homozygosity, hemizygosity, heterozygosity or compound heterozygosity, or 2.) identifying those nonhuman animals that are homozygous, hemizygous, heterozygous or compound heterozygous which have been derived from the nonhuman chimerics, such as by DNA sequencing.

As an alternative, once a mutagen is known to induce a mutation in a reporter gene as a result of, for example, the present invention, the nonhuman animals for detecting mutations and other uses described herein may be produced by exposing nonhuman animals having a functional reporter gene to such a mutagen in an effective amount to induce a mutation in the reporter gene and breeding such nonhuman animals to produce nonhuman animals which are heterozygous, homozygous or compound heterozygous for the mutated reporter gene. It should of course be appreciated that when producing nonhuman animals by exposure, the mutation must occur in the nonhuman animals in such a manner that it can be incorporated into all of the germ and somatic cells of the progeny bred from the exposed nonhuman animals. In any of the above-produced nonhuman animals, the mutated reporter gene may be identified by methods disclosed herein and characterized by, for example, polymerase chain reaction (PCR) or DNA sequencing techniques well known to those versed in this art.

As a further alternative, the present invention includes nonhuman animals which are heterozygous, hemizygous, homozygous or compound heterozygous for a spontaneously mutated reporter gene that result from the natural selection process. While theoretically it is possible for such nonhuman animals to exist, it is currently believed that their existence is highly unlikely and very rare. Moreover, even if such a naturally occurring nonhuman animal exists, it is believed that it is highly impractical, if not impossible, to identify or locate such a naturally occurring nonhuman animal. Nonetheless, in the event such a nonhuman animal being heterozygous (functional), hemizygous (functional or nonfunctional), homozygous (nonfunctional) or compound heterozygous (nonfunctional) for a reporter gene may exist and can be located and identified, such nonhuman animals are contemplated by the instant invention.

It is believed that screening techniques such as those described herein and known in the art may be relied upon in an effort to attempt to identify such a naturally occurring nonhuman animal. For instance, it is believed that PCR and DNA sequencing may be utilized to screen for such a naturally occurring nonhuman animal. In addition, it is believed that the examination of nonhuman animals for symptoms characteristic of reporter gene product deficiency may also be utilized in an effort to attempt to identify such a naturally occurring nonhuman animal. For example, when looking for aprt deficiency, reduced levels of aprt activity in blood cells or the presence of unusual adenine metabolites or elevated adenine in the urine or plasma can be monitored. Once such a naturally occurring animal has been located, this nonhuman animal can then be tested to determine if one or more of its APRT alleles are mutated.

In accordance with the present invention, the alleles of the reporter gene may be mutated, modified or deleted. For instance, one or both alleles may be modified with a marker gene, mutated or deleted by, for example, gene targeting or other techniques known to those versed in the art. Depending upon the use, the reporter genes may be homozygus, compound heterozygous, hemizygous or heterozygous. For example, when looking for reverse mutations, it is preferable that the mutant genotype of the reporter locus be homozygous or compound heterozygous. A mutated hemizygous allele for a reporter gene may also be used in reverse mutation assays. With respect to forward mutation assays, reporter loci having one functional allele are preferred; that is, reporter genes having a functional heterozygous or hemizygous genotype. When monitoring the efficacy of gene or enzyme delivery systems in accordance with the present invention, reporter loci having no functional alleles are preferred. That is, where the reporter gene has been mutated or modified such that the allele(s) are not functional and are homozygous, compound heterozygous or hemizygous for the mutation or modification. It is especially preferred to monitor the efficacy of gene or enzyme delivery systems where all alleles of the reporter gene in question have been deleted. Examples of genotypes contemplated by the present invention include reporter gene$^{Mx}$/reporter gene$^{Mx}$, reporter gene$^{My}$/reporter gene$^{My}$, reporter gene$^{Mx}$/reporter gene$^{My}$, reporter gene-marker gene/reporter gene$^{Mx}$, reporter gene-marker gene/reporter gene$^{My}$, reporter gene-marker gene/ reporter gene-marker gene, reporter gene$^{Mx}$/−, reporter gene$^{My}$/−, reporter-gene marker gene/− and −/−. The designation "Mx" refers to a known mutation in one allele of a reporter gene or sequence thereof. The designation "My" refers to an unknown mutation in one allele of a reporter gene or sequence thereof. The designation "−" refers to the deletion of one allele or the functional portion thereof of a reporter gene. The designation "reporter gene-marker gene" refers to a reporter gene or sequence thereof which has been modified with a marker gene or a sequence thereof.

The above features and advantages of the present invention will be better understood with reference to the following accompanying FIGS., Detailed Description and Examples which are illustrative of the present invention.

DESCRIPTION OF THE FIGS

With reference to the accompanying FIGS. which are illustrative of certain embodiments within the scope of this invention:

Figure 2:
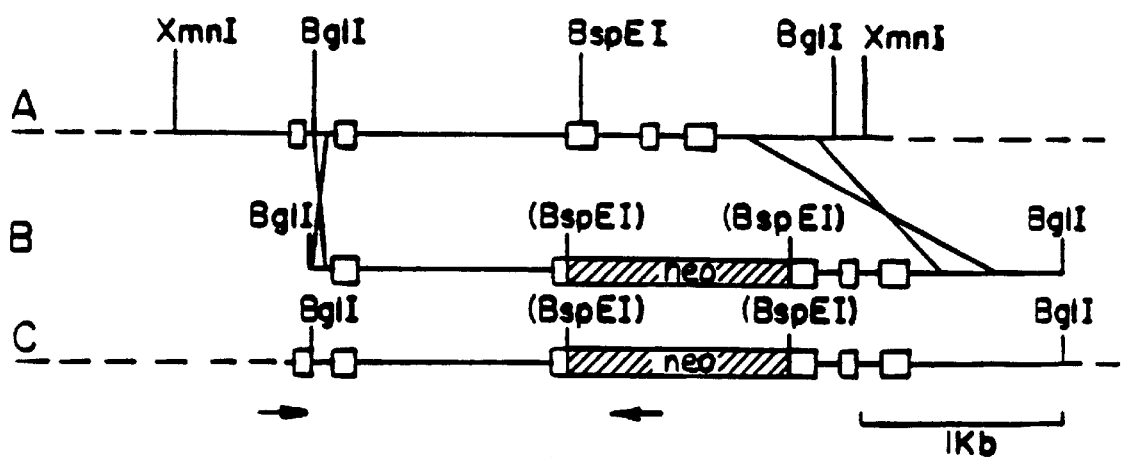
Figure 3:
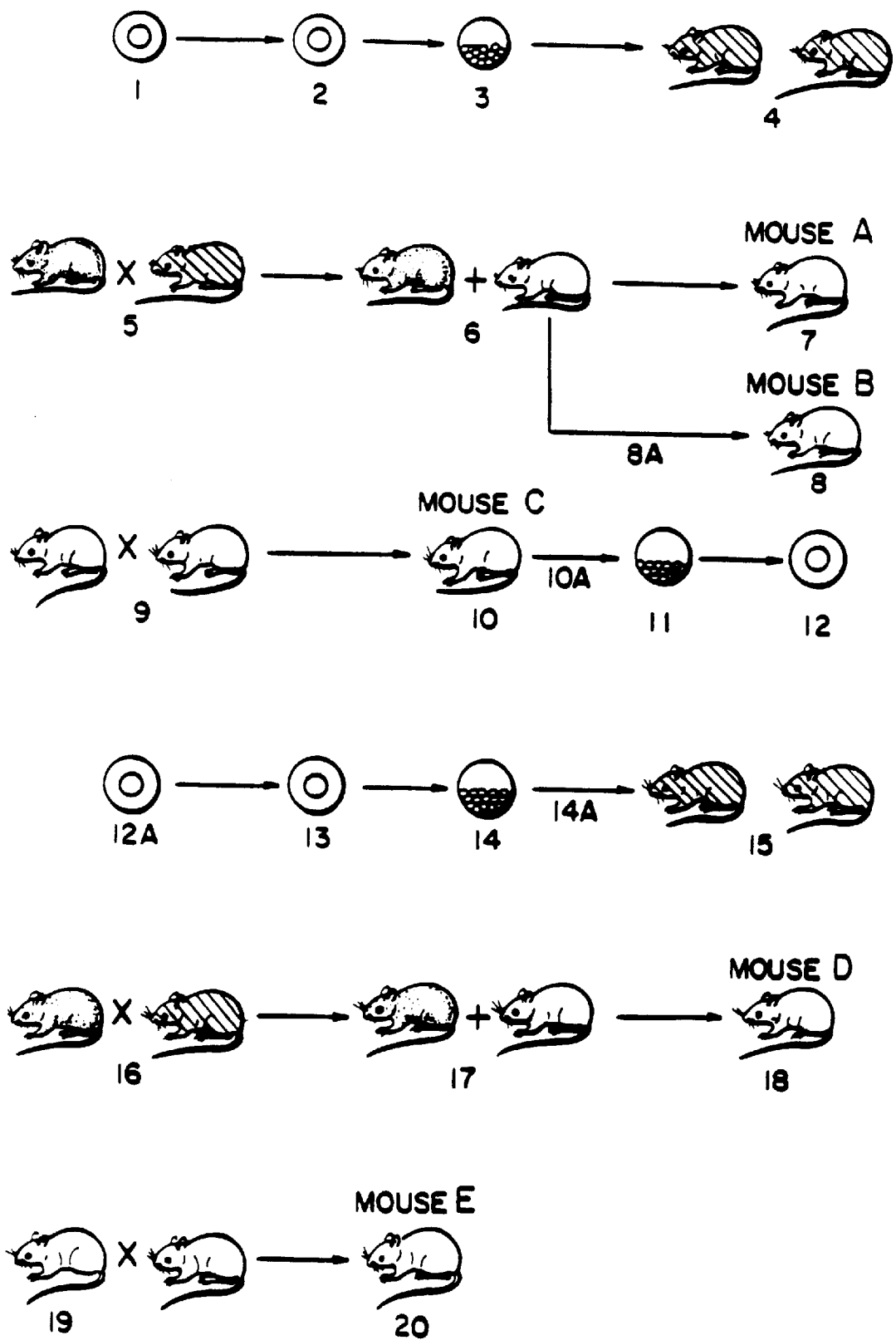

FIG. 2 depicts a schematic representation of recombination events between an alternative targeting vector and a targeted genomic sequence. Line A represents genomic mouse aprt with exons indicated by open boxes. Line B represents the completed targeting vector containing neo which is shown as a striped box. Recombination between the targeting vector and the genomic sequence produces the genomic sequence shown in line C in which exon 3 of aprt is disrupted by neo. The two horizontal arrows indicate the locations of oligonucleotide primers for PCR amplification to determine proper targeting; and FIG. 3 depicts a flow chart for introducing mutations into ES cells for producing chimeric and transgenic mice and for breeding mice to heterozygosity and homozygosity at the aprt locus in accordance with the teachings of the present invention. The striped mice designate chimeric mice. The stippled mice designate C57BL/6 mice. The white mice designate transgenic mice. The numerical legends in FIG. 3 correspond to the numerical steps summarized as follows:

1. ES cells 129/SV$^+$/+ APRT$^+$/APRT$^+$ are electroporated with APRTNEO gene;
2. ES cells 129/SV$^+$/+ APRT$^+$/APRTNEO are injected into C57BL/6 mouse blastocyst;
3. Chimeric blastocyst of step 2 are implanted into uterus of pseudopregnant female mice;
4. Chimeric mice are born from step 3;
5. Mate C57BL/6 mice with chimeric mice of step 4;
6. Black and Agouti mice are born from the mating of step 5, and test Agouti mice of step 6 for APRTNEO gene;
7. Heterozygous Agouti APRT$^+$/APRTNEO mice (Mice A);
8. Heterozygous Agouti APRT$^+$/APRTNEO mice (Mice B);
8A. Mate Agouti mice of step 6 with 129SV$^+$/+ mice, and test for APRTNEO gene;
9. Mate APRT$^+$/APRTNEO mice from step 7 with one another or step 8 with one another;
10. Approximately 25% APRTNEO/APRTNEO mice are born from the mating of step 9 (Mice C);
10A. Mate the APRTNEO/APRTNEO mice of step 10 with wild-type 129/SV$^+$/=;
11. Retrieve 129/SV$^+$/+ blastocysts APRT$^+$/APRTNEO from the mating of step 10A;
12. Produce—APRT$^+$/APRTNEO 129/SV$^+$/+ ES cells;

12A. Electroporate the APRT⁺/APRTNEO ES cells from steps 2 or 12 with a mutant APRT gene having a known or unknown mutation;
13. Produce APRT$^{Mx}$/APRTNEO ES cells;
14. Inject the chimeric blastocysts of step 14 into C57BL/6 blastocyst to produce chimeric blastocysts;
14A. Implant the chimeric blastocysts of step 14 into uterus of pseudopregnant female mice;
15. Chimeric mice are born from step 14A;
16. Mate C57BL/6 mice with chimeric mice of step 15;
17. Black APRT⁺/APRT⁺ and Agouti APRT$^{Mx}$/APRT⁺ or APRT$^{Mx}$/APRTNEO mice are born from the mating of step 16;
18. Test Agouti mice for APRT$^{Mx}$/APRT⁺ gene (Mice D);
19. Mate Agouti APRT$^{Mx}$/APRT⁺ mice of step 18; and
20. Approximately 25% APRT$^{Mx}$/APRT$^{Mx}$ mice are born from the mating of step 19 (Mice E);

It will be understood that the particular FIGS. embodying the present invention are shown by way of illustration only and not as limitations of the present invention. The principles and features of this invention may therefore be employed in various and numerous embodiments without departing from the scope of the invention.

DETAILED DESCRIPTION OF THE INVENTION

By way of illustrating and providing a more complete appreciation of the present invention and many of the attendant advantages thereof, the following detailed description is given concerning the novel live animal mutagenesis/carcinogenesis systems, such as transgenic nonhuman animals, for testing mutagenic agents in vivo, novel chimeric nonhuman animals, or animals having modified or mutated reporter genes, which can be bred to produce the transgenic nonhuman animals, novel cell lines for use in developing the chimerics and the live model systems, novel gene targeting vectors for use in developing the cell lines, methods for testing mutagenic agents and methods for determining the efficiency and effectiveness of gene and enzyme therapy vectors.

The chimeric and transgenic test animals in accordance with the instant invention are generated using genetically manipulated embryonic stem (ES) cells or tetraocarcinoma (EC) cells. Embryonic stem cells are pluripotent cells derived from the inner cell mass of cultured blastocyst-stage embryos. ES cells retain the potential for differentiating into any cell type in the animal body and have been used heretofore to contribute to the germline of chimeric mice when introduced into host blastocysts. Gene targeting, the consequence of homologous recombination between genomic and exogenous DNA sequences, introduces specific changes into the genome. Thus, when the targeted cells are pluripotent ES cells, specific gene modifications may be transferred to the germline of chimeric and transgenic animals and propagated via mating. As indicated already, ES cells and their use in the production of chimeric and transgenic animals are well known, as disclosed in Robertson, E. J. in *Teratocarcinomas and Embryonic Stem Cells, A Practical Approach*, e.d. Robertson, IRL Press; and Oxford, Washington, D.C., 1987, and Hogan, B. et al. in: *Manipulating the Mouse Embryo: A Laboratory Manual*, Cold Spring Harbor Laboratory, 1986, which are incorporated herein by reference in their entireties.

By "chimeric nonhuman nonhuman animal(s)," the term is used herein in a broad sense and refers to animals whose tissues are comprised of cells of different origin, e.g., genetically modified ES cells and host cells from the recipient blastocyst. By "transgenic animal(s)," this term is also used herein in a broad sense and refers to animals which carry a modified gene or foreign gene in their somatic cells and in their germ cells such that it can be transmitted to subsequent generations by breeding.

Reporter genes that may be utilized in accordance with the instant invention to produce such chimeric and transgenic animals include, for example, aprt, hprt and tk. Once a reporter gene is selected, a gene targeting vector is formed for gene targeting. Preferably, the gene targeting vector is a promoterless construct which includes a promoterless open reading frame for 1.) a dominant selectable phenotype, i.e., a marker gene, for conferring ES cell resistance to agents, such as, G418, puromycin, hygromycin, histidinol, ouabain, vinblastine, adriamycin, bleomycin and p-glycoprotein pump, and 2.) DNA sequences of the target or reporter gene lacking a promoter. An example of a promoterless construct contemplated by the instant invention is a 2.5 Kb promoterless aprtneo construct containing a promoterless bacterial neomycin phosphotransferase (neo) gene flanked by mouse aprt sequences and having the following sequence as set forth in Table I.

SEQ ID NO: 1:

TABLE I

```
                                    10          20
                              CCGGGATTGACGTGAGTTTAG 30        40        50        60        70
CGTGCTGATACCTACCTCCTCCCTGCCTCCTACACGCACGCGGCCATGT

M S 80        90       100       110       120
CGGAACCTGAGTTGAAACTGGTGGCGCGGCGCATCCGCGTCTTCCCCGAC erGluProGluLeuLysLeuValAlaArgArgIleArgvalpheproAsp 130       140       150       160       170
TTCCCAATCCCGGGCGTGCTGTTCAGGTGCGGTCACGAGCCGGCGAGGCG PheProIleProGlyValLeuPheArgCysGlyHisGluProAlaArgAr 180       190       200       210       220
TTGGCGCTGTACGCTCATCCCCCGGCGCAGGCGGTAGGCAGCCTCGGGGA gTrpArgCysThrLeuIleProArgArgArgAr 230       240       250       260       270
TCTTGCGGGGCCTCTGCCCGGCCACACGCGGGTCACTCTCCTGTCCTTGT 280       290       300       310       320
TCCTAGGGATGCTGCAGCCAATATGGGATCGGCCATTGAACAAGATGGAT gAspAlaAlaAlaAsnMetGlySerAlaIleGluGlnAspGlyL 330       340       350       360       370
TGCACGCAGGTTCTCCGGCCGCTTGGGTGGAGAGGCTATTCGGCTATGAC euHisAlaGlySerProAlaAlaTrpValGluArgLeuPheGlyTyrAsp 380       390       400       410       420
TGGGCACAACAGACAATCGGCTGCTCTGATGCCGCCGTGTTCCGGCTGTC TrpAlaGlnGlnThrIleGlyCysSerAspAlaAlaValPheArgLeuSe
```

TABLE I-continued

```
        430       440       450       460       470
AGCGCAGGGGCGCCCGGTTCTTTTTGTCAAGACCGACCTGTCCGGTGCCC
rAlaGlnGlyArgProValLeuPheValLysThrAspLeuserGlyAlaL
        480       490       500       510       520
TGAATGAACTGCAGGACGAGGCAGCGCGGCTATCGTGGCTGGCCACGACG
euAsnGluLeuGlnAspGluAlaAlaArgLeuSerTrpLeuAlaThrThr
        530       540       550       560       570
GGCGTTCCTTGCGCAGCTGTGCTCGACGTTGTCACTGAAGCGGGAAGGGA
GlyValProCysAlaAlaValLeuAspValValThrGluAlaGlyArgAs
        580       590       600       610       620
CTGGCTGCTATTGGGCGAAGTGCCGGGGCAGGATCTCCTGTCATCTCACC
pTrpLeuLeuLeuGlyGluValProGlyGlnAspLeuLeuSerSerHisL
        630       640       650       660       670
TTGCTCCTGCCGAGAAAGTATCCATCATGGCTGATGCAATGCGGCGGCTG
euAlaProAlaGluLysValSerIleMetAlaAspAla M ArgArgLeu
        680       690       700       710       720
CATACGCTTGATCCGGCTACCTGCCCATTCGACCACCAAGCGAAACATCG
HisThrLeuAspProAlaThrCysProPheAspHisGlnAlaLysHisAr
        730       740       750       760       770
CATCGAGCGAGCACGTACTCGGATGGAAGCCGGTCTTGTCGATCAGGATG
gIleGluArgAlaArgThrArg M GluAlaGlyLeuValAspGlnAspA
        780       790       800       810       820
ATCTGGACGAAGAGCATCAGGGGCTCGCGCCAGCCGAACTGTTCGCCAGG
spLeuAspGluGluHisGlnGlyLeuAlaProAlaGluLeuPheAlaArg
        830       840       850       860       870
CTCAAGGCGCGCATGCCCGACGGCGAGGATCTCGTCGTGACCCATGGCGA
LeuLysAlaArgMetProAspGlyGluAspLeuValValThrHisGlyAs
        880       890       900       910       920
TGCCTGCTTGCCGAATATCATGGTGGAAAATGGCCGCTTTTCTGGATTCA
pAlaCysLeuProAsnIleMetValGluAsnGlyArgPheSerGlyPheI
        930       940       950       960       970
TCGACTGTGGCCGGCTGGGTGTGGCGGACCGCTATCAGGACATAGCGTTG
leAspCysGlyArgLeuGlyValAlaAspArgTyrGlnAspIleAlaLeu
        980       990      1000      1010      1020
GCTACCCGTGATATTGCTGAAGAGCTTGGCGGCGAATGGCTGACCGCTT
AlaThrArgAspIleAlaGluGluLeuGlyGlyGluTrpAlaAspArgPh
       1030      1040      1050      1060      1070
CCTCGTGCTTTACGGTATCGCCGCTCCCGATTCGCAGCGCATCGCCTTCT
eLeuValLeuTyrGlyIleAlaAlaProAspSerGlnArgIleAlaPheT
       1080      1090      1100      1110      1120
ATCGCCTTCTTGACGAGTTCTTCTGAGGGGATCGGCAATAAAAAGACAGA
yrArgLeuLeuAspGluPhePhe-*-  SV40PolyA signal
       1130      1140      1150 BamH1160      1170
ATAAAACGCACGGGTGTTGGGTCGTTTGTTCGGATCCTTGTACTTTGTAC
       1180      1190      1200      1210      1220
ACGTCCCACACACCCTGGAGCATAGCAGAGCTGTGCTACTGGAGATCAAT
                                              APR
       1230      1240      1250      1260      1270
AAACCGTTTTGATATGCATGCCTGCTTCTCCTCAGTTTGTTGCATGGGTC
T PolyA signal
       1280      1290      1300      1310      1320
ACATTCCAGGCCTCCAGAGCGATACTACAGGGACAAGGGGGCTCAGGTGG
       1330      1340      1350      1360      1370
GAACCCATAGGCTCAGCTTTGTATTGAAGCCACAACCCCTACTAGGGAGC
       1380      1390      1400      1410      1420
AGATGTTATCTCTGTCAGTCTCTGAGGCAGCTGACTACATAAACAGGTTT
       1430      1440      1450      1460      1470
ATTGCTTCACTGTTCTAGGCCTGTTATTCCATTAGGATGGACGAGGATGA
       1480      1490      1500      1510      1520
AGCAGTGACCCACAGCCACTATATTTTTTCTGTTGTTTGTCGAGATGGG
       1530      1540      1550      1560      1570
GTTTCTTAATATAACCAGCCCTGGCTATTCTGGACTTGATTTGTAGCCCA
       1580      1590      1600      1610      1620
GGCTGGCCTCAAACTTAAGAGGTCCACTGCCTCTGCTTCTTGAGTGCTGG
       1630      1640      1650      1660      1670
GATCAAAGTACGCACCGCAACACCCAGTTCACAGTCACTATCTCAAAAAA
       1680      1690      1700      1710      1720
GCTATTTTGTTGCAGGGCATGGTGTATAGACCTTTAATCCTAGTGCCTTG
       1730      1740      1750      1760      1770
AAGGTAGGCAGGCTGTTAAAATTCAAGGCCAACCTGGCTATATAGTTCCA
       1780      1790      1800      1810      1820
AGGAGAGCCAGAGCTTTTAGAAAAAATAAAAATTTAAAAAATATATATCA
       1830      1840      1850      1860      1870
AGCCAGGCATGGTGGCACACACCTTTGATCCCAGCACTTGGGAGGCAGAG
       1880      1890      1900      1910      1920
GCAGGGCGGATTTCTGATCTACAGAATGAGTTCCAGGACAACCAGTTCTA
       1930      1940      1950      1960      1970
CAGAGAAACCCTGTCTCAAAAAAAAAAAAAAAATACATTCTGGGGAAGT
       1980      1990      2000      2010      2020
```

TABLE I-continued

```
GGGTGTTGGGGAAAGAGGGGGATGGGAGAGAGCCTGCGTCCCACCAGAGT
     2030      2040      2050      2060      2070
TCTGGTGCTCCAGGAGGCTGGATACTTTTCACACTGCCCCAGTGTGAGGC
     2080      2090      2100      2110      2120
TATCTGGCATGATGTTAAGCCAGTCTCCGGCACCCCACACTGGATATGGT
     2130      2140      2150      2160      2170
GGAGGAGCTGAGAACATAATAGGGACCCGGGCAGAAGGAAAGAGAGGGGG
     2180      2190      2200      2210      2220
GGGAAGGGAGGGGTGCTGGGTGGAGTCCTTAGTCTGGTCCATGGCTGCAG
     2230      2240      2250      2260      2270
CGTAGGAAGCCTTCTGGCAGGTTAAAAGTGCTCATTAGGAGAGCCTATCC
     2280      2290      2300      2310      2320
GATCATCATTCAAACACGGTGGGCCTTCATGATCAGAGACAGTCTATGGT
     2330      2340      2350      2360      2370
TTTAGAGCTTTATTGTAGAAAGGGAAGGAGAAAGAGAAGGTAGAAGGACA
     2380      2390      2400      2410      2420
GCCATGGCCACGTGGAGAGAGGGGGAAGGGAAAGAGAAAAAAAGCCAGA
     2430      2440      2450      2460      2470
GAGCTTAAGAGAGCGAGGAGGGGCCAAACATCCCCTTATAGTGGGCTTTG
     2480      2490      2500      2510      2520
CCATCTTGCTGTTGCTAGGTAACTGTGGGAAGGGAGTCTAGCCAGAATGC
     2530
CAGAAGCTT Hind III Sequence
```

The promoterless aprtneo construct may be prepared as follows and as set forth in greater detail hereinafter in Example I. An aprt genomic clone extending to the 3' HindIII site is deleted at the 5' end to remove the aprt promoter. In so doing, the deletion terminates at a XmaI site, destroying that site and producing a linkered EcoRl site. See Dush et al., *Nucleic Acids Res.*, 16:8509–8524 (1988), which is incorporated herein by reference in its entirety. This deletion construct is designated pdelta 807 and is believed to be the same as plasmid pIBI/-66, described in Dush et al., *Nucleic Acids Res.*, 16:8509–8524 (1988). Plasmid pdelta 807 contains the aprt DNA fragment extending from the linkered EcoRl site to the 3' HindIII site. The plasmid is modified by first cleaving the DNA at the EcoRV site in exon 2, and inserting and ligating the double stranded linker 5'GCTGCAGC3' containing a PstI site to the blunt end EcoRV-produced termini. The modified plasmid containing the new PstI site is digested with PstI and BamHI, and the intervening aprt sequence replaced by a promoterless neo DNA sequence which extends from a 5' PstI site to a 3' BamHI site. The resulting plasmid lacks an aprt promoter and a promoter driving expression of neo. The neo fragment has a 3' SV40 polyadenylation signal. The resultant protein is an in-frame chimera between exon 1 and part of exon 2, amino acids derived from the linker, and the neo gene product. The function of the linker is to ensure that the aprt sequence and neo sequence are in the same reading frame. See FIG. 1B.

The plasmid containing the construct depicted in FIG. 1B is digested with EcoR1 and HindIII to remove the insert, which is separated from the bacterial vector sequences by agarose gel electrophoresis. The separated EcoR1/HinIII insert is electroporated into ES cells cultured on transgenic, irradiated G418-resistant mouse embryo fibroblast feeder cells, and G418-resistant ES cells are selected. Several hundred independent G418-resistant ES cell clones are picked, pooled in groups of 10 and DNA from pools is isolated and subjected to amplification by PCR using primers, such as 5'-GAGAACCTGCGTGCAATCCATCTTG-3' (neo primer) and 5'-GCAGGACTGAAAAAGCGTGTGTGGGGC-3' (upstream aprt primer), positioned as shown by arrows in FIG. 1C. One primer is within the neo gene and is present within the targeting construct. See FIG. 1C. The other primer is within 5' flanking aprt DNA and is not contained within the targeting construct. Only DNA from clones that have undergone a legitimate targeted recombination event will allow amplification by the above-mentioned primers.

Other desired promoterless targeting vectors can be made in suitable plasmids, such as pUC 19, pGEM, pBSK Bluescript and the like, and may be prepared by standard techniques well known to those versed in the art.

To produce chimeric nonhuman animals, such as chimeric mice, in accordance with the instant invention, the source of the ES cells and the source of the recipient blastocysts are preferably selected based on genetic background to facilitate rapid visual identification of chimeric mice based upon coat color differences. Any of several suitable cultured totipotent ES cell lines may be used, such as D3, D3A1 and E14, which may be obtained from Dr. Thomas Doetschman, University of Cincinnati, College of Medicine, Cincinnati, Ohio. The cultured ES cells are typically derived from 3.5 day post coitum (p.c.) blastocysts obtained from agouti strain 129/Sv+/+ mice, aprt⁻ and the recipient blastocysts are 3.5 day (p.c.) blastocysts from C57BL/6 mice. See, for example, Doetschman, T. C. et al.: *J. Embyol. Exp. Morphol.*, 87:27–45 (1985). In all cases, individual cultured ES cell lines should be karyotyped and tested for pluripotency in vitro by allowing them to grow in the absence of a feeder layer, a procedure that promotes in vitro differentiation. The ES cells can be propagated using, for example, mitomycin C-treated STO mouse fibroblasts as feeder layers. The STO cells are a thioguanine-resistant and ouabain-resistant mouse fibroblast line. See, for example, Martin, G. R. and Evans, M. J.: *Proc. Natl. Acad. Sci. USA*, 72:1441–1445 (1975). The ES cells can also be maintained in the absence of feeder cells by culture in Buffalo rat liver cell-conditioned medium, Hooper M. et al.: *Nature*, 326:295–298 (1987), or in medium containing leukemia inhibitory factor, such as disclosed in Williams, R. L. et al.: *Nature*, 336:684–687 (1988) and Smith, A. G. et al.: *Nature*, 336:688–690 (1988). However, it is preferable to maintain the ES cells on feeder layers comprised of mitotically inactive primary mouse embryo fibroblasts whenever possible. Empirically, it appears that there is little tendency to become aneuploid when ES cells are grown on primary fibroblasts. Retention of euploidy, however, is imperative if the ES cells are to be used to generate viable chimeras and transgenic animals. Nevertheless, certain genetic manipulations, as described later, may necessitate transient use of one or the other alternative culture conditions. Primary mouse embryo fibroblasts (MEFs) are prepared by removing the liver and heart of 15 to 17 day embryos and trypsinizing the remainder of the embryo to produce a single cell suspension, which is plated and maintained by conventional means. MEFs are rendered non-mitotic by mitomycin-C treatment or exposure to about 3000 rad of ionizing radiation.

For production of chimeric and subsequent transgenic animals, ES cells with a male karyotype are preferable since chimeric male animals can sire more offspring, potentially containing the transgenes, than female animals can produce, thereby decreasing the time to test for germ line chimerism. Once it has been verified by Southern blots that the cultured ES cells have had the proper gene properly targeted by homologous recombination, they are ready for introduction into host blastocysts. The procedure for producing chimeric and transgenic mice generally follows that of Hogan, B. et al.: In *Manipulating the Mouse Embryo: A Laboratory Manual,* Cold Spring Harbor Laboratory (1986). Following injection of ES cells into recipient blastocysts, the resultant chimeric blastulae are transferred to the uterus of preferably a pseudopregnant Swiss albino or ICR female mouse, previously mated to a vasectomized Swiss albino or ICR male mouse. See, for example, Doetschman, T. C. et al.: *J. Embryol. Exp. Morphol.,* 87:27–45 (1985) and Williams, R. L. et al.: *Cell,* 52:121–131 (1988), which are incorporated herein by reference in their entireties.

Typically, chimeric mice can be visually identified by patches of agouti coat color against the black coat color characteristic of C57BL/6 mice, which are the source of host blastulae. The agouti color is produced by the descendants of the 129/Sv+/+ ES cells. Male mice that are potentially germ line chimeras will be tested for germline chimerism by back-crossing to C57BL/6 female mice. Heterozygotes will be totally brown since the agouti phenotype is dominant over the C57BL/6 black coat color. All agouti mice may be tested for the presence of the targeted gene by cutting off approximately 1.0 cm of tail and extracting the DNA by conventional means known to those versed in this art. The DNA is subjected to an appropriate restriction enzyme digestion, such as BamHl for the construct in FIG. 1, and probed with a suitable gene probe, such as the neo DNA sequence for the above construct in accordance with standard technology. Heterozygous mice bearing the transgene will be mated to one another, and progeny homozygous for the transgene (about 25%) will be identified by DNA analysis as above, using Xmnl digested DNA and 5' Xmnl/EcoRV DNA as a probe. APRT$^+$ homozygotes produce a single band at about 3.5 Kb; APRT$^+$/APRTNEO heterozygotes produce 2 bands at about 3.5 Kb and about 2.5 Kb; and APRTNEO/APRTNEO homozygotes produce a single band at about 2.5 Kb.

In one embodiment of the present invention, the cultured ES cells are genetically modified at, for example, the resident APRT genes by targeted homologous recombination via methodology well known to those versed in this art. This may be done in two steps, see FIG. 1, although variations of the below described methodology may be utilized. First, a cloned mouse APRT gene is modified by insertion of a Pstl linker inserted at the EcoRV site and further modified such that much of the body of the gene is removed by a Pstl/BamH1 digest and replaced with a bacterial NEO gene in the same reading frame as the APRT gene at the point of fusion, as described hereinbefore. The cloned APRT gene is also truncated at its 5' end so as to remove the APRT gene promotor. The final targeting DNA construct is comprised of about 280 bp of promoterless mouse APRT DNA at the 5' end, a promoterless NEO gene spliced to the introduced Pstl site to render it in frame with aprt, and either 1.5 kb or 6 kb of mouse aprt at the 3' side. The NEO gene also has an SV40 polyadenylation signal which precedes the APRT polyadenylation signal. This final vector has the aprtneo sequence as reported in Table I.

The rationale for constructing this vector as the initial targeting vector is as follows. The mouse APRT DNA flanking the bacterial NEO gene provides the homology with the endogenous gene that is required for gene targeting and consequent homologous recombination. The NEO gene provides a selectable marker to monitor successful introduction of the targeting vector into the host cell. Cells expressing the NEO gene become resistant to culture in the presence of the drug G418. Because neither the APRT gene nor the NEO gene on the targeting vector contains a promoter, the APRT-NEO fusion will only express and manifest G418 resistance if the targeting construct fortuitously integrates next to a promoter or integrates at the desired position, i.e., the endogenous APRT gene, by homologous recombination. Since the former event is believed to be relatively rare, the design of the targeting vector enriches for the latter event. Thus, the design of a promoterless APRTNEO fusion gene, which confers G418 resistance, is intended as a method to enrich for the desired targeting event. To ensure that the G418 resistant ES cell clones have undergone the desired targeting event, the DNA from these cells is subjected to polymerase chain reaction (PCR) DNA amplification using primers that reside in the NEO gene and in upstream APRT sequences that are not contained on the targeting vector but are present in the endogenous gene. Thus, only cells that have undergone the proper recombination event have the primer sequences in sufficiently close apposition to permit amplification of intervening DNA. Targeted cells should then be further analyzed by Southern blot analysis to ensure the absence of unwanted, randomly integrated NEO DNA.

The ES cells produced from the above targeting procedure are heterozygous at the APRT locus. One allele is wild-type and the second has part of the APRT gene replaced by an in-frame NEO sequence. Thus, the ES cells are aprt$^+$, G418 resistant. In one embodiment, this cell line may then serve as the recipient for a series of individual second targeting events in which the targeting DNAs are mutant APRT genes with point mutations at the intron 3 splice acceptor site or a frameshift mutation elsewhere in the gene. Mutations at this site destroy aprt activity and concomitantly destroy a diagnostic Pstl restriction site. Following individual introduction of mutant genes by electroporation, clones that potentially have undergone the correct targeting event are selected by their Aprt$^-$ phenotype and their consequent ability to grow in medium containing 2,6-diaminopurine (DAP) or in 2-fluoroadenine (FA). DNA from each of these candidate clones is examined by PCR amplification, using primers that flank the intron 3 splice acceptor site, followed by digestion with the Pstl restriction enzyme. If the enzyme cuts the amplified product, the Aprt$^-$ phenotype is not a consequence of correct DNA targeting, but of mutation in the resident aprt wild-type gene. If the enzyme does not cut the amplified product, the gene containing the mutation at the intron 3 splice acceptor site has been introduced into the gene. To ensure that the mutant, introduced gene has not integrated illegitimately, the correct junctional fragments at the 3' and 5' ends of the targeting vector will be confirmed by Southern blotting. The chimeric mice will be produced by introduction of genetically modified ES cells into host blastulae and their implantation into the uteri of pseudopregnant females as is described herein.

In a second embodiment, the above described ES cells, heterozygous at the reporter gene, such as aprt, may be selected further in medium containing DAP or FA for Aprt$^-$ cells that have incurred a mutation in the functional APRT allele. The mutations in these cells are identified by, for example, PCR amplification and DNA sequencing. The ES cell can be used to produce the chimeras. The chimeras then can be used to produce the transgenics.

To develop a mammalian cell mutagenesis assay in accordance with this invention, Schaff, D. A. et al.: *Proc. Natl. Acad. Sci. USA,* 87:8675–8679 (1990), site-directed mutagenesis may be used to insert defined point mutations into wild-type mouse APRT genes. Table M indicates the location of some of the mutations that have been introduced and may be used. The sites for mutation are preferably chosen because they are highly conserved between *E.coli*, mice and man and the introduced changes are predicted to alter mRNA splicing or protein conformation and/or charge. What are believed to be the best characterized of the introduced mutations, designated M1 through M6, represent six mutant permutations of the invariant AG splice acceptor sequence of intron 3. See Table M. See also, for example, Schaff, D. A. et al.: *Proc. Natl. Acad. Sci. USA,* 87:8675–8679 (1990); and Dlouhy, S. R. et al.: *Mol. Carcinog.,* 2:217–225 (1989). Each of the six mutations results in the loss of a diagnostic Pst1 site. Transfection of each of the mutations into an aprt⁻ human cell line should not support aprt activity. The M1–M6 mutations are further characterized in Example II.

TABLE M

Invariant 5'---CTGCAG/GCT---3' Splice Acceptor
Sequence of Intron 3 in Wild-Type APRT Gene

| Mutation | Nucleotide Base Change |
|---|---|
| M1 | AA/GCT |
| M2 | GG/GCT |
| M3 | AT/GCT |
| M4 | AC/GCT |
| M5 | CG/GCT |
| M6 | TG/GCT |

In forming the transgenic mice, it is preferable to introduce mutations M1–M6 in ES cells to form chimeric mice. An ES cell line heterozygous at the aprt locus will be established by targeted disruption of one of the two endogenous APRT genes. Once a pluripotent Aprt⁺/⁻ES cell line has been generated, mutations M1–M6 can each be introduced via gene targeting into the remaining unaltered aprt allele in accordance with the procedures as described for the aprtneo gene. APRT-deficient ES cells can then be selected and used to produce chimeric mice. By selective breeding of germline chimeric mice, mice homozygous for each of the mutations can be generated.

It is believed that mice carrying site-specific mutations within a selectable APRT gene will provide a unique in vivo model of both spontaneous and induced mutagenesis.

It is also believed that the development of an in vivo model of mutagenesis based on reversion of Aprt⁻/⁻ cells in mice to an Aprt⁺ phenotype will provide several advantages over the systems presently available. First, normal aprt is a ubiquitously transcribed, highly conserved endogenous gene whose functional absence from cells im vitro and in vivo is not detrimental to cell function. This suggests that all cells of all organs of an Aprt⁻/⁻ mouse would be capable of regaining aprt activity upon mutagenic reversion of the mutated APRT gene to wild-type. Analysis of such reversion to an Aprt⁺ phenotype is not likely to be complicated by transcriptional regulation in a particular cell type. In addition, information gathered in one species (mouse) can be extrapolated to APRT genes in other species (human).

Second, this assay requires the site-specific reversion of a known base pair change in order for aprt activity to be regained. Theoretically, this would lower the rate of spontaneous background mutation, thus allowing for identification of an increase in reversion induced by mutagen treatment. In addition, the exact mutational event that had occurred at the molecular level in all Aprt⁺ cells will be known since the type of mutation required to regain APRT activity is known. In vitro experiments have shown that the likelihood of a second-site mutation leading to aprt activity in M1–M6 is extremely small or nonexistent. By testing putative mutagens on multiple strains of mice, each carrying a different mutation, not only compounds that are mutagenic may be identified, but the type(s) of base pair substitution(s) they cause may also be determined. The development of mouse strains each carrying a different base pair substitution at their aprt locus will allow for the examination of differences between mutation rates of different base pair changes at the same site within the gene. Differences between mutation rates in different cell types and organs of a mouse carrying the same mutation in all of its cells can also be determined. The in vivo nature of the assay will allow for the determination of the mutagenicity of various compounds at different developmental stages.

By homologous recombination, using a "promoterless neo" vector, a pluripotent aprt⁺/⁻ES cell line capable of contributing to the germline of chimeric mice should be generated. Second, by homologous recombination site-specific mutations may be introduced into the second endogenous APRT gene in the Aprt⁺/⁻ES cells. This will permit for the breeding of mice homozygous for each site specific mutation.

The final product of one embodiment of the instant invention is a series of animal lines, e.g., mouse lines, homozygous for different mutant genes, such as mutant APRT genes, targeted to the endogenous gene locus. The final products of other embodiments of the of the present invention are 1.) a series of animal lines, such as mouse lines, having one functionally inactive reporter gene like an APRT gene, or 2.) animal lines, such as mouse lines, homozygous for a disrupted reporter gene like aprt. All cells of the animals of the first embodiment, i.e., animal lines homozygous for different mutant genes targeted to the endogenous gene locus, and the homozygous animals of the second embodiment, i.e., animal lines homozygous for a disrupted reporter gene, are, for example, aprt⁻ and cannot metabolize adenine or an isotopically tagged adenine derivative. Any cell that reverts to aprt⁺ by reversion or that is rendered aprt⁺ by introduction of a functional APRT gene can metabolize adenine or an isotopically tagged derivative, and incorporates its metabolic product, AMP, into nucleic acids. When adenine or a derivative is labeled, e.g. tritiated, deuterated, and/or labeled with $^{14}C$ and/or $^{15}N$, $^{19}F$, or $^{79}BR$ and administered by injection, feeding or other method, the revertant cell (mutagen induced or spontaneous) and its descendants can be detected and followed by whole body imaging (e.g. MRI or NMR). A significant advantage is that the animal need not be sacrificed for examination and can be followed as a function of time. A further advantage is that the metabolic product of the APRT reaction, AMP, is a small molecule that can pass through gap junctions that couple cells in most tissues, a phenomenon known as metabolic cooperation. Thus, when cells are coupled via gap junctions, the signal is expanded from the single cell or nucleus of cells containing the reverted APRT gene to the surrounding, coupled cells. The revertant cell emits the most intense signal, with diminishing signal intensity as a function of distance. The precise number of cells with a mutation within the APRT gene target and their localization may be verified if radioactively labeled adenine is utilized. After administration of the labeled adenine the animals may be imaged, using for example radioactivity or sacrificed and histological sections prepared and then subjected to autoradiography.

While reversion of mutated APRT genes in transgenics and the metabolism of labeled adenine or derivatives thereof is a detection system of choice, there are alternative approaches. These include reversion of HPRT genes, GPT genes and thymidine kinase (tk) genes in transgenics and metabolism of their respective labeled substrates.

In another embodiment of the instant invention, it involves rendering animals, such as mice, deficient for tk and replacing the functional tk gene with a series of mutant tk genes bearing a set of defined transitions, transversions, point deletions, etc. The cells of these mice are incapable of metabolizing and incorporating into their DNA the metabolites isotopically labeled thymidine or 5-bromodeoxyuridine (BrdUrd), a thymidine analog. Any cell that reverts to a $tk^+$ phenotype will phosphorylate and incorporate the labeled thymidine or the BrdUrd into DNA, and those labeled cells and their coupled neighbors will provide the signal that is detected by MRI imaging or other imaging methodology or by sectioning of animals or by whole animal or tissue counting.

Another embodiment of the present invention involves producing genetically altered mice in which the gene for a cell surface or other antigen is replaced by one containing a mutation such that the product that it encodes can no longer be recognized by an antibody directed at the wild-type epitope(s). This epitope is missing in the tester mouse but will be regenerated following a reverse mutation event within the gene encoding the antigen, thereby reestablishing the wild-type epitope in that cell and its progeny. The reversion event can be detected by whole body imaging following administration of isotopically or otherwise labeled antibody. An example of such a cell surface antigen, which is expressed on the surface of most cells and which is not essential for the development of the mouse, is beta-2 microglobulin. The endogenous gene may be modified so that an epitope recognized by an antibody is lost. Upon reverse mutation (same site or second site mutation) the epitope is reestablished, and the occasional cells that express the epitope can be detected. An alternative embodiment involves forward mutation to reestablish expression of a repressed APRT gene or other reporter gene. As one example of this embodiment, the mutagenesis target is a gene that encodes a protein that represses expression of aprt or other reporter genes. When the repressor gene sustains a mutation, the repressor protein is rendered non-functional and reporter gene activity is restored and can be monitored as above. An example of this method involves the use of the bacterial lactose regulatory system. In this case, appropriate regulatory sequences (lactose operator) are introduced into or near the promotor region of the APRT gene or other reporter gene by gene targeting, as above. The gene encoding the repressor is introduced into the same animal as a single copy and its product prevents expression of the reporter gene (e.g., aprt). If the repressor gene (lacI) incurs a mutation, the repressor is crippled and aprt expression is reestablished in that cell and its progeny.

The present invention will now be further illustrated with reference to the following Examples.

EXAMPLE I

Production of Targeted ES Cells and Chimeric and Transgenic Mice

Adenine phosphoribosyltransferase (APRT: EC 2.4.2.7), a ubiquitously expressed purine salvage enzyme, catalyzes the synthesis of adenosine monophosphate (AMP) and inorganic pyrophosphate from existing adenine and 5-phosphoribosyl-1-phyrophosphate. The extensive characterization of the APRT gene from several species and the ability to select for either an $aprt^+$ or $aprt^-$ phenotype has made the aprt locus a popular choice for studies of gene mapping, gene regulation and spontaneous and induced mammalian gene mutations. Kozak, C. E. et al.: *Somat. Cell Genet.*, 1:371–382 (1975); and Kang, C. Y.: *J. Virol.*, 40:946–952 (1981), DNA replication, Handeli, S. et al.: *Cell*, 57:909–920 (1989); Taylor, M. W. et al.: *Adv. Exp. Med. Biol.*, 253A:467–473 (1989); Singer-Sam, J. et al.: *Nucleic Acids Res.*, 18:1255–1259 (1990); and Turker, M. S.: *Somat. Cell Mol. Genet.*, 16:331–340 (1990); Miles, C. et al.: *Mol. Carcinog.*, 3:233–242 (1990); deBoer, J. G. et al.: *Carcinogenesis*, 10:1363≧1367 (1989); and de Jong, P. J. et al.: *Proc. Natl. Acad. Sci. USA*, 85:3499–3503 (1988).

Mouse aprt has been extensively studied. The APRT gene in mice is a ubiquitous, constitutively expressed gene whose expression or lack of expression constitutes a sensitive selectable marker. See, for example, Tischfield, J. A. et al.: *Mol. Cell. Biol.*, 2:250–257 (1982). The mouse APRT gene has been characterized at the molecular level. The gene has been mapped to chromosome 8, Kozak, C. E. et al.: *Somat. Cell Genet.*, 1:371–382 (1975), Nesterova, T. B. et al.: *Biochem. Gent.*, 25:563–568 (1987), and has five exons and four introns preceded by four SP1 binding sites. See, for example, Dush, M. K. et al.: *Nucleic Acids Res.*, 16:8509–8524 (1988). The small size of the gene (less than 3.0 kb) in mice is believed to facilitate rapid localization and analysis of mutations and makes it particularly amenable to the construction of specific sequence alterations. At the amino acid level, mouse and human aprt are greater than 80% homologous, with most substitutions being conservative. See, for example, Broderick, T. P. et al.: *Proc. Natl. Acad. Sci. USA*, 84:3349–3353 (1987). This suggests that comparable mutations in the mouse and human genes may alter gene or enzyme function in a similar manner. An APRT-deficient mouse may be developed in accordance with this and the following Example as well as with this invention through the use of gene targeting in mouse embryonic stem cells. Such a mouse is believed to be suitable to aid in the study of the in vivo regulation, function and structure of the APRT gene, the fate mapping of cells, and selective ablation of cells, and provide a unique system for whole-animal studies of mutagenesis.

An APRT-deficient mouse can be produced by introducing into cultured animal embryonic stem cells (ES cells), a gene targeting vector containing a promoterless bacterial neomycin phosphotransferase (neo) gene flanked by mouse aprt sequences. See FIGS. 1 and 2. Homologous recombination will produce rare ES cells with the NEO gene precisely placed into an exon of one allele of aprt, thus rendering it nonfunctional. See FIGS. 1—2. These targeted ES cells will be selected and injected into appropriate mouse blastocysts to produce chimeric animals, some of which are likely to have ES cell-derived germ cells. See FIG. 3. When bred with wild-type, the latter animals will be identified by their ability to produce heterozygous offspring, which can then be inbred to produce homozygous, APRT-deficient mice. See FIG. 3.

A. ES and D3 Cell Cultures

An E14 or D3 cell line of male (XY) ES cells, which are derived from 129/Sv mice, can be targeted. An early passage of the cells was provided by Dr. Thomas Doetschman, College of Medicine, University of Cincinnati, Cincinnati, Ohio. Mice produced from these cells exhibit chinchilla coat color ($c^{ch}$), white-bellied agouti coloration ($A^\varrho$), pink-eyed dilution (p), and homozygosity for the glucose phosphate isomerase $I^a$ (GPI-$I^a$) isozyme. About 80% of the pups resulting from the injection of these cells into host blastocysts are noted to be chimeric, and germline transmission of a modified E14 or D3 ES cell genome has been reported. The E14 and D3 cells can be grown on mitotically arrested feeder layers to promote euploidy and maintain totipotency, or on medium conditioned by Buffalo rat liver cells or medium containing leukemia inhibitory factor (LIF) to accomplish the same ends.

B. Mutating the ES Cell APRT Gene by Disruption with Neo

A procedure for disrupting the APRT gene by homologous recombination, and for selection of the resulting recombinant cells, is described by Doetschman et al., *Proc. Natl. Acad. Sci. USA*, 8583–8587 (1988), and is generally applicable to ES cells. APRT activity levels are believed to vary only several-fold in rodent tissues and are high in ES cells. The strategy takes advantage of the observation that a promoterless NEO gene is expressed when introduced into an exon downstream from an active promoter. Thus, when introduced by homologous recombination, downstream from the endogenous aprt promoter, neo will confer G418 resistance to ES cells. Experience suggests that the number of illegitimate neo insertions conferring G418 resistance will be reduced since few will be downstream from active promoters.

Figure 1:
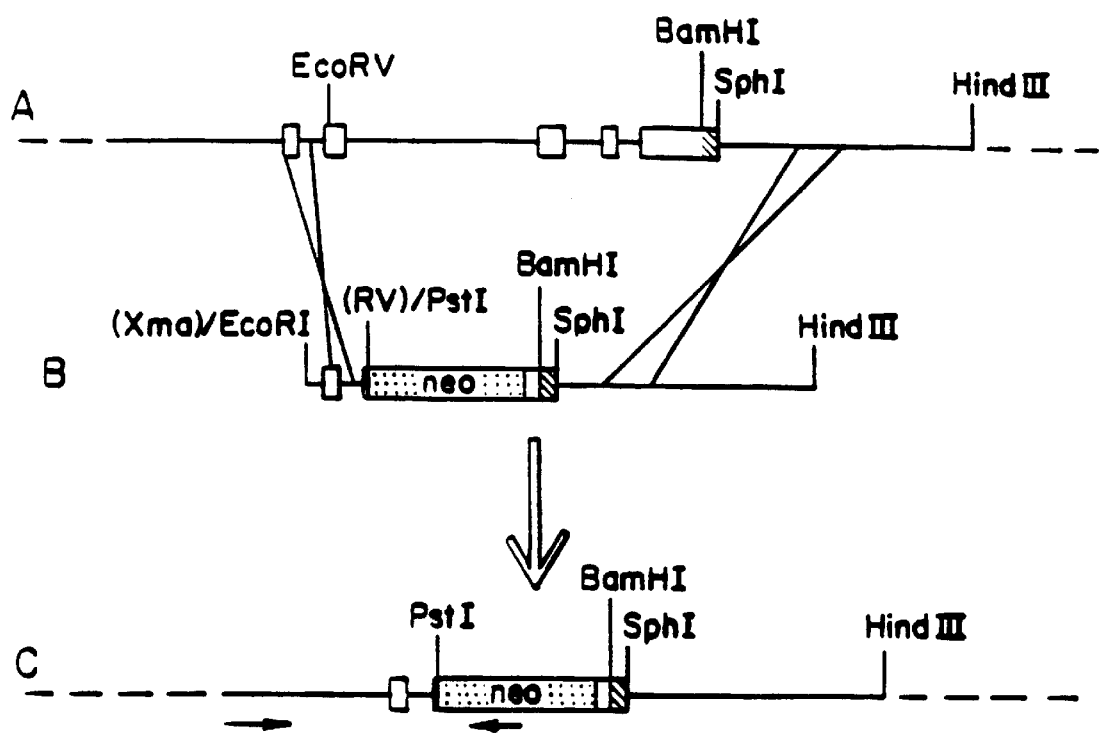
FIG. 1A depicts a scheme of resident mouse APRT gene. Open boxes represent exons, diagonal stripes represent 3' untranslated region, and the BamH1 site is within the 3' untranslated region.
FIG. 1B depicts the structure of a promoterless targeting construct of the present invention.
FIG. 1C depicts the organization of the targeted APRT gene after recombination with targeting DNA wherein the arrows indicate location of primers for diagnostic polymerase chain reaction (PCR) amplification. The predicted structure of the modified resident APRT gene is illustrated in this FIG. 1C.

One targeting vector is described below in Table II and illustrated in FIG. 1. A pSAM-4.4 plasmid, which contains the entire wild-type mouse APRT sequence including the promoter and about 1.3 kb of 3' flanking sequence, is selected as the starting plasmid. The 1.3 kb of 3' flanking sequence begins at nucleotide 3071 and ends at nucleotide 4358. See Table II. The underscored regions in Table II represent the exons. The bracketed region in Table II is the 3' untranslated region, i.e., nucleotides 2819–3070. The APRT translation start codon is at nucleotides 877–879.
SEQ ID NO:2:

Table II

```
   1 GAATTCATGC TCACGGGCTC ACAGGAAGGT CCAAGAAGGA
  41 ATGTTTAGAA TCCATTGGAC CCTCCCCACA CCCTCTCCTT
  81 TGATGGAGCA TGGGCCAATT TGGAGGATAT CTTTTGAGTA
 121 ATTGCAACTG CACTGAAGAT GATAATGGCC ATTATACTCA
 161 GAGGACAGTC TTTCCACACC ACTACCTATA GACCCAAGTA
 201 CTGTGCTGGG AAGGTAGAAC CCCAGTTCTG TCTCTGGCTA
 241 TCAGGACCTT CTGGTTCCAC CCCAAAACGA GGAGGGCACA
 281 TTCTGTTGCA ATGCACAGGA GTGTCTGTGG TCTCAGAGAA
 321 GGCATTCCTT ACCCGCCCTG CTACCCTGCT TTCCCCTGCG
 361 CTCTAGCCCA CACACAGTGC ACTCCACCT CTGGACCTAA
 401 GACTATCCAT CAGCTCCCTT CCGGGCTAAT TCCAGGAAAG
 441 CAGGGGCTGA ATCTCAGGCC CCTTGTACTA TGCGCGAGGG
 481 AAGGAACGCA AGGCCAAACC ACTCCAGCGG ACCTGGGCAA
 521 GACCCGTCCC TGCTCCCCCA GGTCCAGAAG ACTAGCCCCT
 561 GGAAAAGCAG GACTGAAAAA GCGTGTGTGG GGCAAAACCA
 601 AAAAAGGATG GACATCGCAC ATCCCCTTTC CACCCATATA
```

Table II-continued

```
 641 TCTTTGAGGT AGGGATGCTT GTGTTTAGGC AGCTCAAGAA
 681 ATCTAACCCC TGACTCAGGC CCCACACACA CCTCGCAGAG
 721 GCCCCGCCTC TCAGCCTGTC CCGCCCCTCG TGCTAGACCA
 761 ACCCGCACCC AGAAGCCCCG CCCATCGAGG ACGCTCCGCC
 801 CTTGTTCCCC CCGGGATTGA CGTGAGTTTA GCGTGCTGAT
 841 ACCTACCTCC TCCCTGCCTC CTACACGCAC GCGGCCATGT
 881 CGGAACCTGAGTTGAAACTGGTGGCGCGGCGCATCCGCGT
 921 CTTCCCCGACTTCCCAATCCCGGGCGTGCTGTTCAGGTGC
 961 GGTCACGAGC CGGCGAGGCG TTGGCGCTGT ACGCTCATCC
1001 CCCGGCGCAG GCGGTAGGCA GCCTCGGGGA TCTTGCGGGG
1041 CCTCTGCCCG GCCACACGCG GGTCACTCTC CTGTCCTTGT
1081 TCCTAGGGATATCTCGCCCCTCTTGAAAGACCCGGACTCC
1121 TTCCGAGCTTCCATCCGCCTCTTGGCCAGTCACCTGAAGT
1161 CCACGCACAGCGGCAAGATCGACTACATCGCAGGCGAGTG
1201 GCCTTGCTAG GTCGTGCTCG TCCCCCACGG TCCTAGCCCC
1241 TATCCCCTTT CCCCCTCGTG TCACCCACAG TCTGCCCCAC
1281 ACCCATCCAT TCTTCTTCGA CCTCTGACAC TTCCTCCTTG
1321 GTTCCTCACT GCCTTGGACG CTTGTTCACC CTGGATGAAC
1361 TATGTAGGAG TCTCCCTTCC CTGCTAGGTA CCCTAAGGCA
1401 TCTGCCCTCG GTGCTTGTTC CTAGAGACGA ACTCTGCTCT
1441 GTCCTTGTGT CCAGAACCAG GCCTCCCTCT TTTAGGGCAC
1481 AAAGCTGGCC AGCATCCTGA CAGCAGGCTG GGAGACCCTG
1521 GAACCTCCAG ATGACGGACA TCCTTGCTTA GGGGTAGCCT
1561 CTGGGATGAA CTAGATACTA AAAATTAGGT AACCTTGGTT
1601 GGGCGTGGCG TGCCTGGGCA GACCTCAAGC CTGGTAGCTT
1641 CAGGGGCTGT TTCTCCCCAG GACTACACCG GGGCATCTTT
1681 CTCTTGTTCC CTCACACAAG CTTGTGTTAA ACAACTGCTG
1721 TCTACTTGGC TCCATGCCTG AGCTTGAGAA ACACCCTAGG
1761 ACAGCTGAAT GTCCACCAGG AGTGTCCAGA GGGAGGGTGG
1801 GCACCCCAGA GAACAGAGTG GCCTTGGTAA GTGCTCGGGG
1841 ACCACAGACT TTGCCACTTC ACTTCCTATT GGTACCCTTG
1881 GCCATGCTCC AGAAATTAGG GCATGTATGT ATCCTTCCCA
1921 CGACAGCTAG ATGCTGCATT TGAAGGTGGC AAGACCACCA
1961 TAGGTGGCCC TGAGCTGTTC AGAAGGCAGG TAGGATCCCC
2001 AAGGCTGAGA TGATGAGTTG ATGGCTACCC AGTAGCCATC
2041 AACGTTCTTC TAACCGTAGT CAGCAAGACC TAGTGTTCCT
2081 AGCAAGTGTT GACCTCGCCC ATACTTGGCC TCTAGATTCC
2121 CATGCCCCTC AGCTCCATCC CACAACCTTC CCTCCTTACC
2161 CTAACAGGTCTAGACTCCAGGGGCTTCCTGTTTGGCCCTT
```

Table II-continued

2201 CCCTAGCTCAGGAGCTGGGCGTGGGCTGTGTGCTCATCCG
2241 GAAACAGGGGAAGCTGCCGGGCCCCACTGTGTCAGCCTCC
2281 TATTCTCTGGAGTATGGGAAGGTAAGCGAG CTGTGTGTAG
2321 AGGAAGGGCA GGGTCTTATC ACGGCTACCA GTGTCTAGGA
2361 GTAAATGTGG GTGCTCAGAG AGGTTGAGAC ATTGGGTCAG
2401 GTTTACACCA CCCAGAAACG CTCGAGCCTA GGGAGGTGGC
2441 CACTTGTTCG CGCCTAGACT CTGTCTTACA CTACTTCCTG
2481 TCTGCAGGCTGAGCTGGAAATCCAGAAAGATGCCTTGGAA
2521 CCCGGGCAGAGAGTGGTCATTGTGGATGACCTCCTGGCCA
2561 CAGGAGGTAA AGAACCAACC CAAGACAAAC AGACTTCAAA
2601 GGGCCAGACC CTGTCCTGGG TGCTGACTAA GCAAAGAGCT
2641 TGAACACCTC CTCTTTCTCT GTCCCTTCCC CCCAGGAACC
2681 ATGTTTGCGGCCTGTGACCTGCTGCACCAGCTCCGGGCTG
2721 AAGTGGTGGA GTGTGTGAGC CTGGTGGAGC TGACCTCGCT
2761 GAAGGGCAGGGAGAGGCTAGGACCTATACCATTCTTCTCT
2801 CTCCTCCAGTATGACTGA[GG AGCTGGCTAG ATGGTCACAC
2841 CCCTGCTCCC AGCAGCACTA GGAACTGCTT GGTGGCTCAG
2881 CCTAGGCGCC TAAGTGACCT TTGTGAGCTA CCGGCCGCCC
2921 TTTTGTGAGT GTTATCACTC ATTCCTTTGG TCAGCTGATC
2961 CGCCGTGCCT GTGGACCCCT GGATCCTTGT ACTTTGTACA
3001 CGTCCCACAC ACCCTGGAGC ATAGCAGAGC TGTGCTACTG
3041 GAGATCAATA AACCGTTTTG ATATGCATGC]CTGCTTCTCC
3081 TCAGTTTGTT GCATGGGTCA CATTCCAGGC CTCCAGAGCG
3121 ATACTACAGG GACAAGGGGG CTCAGGTGGG AACCCATAGG
3161 CTCAGCTTTG TATTGAAGCC ACAACCCCTA CTAGGGAGCA
3201 GATGTTATCT CTGTCAGTCT CTGAGGCAGC TGACTACATA
3241 AACAGGTTTA TTGCTTCACT GTTCTAGGCC TGTTATTCCA
3281 TTAGGATGGA CGAGGATGAA GCAGTGACCC ACAGCCACTA
3321 TMTTTTTTTC TGTTGTTTGT CGAGATGGGG TTTCTTAATA
3361 TAACCAGCCC TGGCTATTCT GGACTTGATT TGTAGCCCAG
3401 GCTGGCCTCA AACTTAAGAG GTCCACTGCC TCTGCTTCTT
3441 GAGTGCTGGG ATCAAAGTAC GCACCGCAAC ACCCAGTTCA
3481 CAGTCACTAT CTCAAAAAAG CTATTTTGTT GCAGGGCATG
3521 GTGTATAGAC CTTTAATCCT AGTGCCTTGA AGGTAGGCAG
3561 GCTGTTAAAA TTCAAGGCCA ACCTGGCTAT ATAGTTCCAA
3601 GGAGAGCCAG AGCTTTTAGA AAAAATAAAA ATTTAAAAAA
3641 TATATATCAA GCCAGGCATG GTGGCACACA CCTTTGATCC
3681 CAGCACTTGG GAGGCAGAGG CAGGGCGGAT TTCTGATCTA
3721 CAGAATGAGT TCCAGGACAA CCAGTTCTAC AGAGAAACCC
3761 TGTCTCAAAA AAAAAAAAAA AATCACATTC TGGGGAAGTG

Table II-continued

3801 GGTGTTGGGG AAAGAGGGGG ATGGGAGAGA GCCTGCGTCC
3841 CACCAGAGTT CTGGTGCTCC AGGAGGCTGG ATACTTTTCA
3881 CACTGCCCCA GTGTGAGGCT ATCTGGCATG ATGTTAAGCC
3921 AGTCTCCGGC ACCCCACACT GGATATGGTG GAGGAGCTGA
3961 GAACATAATA GGGACCCGGG CAGAAGGAAA GAGAGGGGGG
4001 GGAAGGGAGG GGTGCTGGGT GGAGTCCTTA GTCTGGTCCA
4041 TGGCTGCAGC GTAGGAAGCC TTCTGGCAGG TTAAAAGTGC
4081 TCATTAGGAG AGCCTATCCG ATCATCATTC AAACACGGTG
4121 GGCCTTCATG ATCAGAGACA GTCTATGGTT TTAGAGCTTT
4161 ATTGTAGAAA GGGAAGGAGA AAGAGAAGGT AGAAGGACAG
4201 CCATGGCCAC GTGGAGAGAG GGGGGAAGGG AAACACAAAA
4241 AAACCCAGAG AGCTTAAGAG AGCGAGGAGG GGCCAAACAT
4281 CCCCTTATAG TGGGCTTTGC CATCTTGCTG TTGCTAGGTA
4321 ACTGTGGGAA GGGAGTCTAG CCAGAATGCC AGAAGCTT

A 1 kb BglII/AvaI fragment containing the promoterless NEO gene is cut from a pSV2NEO, blunt-ended, and ligated into a unique BspEI site located in exon 3 of mouse aprt in pSAM-4.4 (Table II), thus inactivating aprt by introduction. See Table III. Exons 1–3 in the sequence in Table III are at nucleotides 873–952 and 1083–1189 and 2164–3306, respectively. Exons 4 and 5 are at nucleotides 3493–3571 and 3681–3823, respectively.

The translation start codon for the APRT gene in this sequence in Table III is at nucleotides 873–875, where the APRT translation start codon for pSAM-4.4 is at nucleotides 877–879. The stop codon for this APRT gene is at nucleotides 3821–3823. While exon 3 includes nucleotides 2164–3306, it has been altered from the wild-type APRT exon 3 by the insertion of a NEO gene. The NEO gene insert includes nucleotides 2238–3247 and is in a different reading frame from the wild-type APRT exon 3. In other words, the NEO gene relies upon an internal translation start codon at nucleotides 2273–2275 in exon 3. The stop codon for the NEO gene is at nucleotides 3065–3067. Included within the neo insert is an untranslated 3' DNA fragment downstream from the neo stop codon, 3065–3067. This untranslated 3' DNA downstream fragment terminates at nucleotide 3247. The polyadenylation signal, AATAAA, is located at nucleotides 4052–4057. While the DNA sequences of exons 4 and 5 are the same as the normally occurring exons 4 and 5, they are not translated because of the stop codon at nucleotides 3065–3067 for the NEO gene.

The construct recited in TABLE III encodes for at least two proteins. The DNA sequences encoding aprt and neo are out of frame with respect to one another so that what is translated is either a protein comprising a portion of aprt and a 12 amino acid nonsense polypeptide which is a translation product of the DNA segment that precedes the neo start codon at 2273–2275, or the NEO protein which begins at the internal translation start codon at nucleotides 2273–2275 and ends at the stop codon at nucleotides 3065–3067.

While there are minor differences in the upstream sequences from the APRT initiation codons between the sequences recited in Tables I and III, the differences are believed to have no impact upon the function of these fragments in accordance with the present invention. The differences are believed to be attributable to possible errors in transcription from the sequencing gels to recordation in the computer.

SEQ ID NO: 3:

TABLE III

```
             10         20         30         40         50
  GAATTCATGCTCACGGGCTCACAGGAAGGTCCAAGAAGGAATGTTTAGAA
1
2
3
             60         70         80         90        100
  TCCATTGGACCCTCCCCACACCCTCTCCTTTGATGGAGCATGGGCCAATT
1
2
3
            110        120        130        140        150
  TGGAGGATATCTTTTGAGTAATTGCAACTGCACTGAAGATGATAATGGCC
1
2
3
            160        170        180        190        200
  ATTATACTCAGAGGACAGTCTTTCCACACCACTACCTATAGACCCAAGTA
1
2
3
            210        220        230        240        250
  CTGTGCTGGGAAGGTAGAACCCCAGTTCTGTCTCTGGCTATCAGGACCTT
1
2
3
            260        270        280        290        300
  CTGGTTCCACCCCAAAACGAGGAGGGCACATTCTGTTGCAATGCACAGGA
1
2
3
            310        320        330        340        350
  GTGTCTGTGGTCTCAGAGAAGGCATTCCTTACCCGCCCTGCTACCCTGCT
1
2
3
            360        370        380        390        400
  TTCCCCTGCGCTCTAGCCCACACACAGTGCACTCCCACCTCTGGACCTAG
1
2
3
            410        420        430        440        450
  ACTATCCATCAGCTCCCTTCCGGTAATTTCAGGAAAGCAGGGGCTGAATC
1
2
3
            460        470        480        490        500
  TCAGGCCCTTGTACTATGCGCGAGGGAAGGAACGCAAGGCCAAACCACTC
1
2
3
            510        520        530        540        550
  CAGCGGACCTGGGCAAGACCCGTCCCTGCTCCCCCAGGTCCAGAAGACTA
1
2
3
            560        570        580        590        600
  GCCCCTGGAAAAGCAGGACTGAAAAAGCGTGTGTGGGGCAAAACCAAAAA
1
2
3
```

TABLE III-continued

```
            610        620        630        640        650
  AGGATGGACATCGCACATCCCCTTTCCACCCATATATCTTTGAGGTAGGG
1
2
3
            660        670        680        690        700
  ATGCTTGTGTTTAGGCAGCTCAAGAAATCTAACCCCTGACTCAGGCCCCA
1
2
3
            710        720        730        740        750
  CACACACCTCGCAGAGGCCCCGCCTCTCAGCCTGTCCCGCCCCTCGTGCT
1
2
3
            760        770        780        790        800
  AGACCAACCCGCACCCAGAAGCCCCGCCCATCGAGGACGCTCCGCCCTTG
1
2
3
            810        820        830        840        850
  TTCCCCCCGGGATTGACGTGAGTTTAGCGTGCTGATACCTACCTCCTCCC
1
2
3
            860        870        880        890        900
  TGCCTCCTACACGCACGCGGCCATGTCGGAACCTGAGTTGAAACTGGTGG
1
2
3               M   S   E   P   E   L   K   L   V
            910        920        930        940        950
  CGCGGCGCATCCGCGTCTTCCCCGACTTCCCAATCCCGGGCGTGCTGTTC
1
2
3 A   R   R   I   R   V   F   P   D   P   P   I   P   G   V   L   P
            960        970        980        990       1000
  AGGTGCGGTCACGAGCCGGCGAGGCGTTGGCGCTGTACGCTCATCCCCCG
1
2
3 R
           1010       1020       1030       1040       1050
  GCGCAGGCGGTAGGCAGCCTCGGGGATCTTGCGGGGCCTCTGCCCGGCCA
1
2
3
           1060       1070       1080       1090       1100
  CACGCGGGTCACTCTCCTGTCCTTGTTCCTAGGGATATCTCGCCCCTCTT
1
2                                    I   S   P   L   L
3
           1110       1120       1130       1140       1150
  GAAAGACCCGGACTCCTTCCGAGCTTCCATCCGCCTCTTGGCCAGTCACC
1 K   D   P   D   S   F   R   A   S   I   R   L   L   A   S   H
2
3
           1160       1170       1180       1190       1200
  TGAAGTCCACGCACAGCGGCAAGATCGACTACATCGCAGGCGAGTGGCCT
  L   K   S   T   H   S   G   K   I   D   Y   I   A
2
3
           1210       1220       1230       1240       1250
  TGCTAGGTCGTGCTCGTCCCCCACGGTCCTAGCCCCTATCCCCTTTCCCC
1
2
3
           1260       1270       1280       1290       1300
```

TABLE III-continued

```
CTCGTGTCACCCACAGTCTGCCCCACACCCATCCATTCTTCTTCGACCTC
1
2
3
         1310      1320      1330      1340      1350
TGACACTTCCTCCTTGGTTCCTCACTGCCTTGGACGCTTGTTCACCCTGG
1
2
3
         1360      1370      1380      1390      1400
ATGAACTATGTAGGAGTCTCCCTTCCCTGCTAGGTACCCTAAGGCATCTG
1
2
3
         1410      1420      1430      1440      1450
CTCGGTGCTTGTTCCTAGAGACGAACTCTGCTCTGTCCTTGTGTCCAGCC
1
2
3
         1460      1470      1480      1490      1500
AACCAGGCCTCCCTCTTTTAGGGCACAAAGCTGGCCAGCATCCTGACAGC
1
2
3
         1510      1520      1530      1540      1550
AGGCTGGGAGACCCTGGAACCTCCAGATGACGGACATCCTTGCTTAGGGG
1
2
3
         1560      1570      1580      1590      1600
TAGCCTCTGGGATGAACTAGATACTAAAAATTAGGTAACCTTGGTTGGGC
1
2
3
         1610      1620      1630      1640      1650
GTGGCGTGCCTGGGCAGACCTCAAGCCTGGTAGCTTCAGGGGCTGTTTCT
1
2
3
         1660      1670      1680      1690      1700
CCCCAGGACTACACCGGGGCATCTTTCTCTTGTTCCCTCACACAAGCTTG
1
2
3
         1710      1720      1730      1740      1750
TGTTAAACAACTGCTGTCTACTTGGCTCCATGCCTGAGCTTGAGAAACAC
1
2
3
         1760      1770      1780      1790      1800
CCTAGGACAGCTGAATGTCCACCAGGAGTGTCCAGAGGGAGGGTGGGCAC
1
2
3
         1810      1820      1830      1840      1850
CCCAGAGAACAGAGTGGCCTTGGTAAGTGCTCGGGGACCACAGACTTTGC
1
2
3
         1860      1870      1880      1890      1900
CACTTCACTTCCTATTGGTACCCTTGGCCATGCTCCAGAAATTAGGGCAT
1
2
3
         1910      1920      1930      1940      1950
GTATGTATCCTTCCCACGACAGCTAGATGCTGCATTTGAAGGTGGCAAGA
1
2
3
         1960      1970      1980      1990      2000
CCACCATAGGTGGCCCTGAGCTGTTCAGAAGGCAGGTAGGATCCCCAAGG
1
2
3
         2010      2020      2030      2040      2050
CTGAGATGATGAGTTGATGGCTACCCAGTAGCCATCAACGTTCTTCTAAC
1
2
3
         2060      2070      2080      2090      2100
CGTAGTCAGCAAGACCTAGTGTTCCTAGCAAGTGTTGACCTCGCCCATAC
1
2
3
         2110      2120      2130      2140      2150
TTGGCCTCTAGATTCCCATGCCCCTCAGCTCCATCCCACAACCTTCCCTC
1
2
3
         2160      2170      2180      2190      2200
CTTACCCTAACAGGTCTAGACTCCAGGGGCTTCCTGTTTGGCCCTTCCCT
1
2        G  L  D  S  R  G  F  L  F  G  P  S  L
3
         2210      220       2230      2240      2250
AGCTCAGGAGCTGGGCGTGGGCTGTGTGCTCATCCGGGATCTGATCAAGA
1
2
3 A  Q  E  L  G  V  G  C  V  L  I  R [D  L  I  K
         2260      2270      2280      2290      2300
GACAGGATGAGGATCGTTTCGCATGATTGAACAAGATGGATTGCACGCAG
1
2                         M  I  E  Q  D  G  L  H  A
R  Q  D  E  D  R  F  A  U]
         2310      2320      2330      2340      2350
GTTCTCCGGCCGCTTGGGTGGAGAGGCTATTCGGCTATGACTGGGCACAA
1
G  S  P  A  A  W  V  E  R  L  F  G  Y  D  W  A  Q
3
         2360      2370      2360      2390      2400
CAGACAATCGGCTGCTCTGATGCCGCCGTGTTCCGGCTGTCAGCGCAGGG
1
2Q  T  I  G  C  S  D  A  A  V  F  R  L  S  A  Q  G
3
         2410      2420      2430      2440      2450
GCGCCCGGTTCTTTTTGTCAAGACCGACCTGTCCGGTGCCCTGAATGAAC
1
2R  P  V  L  F  V  K  T  D  L  S  G  A  L  N  E
3
         2460      2470      2480      2490      2500
TGCAGGACGAGGCAGCGCGGCTATCGTGGCTGGCCACGACGGGCGTTCCT
1
L  Q  D  E  A  A  R  L  S  W  L  A  T  T  G  V  P
3
         2510      2520      2530      2540      2550
TGCGCAGCTGTGCTCGACGTTGTCACTGAAGCGGGAAGGGACTGGCTGCT
1
2C  A  A  V  L  D  V  V  T  E  A  G  R  D  W  L  L
3
         2560      2570      2580      2590      2600
ATTGGGCGAAGTGCCGGGGCAGGATCTCCTGTCATCTCACCTTGCTCCTG
1
```

TABLE III-continued

```
           2610      2620      3630      2640      2650
         CCGAGAAAGTATCCATCATGGCTGATGCAATGCGGCGGCTGCATACGCTT
1
2 L  G  E  V  P  G  Q  D  L  L  S  S  H  L  A  P
3
         A  E  K  V  S  I  M  A  D  A  M  R  R  L  H  T  L 2660      2670      2680      2690      2700
         GATCCGGCTACCTGCCCATTCGACCACCAAGCGAAACATCGCATCGAGCG
1
2 D  P  A  T  C  P  F  D  H  Q  A  K  H  R  I  E  R
3

2710      2720      2730      2740      2750
         AGCACGTACTCGGATGGAAGCCGGTCTTGTCGATCAGGATGATCTGGACG
1
2 A  R  T  R  M  E  A  G  L  V  D  Q  D  D  L  D
3

2760      2770      2780      2790      2800
         AAGAGCATCAGGGGCTCGCGCCAGCCGAACTGTTCGCCAGGCTCAAGGCG
1
  E  E  H  Q  G  L  A  P  A  E  L  F  A  R  L  K  A
3

2810      2820      2830      2840      2850
         CGCATGCCCGACGGCGAGGATCTCGTCGTGACCCATGGCGATGCCTGCTT
1
2 R  M  P  D  G  E  D  L  V  V  T  H  G  D  A  C  L
3

2860      2870      2880      2890      2900
         GCCGAATATCATGGTGGAAAATGGCCGCTTTTCTGGATTCATCGACTGTG
1
2 P  N  I  M  V  E  N  G  R  F  S  G  F  I  D  C
3

2910      2920      2930      2940      2950
         GCCGGCTGGGTGTGGCGGACCGCTATCAGGACATAGCGTTGGCTACCCGT
1
  G  R  L  G  V  A  D  R  Y  Q  D  I  A  L  A  T  R
3

2960      2970      2980      2990      3000
         GATATTGCTGAAGAGCTTGGCGGCGAATGGGCTGACCGCTTCCTCGTGCT
1
2 D  I  A  E  E  L  G  G  E  W  A  D  R  F  L  V  L
3

3010      3020      3030      3040      3050
         TTACGGTATCGCCGCTCCCGATTCGCAGCGCATCGCCTTCTATCGCCTTC
1
2 Y  G  I  A  A  P  D  5  Q  R  I  A  F  Y  R  L
3

3060      3070      3080      3090      3100
         TTGACGAGTTCTTCTGAGCGGGACTCTGGGGTTCGAAATGACCGACCAAG
1
  L  D  E  F  F  U
3

3110      3120      3130      3140      3150
         CGACGCCCAACCTGCCATCACGAGATTTCGATTCCACCGCCGCCTTCTAT
1
2
3

3160      3170      3180      3190      3200
         GAAAGGTTGGGCTTCGGAATCGTTTTCCGGGACGCCGGCTGGATGATCCT
1
2
3

3210      3220      3230      3240      3250
         CCAGCGCGGGGATCTCATGCTGGAGTTCTTCGCCCACCCCGGCCGGAAAC
1                                                    K
2
```

TABLE III-continued

```
           3260      3270      3280      3290      3300
         AGGGGAAGCTGCCGGGCCCCACTGTGTCAGCCTCCTATTCTCTGGAGTAT
1
  Q  G  K  L  P  G  T  V  S  A  S  Y  S  L  E  Y
2
3

3310      3320      3330      3340      3350
         GGGAAGGTAAGCGAGCTGTGTGTAGAGGAAGGGCAGGGTCTTATCACGGC
1G  K
2
3

3360      3370      3380      3390      3400
         TACCAGTGTCTAGGAGTAAATGTGGGTGCTCAGAGAGGTTGAGACATTGG
1
2
3

3410      3420      3430      3440      3450
         GTCAGGTTTACACCACCCAGAAACGCTCGAGCCTAGGGAGGTGGCCACTT
1
2
3

3460      3470      3480      3490      3500
         GTTCGCGCCTAGACTCTGTCTTACACTACTTCCTGTCTGCAGGCTAGCT
1                                                    A  E  L
2
3

3510      3520      3530      3540      3550
         GGAAATCCAGAAAGATGCCTTGGAACCCGGGCAGAGAGTGGTCATTGTGG
1 E  I  Q  K  D  A  L  E  P  G  Q  R  V  V  I  V
2
3

3560      3570      3580      3590      3600
         ATGACCTCCTGGCCACAGGAGGTAAAGAACCAACCCAAGACAAACAGACT
  D  D  L  L  A  T  G
2
3

3610      3620      3630      3640      3650
         TCAAAGGGCCAGACCCTGTCCTGGGTGCTGACTAAGCAAAGAGCTTGAAC
1
2
3

3660      3670      3680      3690      3700
         ACCTCCTCCTTCTCTGTCCCTTCCCCCCAGGAACCATGTTTGCGGCCTGT
1
2                                      G  T  M  F  A  A  C
3

3710      3720      3730      3740      3750
         GACCTGCTGCACCAGCTCCGGGCTGAAGTGGTGGAGTGTGTGAGCCTGGT
1
2 D  L  L  H  Q  L  R  A  E  V  V  E  C  V  S  L  V
3

3760      3770      3780      3790      3800
         GGAGCTGACCTCGCTGAAGGGCAGGGAGAGGCTAGGACCTATACCATTCT
1
2 E  L  T  S  L  K  G  R  E  R  L  G  P  I  P  F
3

3810      3820      3830      3840      3850
         TCTCTCTCCTCCAGTATGACTGAGGAGCTGGCTAGATGGTCACACCCCTG
1
  F  S  L  L  Q  Y  D  U
3

3860      3870      3880      3890      3900
         CTCCCAGCAGCACTAGGAACTGCTTGGTGGCTCAGCCTAGGCGCCTAAGT
1
2
3
```

TABLE III-continued

```
         3910      3920      3930      3940      3950
GACCTTTGTGAGCTACCGGCCGCCCTTTTGTGAGTGTTATCACTCATTCC
1
2
3
         3960      3970      3980      3990      4000
TTTGGTCAGCTGATCCGCCGTGCCTGTGGACCCCTGGATCCTTGTACTTT
1
2
3
         4010      4020      4030      4040      4050
GTACACGTGCCACACACCCTGGAGCATAGCAGAGCTGTGCTACTGGAGAT
1
2
3
         4060      4070      4080      4090      4100
CAATAAACCGTTTTGATATGCATGCCTGCTTCTCCTCAGTTTGTTGCATG
1
2
3
         4110      4120      4130      4140      4150
GGTCACATTCCAGGCCTCCAGAGCGATACTACAGGGACAAGGGGGCTCAG
1
2
3
         4160      4170      4180      4190      4200
GTGGGAACCCATAGGCTCAGCTTTGTATTGAAGCCACAACCCCTACTAGG
1
2
3
         4210      4220      4230      4240      4250
GAGCAGATGTTATCTCTGTCAGTCTCTGAGGCAGCTGACTACATAAACAG
1
2
3
         4260      4270      4280      4290      4300
GTTTATTGCTTCACTGTTCTAGGCCTGTTATTCCATTAGGATGGACGAGG
1
2
3
         4310      4320      4330      4340      4350
ATGAAGCAGTGACCCACAGCCACTATATTTTTTTCTGTTGTTTGTCGAGA
1
2
3
         4360      4370      4380      4390      4400
TGGGGTTTCTTAATATAACCAGCCCTGGCTATTCTGGACTTGATTTGTAG
1
2
3
         4410      4420      4430      4440      4450
CCCAGGCTGGCCTCAAACTTAAGAGGTCCACTGCCTCTGCTTCTTGAGTG
1
2
3
         4460      4470      4480      4490      4500
CTGGGATCAAAGTACGCACCGCAACACCCAGTTCACAGTCACTATCTCAA
1
2
3
         4510      4520      4530      4540      4550
AAAAGCTATTTTGTTGCAGGGCATGGTGTATAGACCTTTAATCCTAGTGC
1
2
3
```

TABLE III-continued

```
         4560      4570      4580      4590      4600
CTTGAAGGTAGGCAGGCTGTTAAAATTCAAGGCCAACCTGGCTATATAGT
1
2
3
         4610      4620      4630      4640      4650
TCCAAGGAGAGCCAGAGCTTTTAGAAAAAATAAAAATTTAAAAAATATAT
1
2
3
         4660      4670      4680      4690      4700
ATCAAGCCAGGCATGGTGGCACACACCTTTGATCCCAGCACTTGGGAGGC
1
2
3
         4710      4720      4730      4740      4750
AGAGGCAGGGCGGATTTCTGATCTACAGAATGAGTTCCAGGACAACCAGT
1
2
3
         4760      4770      4780      4790      4800
TCTACAGAGAAACCCTGTCTCAAAAAAAAAAAAAAAATCACATTCTGGGG
1
2
3
         4810      4820      4830      4840      4850
AAGTGGGTGTTGGGGAAAGAGGGGGATGGGAGAGAGCCTGCGTCCCACCA
1
2
3
         4860      4870      4880      4890      4900
GAGTTCTGGTGCTCCAGGAGGCTGGATACTTTTCACACTGCCCCAGTGTG
1
2
3
         4910      4920      4930      4940      4950
AGGCTATCTGGCATGATGTTAAGCCAGTCTCCGGCACCCCACACTGGATA
1
2
3
         4960      4970      4980      4990      5000
TGGTGGAGGAGCTGAGAACATAATAGGGACCCGGGCAGAAGGAAAGAGAG
1
2
3
         5010      5020      5030      5040      5050
GGGGGGGAAGGGAGGGGTGCTGGGTGGAGTCCTTAGTCTGGTCCATGGCT
1
2
3
         5060      5070      5080      5090      5100
GCAGCGTAGGAAGCCTTCTGGCAGGTTAAAAGTGCTCATTAGGAGAGCCT
1
2
3
         5110      5120      5130      5140      5150
ATCCGATCATCATTCAAACACGGTGGGCCTTCATGATCAGAGACAGTCTA
1
2
3
         5160      5170      5180      5190      5200
TGGTTTTAGAGCTTTATTGTAGAAAGGGAAGGAGAAAGAGAAGGTAGAAG
1
2
3
         5210      5220      5230      5240      5250
```

TABLE III-continued

```
GACAGCCATGGCCACGTGGAGAGAGGGGGGAAGGGAAAGAGAAAAAAAGC
1
2
3

5260      5270      5280      5290      5300
CAGAGAGCTTAAGAGAGCGAGGAGGGGCCAAACATCCCCTTATAGTGGGC
1
2
3

5310      5320      5330      5340      5350
TTTGCCATCTTGCTGTTGCTAGGTAACTGTGGGAAGGGAGTCTAGCCAGA
1
2
3

5360
ATGCCAGAAGCTT
1
2
3
```

The 4.3 kb fragment of Table III contains a complete mouse APRT gene disrupted in exon 3 by neo. It confers G418 resistance. BglI digestion of the plasmid containing the sequence recited in Table III releases an about 3.6 kb fragment containing the 1 kb NEO gene flanked at each end by about 1.3 kb of mouse genomic aprt sequences. See Table IV and line B of FIG. 2. The 1.3 kb aprt sequence at each end is believed to be sufficient to allow a high frequency of homologous recombination. This 3.6 kb fragment lacks the first exon of aprt as well as the promoter. Furthermore, both its 5' and 3' ends lie in noncoding regions. Thus, it is unlikely that small terminal deletions, that might occur as a consequence of recombination, will interfere with expression. This linear 3.6 kb fragment serves as an example of a targeting vector in accordance with the present invention (see below). When the fragment recited in line B of FIG. 2 and Table IV is introduced into ES cells and undergoes proper targeted homologous recombination with an endogenous APRT gene, it will produce a gene organization depicted in line C, FIG. 2. Thus, the consequence of correct targeting is the DNA illustrated in line C of FIG. 2.

TABLE IV

```
                 970       980       990      1000
                 GCCGGCGAGGCGTTGGCGCTGTACGCTCATCCCCCG
1
2
3

1010      1020      1030      1040      1050
GCGCAGGCGGTAGGCAGCCTCGGGGATCTTGCGGGGCCTCTGCCCGGCCA
1
2
3

1060      1070      1080      1090      1100
CACGCGGGTCACTCTCCTGTCCTTGTTCCTAGGGATATCTCGCCCCTCTT
1                                         I  S  P  L  L
2
3

1110      1120      1130      1140      1150
GAAAGACCCGGACTCCTTCCGAGCTTCCATCCGCCTCTTGGCCAGTCACC
1 K  D  P  D  S  F  R  A  S  I  R  L  L  A  S  H
2
3

1160      1170      1180      1190      1200
```

TABLE IV-continued

```
TGAAGTCCACGCACAGCGGCAAGATCGACTACATCGCAGGCGAGTGGCCT
  L  K  S  T  H  S  G  K  I  D  Y  I  A
2
3

1210      1220      1230      1240      1250
TGCTAGGTCGTGCTCGTCCCCCACGGTCCTAGCCCCTATCCCCTTTCCCC
1
2
3

1260      1270      1280      1290      1300
CTCGTGTCACCCACAGTCTGCCCCACACCCATCCATTCTTCTTCGACCTC
1
2
3

1310      1320      1330      1340      1350
TGACACTTCCTCCTTGGTTCCTCACTGCCTTGGACGCTTGTTCACCCTGG
1
2
3

1360      1370      1380      1390      1400
ATGAACTATGTAGGAGTCTCCCTTCCCTGCTAGGTACCCTAAGGCATCTG
1
2
3

1410      1420      1430      1440      1450
CCCTCGGTGCTTGTTCCTAGAGACGAACTCTGCTCTGTCCTTGTGTCCAG
1
2
3

1460      1470      1480      1490      1500
AACCAGGCCTCCCTCTTTTAGGGCACAAAGCTGGCCAGCATCCTGACAGC
1
2
3

1510      1520      1530      1540      1550
AGGCTGGGAGACCCTGGAACCTCCAGATGACGGACATCCTTGCTTAGGGG
1
2
3

1560      1570      1580      1590      1600
TAGCCTCTGGGATGAACTAGATACTAAAAATTAGGTAACCTTGGTTGGGC
1
2
3

1610      1620      1630      1640      1650
GTGGCGTGCCTGGGCAGACCTCAAGCCTGGTAGCTTCAGGGGCTGTTTCT
1
2
3

1660      1670      1680      1690      1700
CCCCAGGACTACACCGGGGCATCTTTCTCTTGTTCCCTCACACAAGCTTG
1
2
3

1710      1720      1730      1740      1750
TGTTAAACAACTGCTGTCTACTTGGCTCCATGCCTGAGCTTGAGAAACAC
1
2
3

1760      1770      1780      1790      1800
CCTAGGACAGCTGAATGTCCACCAGGAGTGTCCAGAGGGAGGGTGGGCAC
1
2
3

1810      1820      1830      1840      1850
CCCAGAGAACAGAGTGGCCTTGGTAAGTGCTCGGGGACCACAGACTTTGC
```

TABLE IV-continued

```
             1860       1870       1880       1890       1900
        CACTTCACTTCCTATTGGTACCCTTGGCCATGCTCCAGAAATTAGGGCAT 1910       1920       1930       1940       1950
        GTATGTATCCTTCCCACGACAGCTAGATGCTGCATTTGAAGGTGGCAAGA 1960       1970       1980       1990       2000
        CCACCATAGGTGGCCCTGAGCTGTTCAGAAGGCAGGTAGGATCCCCAAGG 2010       2020       2030       2040       2050
        CTGAGATGATGAGTTGATGGCTACCCAGTAGCCATCAACGTTCTTCTAAC 2060       2070       2080       2090       2100
        CGTAGTCAGCAAGACCTAGTGTTCCTAGCAAGTGTTGACCTCGCCCATAC 2110       2120       2130       2140       2150
        TTGGCCTCTAGATTCCCATGCCCCTCAGCTCCATCCCACAACCTTCCCTC 2160       2170       2180       2190       2200
        CTTACCCTAACAGGTCTAGACTCCAGGGGCTTCCTGTTTGGCCCTTCCCT
                      G  L  D  S  R  G  F  L  F  G  P  S  L
             2210       2220       2230       2240       2250
        AGCTCAGGAGCTGGGCGTGGGCTGTGTGCTCATCCGGGATCTGATCAAGA
         A  Q  E  L  G  V  G  C  V  L  I  R [D  L  I  K
             2260       2270       2280       2290       2300
        GACAGGATGAGGATCGTTTCGCATGATTGAACAAGATGGATTGCACGCAG
         R  Q  D  E  D  R  F  A  U]       M  I  E  Q  D  G  L  H  A
             2310       2320       2330       2340       2350
        GTTCTCCGGCCGCTTGGGTGGAGAGGCTATTCGGCTATGACTGGGCACAA
         G  S  P  A  A  W  V  E  R  L  F  G  Y  D  W  A  Q
             2360       2370       2380       2390       2400
        CAGACAATCGGCTGCTCTGATGCCGCCGTGTTCCGGCTGTCAGCGCAGGG
         Q  T  I  G  C  S  D  A  A  V  F  R  L  S  A  Q  G
             2410       2420       2430       2440       2450
        GCGCCCGGTTCTTTTTGTCAAGACCGACCTGTCCGGTGCCCTGAATGAAC
         R  P  V  L  F  V  K  T  D  L  S  G  A  L  N  E
             2460       2470       2480       2490       2500
        TGCAGGACGAGGCAGCGCGGCTATCGTGGCTGGCCACGACGGGCGTTCCT
         L  Q  D  E  A  A  R  L  S  W  L  A  T  T  G  V  P
             2510       2520       2530       2540       2550
        TGCGCAGCTGTGCTCGACGTTGTCACTGAAGCGGGAAGGGACTGGCTGCT
          A  A  V  L  D  V  V  T  E  A  G  R  D  W  L  L
             2560       2570       2580       2590       2600
        ATTGGGCGAAGTGCCGGGGCAGGATCTCCTGTCATCTCACCTTGCTCCTG
         L  G  E  V  P  G  Q  D  L  L  S  S  H  L  A  P
             2610       2620       2630       2640       2650
        CCGAGAAAGTATCCATCATGGCTGATGCAATGCGGCGGCTGCATACGCTT
         A  E  K  V  S  I  M  A  D  A  M  R  R  L  H  T  L
             2660       2670       2680       2690       2700
        GATCCGGCTACCTGCCCATTCGACCACCAAGCGAAACATCGCATCGAGCG
          D  P  A  T  C  P  F  D  H  Q  A  K  H  R  I  E  R
             2710       2720       2730       2740       2750
        AGCACGTACTCGGATGGAAGCCGGTCTTGTCGATCAGGATGATCTGGACG
         A  R  T  R  M  E  A  G  L  V  D  Q  D  D  L  D
             2760       2770       2780       2790       2800
        AAGAGCATCAGGGGCTCGCGCCAGCCGAACTGTTCGCCAGGCTCAAGGCG
         E  E  H  Q  G  L  A  P  A  E  L  F  A  R  L  K  A
             2810       2820       2830       2840       2850
        CGCATGCCCGACGGCGAGGATCTCGTCGTGACCCATGGCGATGCCTGCTT
          R  M  P  D  G  E  D  L  V  V  T  H  G  D  A  C  L
             2860       2870       2880       2890       2900
        GCCGAATATCATGGTGGAAAATGGCCGCTTTTCTGGATTCATCGACTGTG
          P  N  I  M  V  E  N  G  R  F  S  G  F  I  D  C
             2910       2920       2930       2940       2950
        GCCGGCTGGGTGTGGCGGACCGCTATCAGGACATAGCGTTGGCTACCCGT
         G  R  L  G  V  A  D  R  Y  Q  D  I  A  L  A  T  R
             2960       2970       2980       2990       3000
        GATATTGCTGAAGAGCTTGGCGGCGAATGGGCTGACCGCTTCCTCGTGCT
         D  I  A  E  E  L  G  G  E  W  A  D  R  F  L  V  L
             3010       3020       3030       3040       3050
        TTACGGTATCGCCGCTCCCGATTCGCAGCGCATCGCCTTCTATCGCTTC
          Y  G  I  A  A  P  D  S  Q  R  I  A  F  Y  R  L
             3060       3070       3080       3090       3100
        TTGACGAGTTCTTCTGAGCGGGACTCTGGGGTTCGAAATGACCGACCAAG
         L  A  E  F  F  U
             3110       3120       3130       3140       3150
        CGACGCCCAACCTGCCATCACGAGATTTCGATTCCACCGCCGCCTTCTAT
```

TABLE IV-continued

```
      3160      310      3180      3190      3200
GAAAGGTTGGGCTTCGGAATCGTTTTCCGGGACGCCGGCTGGATGATCCT
1
2
3

3210      3220      3230      3240      3250
CCAGCGCGGGGATCTCATGCTGGAGTTCTTCGCCCACCCCGGCCGGAAAC
1                                                K
2
3

3260      3270      3280      3290      3300
AGGGGAAGCTGCCGGGCCCCACTGTGTCAGCCTCCTATTCTCTGGAGTAT
  Q  G  K  L  P  G  P  T  V  S  A  S  Y  S  L  E  Y
2
3

3310      3320      3330      3340      3350
GGGAAGGTAAGCGAGCTGTGTGTAGAGGAAGGGCAGGGTCTTATCACGGC
1G K
2
3

3360      3370      3380      3390      3400
TACCAGTGTCTAGGAGTAAATGTGGGTGCTCAGAGAGGTTGAGACATTGG
1
2
3

3410      3420      3430      3440      3450
GTCAGGTTTACACCACCCAGAAACGCTCGAGCCTAGGGAGGTGGCCACTT
1
2
3

3460      3470      3480      3490      3500
GTTCGCGCCTAGACTCTGTCTTACACTACTTCCTGTCTGCAGGCTGAGCT
1                                              A  E  L
2
3

3510      3520      3530      3540      3550
GGAAATCCAGAAAGATGCCTTGGAACCCGGGCAGAGAGTGGTCATTGTGG
1E  I  Q  K  D  A  L  E  P  G  Q  R  V  V  I  V
2
3

3560      3570      3580      3590      3600
ATGACCTCCTGGCCACAGGAGGTAAAGAACCAACCCAAGACAAACAGACT
 D  D  L  L  A  T  G
2
3

3610      3620      3630      3640      3650
TCAAAGGGCCAGACCCTGTCCTGGGTGCTGACTAAGCAAAGAGCTTGAAC
1
2
3

3660      3670      3680      3690      3700
ACCTCCTCCTTCTCTGTCCCTTCCCCCAGGAACCATGTTTGCGGCCTGT
1
2                                G  T  M  F  A  A  C
3

3710      3720      3730      3740      3750
GACCTGCTGCACCAGCTCCGGGCTGAAGTGGTGGAGTGTGTGAGCCTGGT
2D  L  L  H  Q  L  R  A  E  V  V  E  C  V  S  L  V
3

3760      3770      3780      3790      3800
GGAGCTGACCTCGCTGAAGGGCAGGGAGAGGCTAGGACCTATACCATTCT
1
2E  L  T  S  L  K  G  R  E  R  L  G  P  I  P  F
3
```

TABLE IV-continued

```
      3810      3820      3830      3840      3850
TCTCTCTCCTCCAGTATGACTGAGGAGCTGGCTAGATGGTCACACCCCTG
1
 F  S  L  L  Q  Y  D  U
3

3860      3870      3880      3890      3900
CTCCCAGCAGCACTAGGAACTGCTTGGTGGCTCAGCCTAGGCGCCTAAGT
1
2
3

3910      3920      3930      3940      3950
GACCTTTGTGAGCTACCGGCCGCCCTTTTGTGAGTGTTATCACTCATTCC
1
2
3

3960      3970      3980      3990      4000
TTTGGTCAGCTGATCCGCCGTGCCTGTGGACCCCTGGATCCTTGTACTTT
1
2
3

4010      4020      4030      4040      4050
GTACACGTGCCACACACCCTGGAGCATAGCAGAGCTGTGCTACTGGAGAT
1
2
3

4060      4070      4080      4090      4100
CAATAAACCGTTTTGATATGCATGCCTGCTTCTCCTCAGTTTGTTGCATG
1
2
3

4110      4120      4130      4140      4150
GGTCACATTCCAGGCCTCCAGAGCGATACTACAGGGACAAGGGGCTCAG
1
2
3

4160      4170      4180      4190      4200
GTGGGAACCCATAGGCTCAGCTTTGTATTGAAGCCACAACCCCTACTAGG
1
2
3

4210      4220      4230      4240      4250
GAGCAGATGTTATCTCTGTCAGTCTCTGAGGCAGCTGACTACATAAACAG
1
2
3

4260      4270      4280      4290      4300
GTTTATTGCTTCACTGTTCTAGGCCTGTTATTCCATTAGGATGGACGAGG
1
2
3

4310      4320      4330      4340      4350
ATGAAGCAGTGACCCACAGCCACTATATTTTTTCTGTTGTTTGTCGAGA
1
2
3

4360      4370      4360      4390      4400
TGGGGTTTCTTAATATAACCAGCCCTGGCTATTCTGGACTTGATTTGTAG
1
2
3

4410      4420      4430      4440      4450
CCCAGGCTGGCCTCAAACTTAAGAGGTCCACTGCCTCTGCTTCTTGAGTG
1
2
3

4460      4470      4480      4490      4500
```

TABLE IV-continued

```
CTGGGATCAAAGTACGCACCGCAACACCCAGTTCACAGTCACTATCTCAA
1
2
3

4510       4520       4530       4540       4550
AAAAGCTATTTTGTTGCAGGGCATGGTGTATAGACCTTTAATCCTAGTGC
1
2
3

4560       4570       4580       4590
CTTGAAGGTAGGCAGGCTGTTAAAATTCAAGGCCAACCTGGC
1
2
3
```

C. ES Cell Targeting and Blastocyst Injection

The 3.6 kb linear fragment described above is introduced into E14 cells by electroporation under standard conditions. This is followed by selection in medium containing 150 micrograms per milliliter of G418. This level of G418 is believed to be effective in selecting ES cells containing a neo gene driven by the APRT promoter. It is believed that G418 resistant colonies will arise both from homologous recombination and illegitimate (nonhomologous) integration within any transcribing gene and that the former, normally a very rare event, will be enriched. To distinguish the former from the latter, DNA from pooled G418 resistant colonies will be tested for the presence of a unique fragment containing a predicted, novel junction created by homologous recombination. Cells from about 10 colonies are pooled and their extracted DNA subjected to PCR amplification with one oligonucleotide primer complementary to a 5'-region of the neo sequence and a second primer complementary to a sequence in the promoter of aprt, which is not present in the BglI fragment. See line C of FIG. 2. Only DNA pools containing the 1.5 kb aprtneo junctional fragment flanked by these primers will support amplification. Each cell colony that goes into the positive pool are tested to identify those that are properly targeted. Positive colonies are cryopreserved, and their putative 1.5 kb junctional fragments obtained after PCR amplification will be sequenced to confirm their identity and proper structure. Further, Southern blot analysis will confirm the presence of both a wild-type and a neo-disrupted aprt in the cells and will indicate the absence of any illegitimate insertion. Finally, to test for euploidy, high-resolution giemsa banded karyotypes are prepared.

Between 10 to 20 ES cells derived from several properly targeted clones are introduced into individual host blastocysts per the method of *Hogan* et al. In brief, 3.5-day p.c. blastocysts are individually held with a micropipette and slight negative pressure so that the inner cell mass is oriented towards the pipette orifice. An injection needle containing the ES cells is inserted into the blastocoele, the cells are expelled, and the needle is withdrawn. The injected blastocyst will then collapse but will subsequently expand after 2–3 hr. of culture. Injected blastocysts are suspended in drops of medium under oil at 37° C. and after expansion are transferred to the uterine horns of pseudopregnant females. See FIG. 3.

One endpoint of the present invention is to produce animals that have a genotype APRT$^+$/APRTNEO, APRT$^{Mx}$/APRT$^{Mx}$, APRT$^{Mx}$/APRT$^{My}$, APRT$^{My}$/APRT$^{My}$, APRTNEO/-, APRT$^{Mx}$/-, APRT$^{My}$/-, or APRTNEO/APRTNEO for purposes of in vivo mutagenesis and environmental monitoring. Alternatively, these animals can be used for purposes of cell fate mapping during development or malignancy and metastasis, or for selective cell ablation, or for measuring the effectiveness of enzyme therapy delivery vectors, or for measuring the effectiveness of enzyme therapy delivery vectors. In a first step, about $2.5 \times 10^7$ ES cells from the D3 or E14 ES cell lines are subjected to electroporation to introduce a linear, promotorless construct containing a selectable marker gene, such as an aprtneo construct described herein, into the cells to confer resistance and render the cells selectable. See FIG. 3. The disaggregated cells are suspended in PBS at about $10^7$ cells/ml. About 500 ul of cell suspension is introduced into the cuvette along with about 20 ug of the DNA dissolved in 50 ul of $H_2O$. After mixing gently, electroporation is carried out at about 21° F. and about 600V using a GeneZapper 450/2500 (IBI). For each experiment, 5 replicate cell samples are electroporated, bringing the total number of cells to about $2.5 \times 10^7$. Cells are added to 10 cm tissue culture plates with adherent, primary mouse embryo fibroblasts (MEFs) that are G418 resistant and that have been rendered non-mitotic by ionizing radiation (3000 rad), or treatment with mitomycin C. MEFs are prepared by removing the liver and heart of 15 to 17 day embryos that are transgenic for neo (neo transgenic mice available from Dr. Tom Doetschman, University of Cincinnati College of Medicine, Cincinnati, Ohio) disaggregating the remaining embryonic cells and expanding the cells in the presence of about 200 ug/ml G418. The MEFs are frozen and stored in liquid nitrogen until needed as feeder layers. The ES cells are maintained and selected on irradiated MEFs. Following electroporation with the aprtneo construct shown in FIG. 1, the ES cells are plated on irradiated MEFs in high glucose Dulbecco's Modified Eagles Medium (DMEM) 15% FB5, and after 24 hrs., G418 (150 ug/ml) is added to the medium. The medium, containing G418, is changed every second day until day 10, at which time G418 resistant ES cell colonies are visible. Several hundred colonies are picked with a glass pipette, and the cells in each colony disaggregated with trypsin and colonies individually placed in 15mm wells with MEF feeder layers.

The next step is to distinguish the cells that have incurred a desired targeted recombination event (FIG. 1) from the majority of transfected cells that have incurred a random integration event. To this end, aliquots of individual colonies are pooled into groups of ten, their DNAs isolated by standard methods and their purified DNA subjected to PCR analysis using a Cetus-Perkin Elmer DNA Thermal Cycler. The primers used are those described in FIG. 1, one located within the neo gene and contained within the introduced, targeting DNA and the other external to the targeting DNA and complementary to APRT 5' flanking DNA. Only those cells that have incurred a desired targeting event will have DNA sequences complementary to the primers sufficiently close to enable amplification of the intervening DNA. The PCR products are fractionated by gel electrophoresis and visualized by ethidium bromide staining. Pools producing positive signals are noted, and cells from individual colonies are similarly tested to identify the colony with the targeted APRT gene. Cells from the targeted colony are expanded, and DNA further tested by Southern blot analysis. The DNA is digested with BamHl, gel fractionated and blotted onto a nitrocellulose matrix, and hybridized with a $^{32}$P-labeled neo probe. If correctly targeted with no additional unwanted insertions, there is only a single hybridizing band of about 9 kb. For confirmation, the DNA is digested with HindIII and probed with a fragment extending from the XmaI site to the EcoRV site (FIG. 1). The wild-type gene produces a fragment of about 4 kb and the targeted gene produces a fragment of about 6 kb. The targeted ES cells are APRT$^+$/APRTNEO, and thus have only a single functional APRT gene. These cells can be used for a second targeting event to replace the functional APRT gene with a non-functional APRT gene bearing a known mutation (Mx), as described below. These ES cells will have an APRT$^{Mx}$/APRTNEO phenotype and will have an Aprt$^-$ genotype. Alternatively, the APRT$^+$/APRTNEO cells can be selected in DAP or FA directly for spontaneous, inactivating mutations in the remaining functional APRT gene, leading to an Aprt$^-$ phenotype (My) and the ability to grow in this medium. See FIG. 3. These cells would have an APRT$^{My}$/APRTNEO genotype and would also be aprt$^-$. The spontaneous mutation can be determined by, for example, PCR amplification followed by DNA sequencing using techniques well known to those versed in this art.

There are no available Aprt$^-$ mouse embryo fibroblasts available to serve as feeder layers for ES cells being selected in PAP or 2-FA. These can be produced from APRTNEO/APRTNEO or APRTNEO/APRY$^{Mx}$ or APRT$^{My}$/APRT$^{My}$ mice by standard methods as described below. Alternatively, the ES cells can be maintained in medium containing leukemia-inhibitory factor (LIF), available from AMGEN, during the selection with DAP or 2-FA. The presence of LIF permits the cells to remain undifferentiated and to retain their pluripotent potential.

Although the ES cells of preference are the established D3 and E14 ES cell lines, both derived from 129/SV$^+$/+ mice and available from the University of Cincinnati, College of Medicine, Cincinnati, Ohio, new ES cell lines including Aprt$^-$ ES cells can be produced. Blastocysts, as depicted in FIG. 3, are obtained from 3½, day post coitum (p.c.) mice and are transferred into 10 mm wells containing a monolayer of mitotically inactive feeder cells in 1 ml medium (DMEM plus heat-inactivated 10% newborn calf serum and 10% fetal calf serum). After about 36 hrs., the embryos hatch from the zona pellucida, and attach to the feeder layer via the migrating trophoblast cells. The inner cell mass (ICM) component, formerly sequestered within the trophoblast layer, becomes exposed to the tissue culture environment and rapidly proliferates. By 4 to 6 days in culture, the ICM cells give rise to small clumps, at which time they are physically dislodged from the underlying sheet of trophoblast cells using a finely pulled pasteur pipette. Each clump is individually washed through two changes of Ca$^{++}$/Mg$^{++}$-free phosphate buffered saline (PBS), followed by transfer to a drop (50 ul) of trypsin (0.25%) EDTA (0.04%) medium (69) under oil and incubation for 3 to 5 minutes at 37° C. To disaggregate the clump, it is gently drawn through the mouth of a finely pulled pasteur pipette prefilled with serum-containing medium and expelled repeatedly, generating small aggregates of 3 to 4 cells. The contents of the drop are then transferred to the center of a fresh 10 mm feeder well containing 1 ml culture medium, and incubated at about 37° C.

After about 2 days of culture, discrete colonies become apparent on the feeder layer surface. These colonies may exhibit morphologies characteristic of either trophoblast, epithelial, endodermal or stem cell-like cells. The colonies are usually, but not always, composed exclusively of the same cell type. Those that appear overtly differentiated are readily identified and discarded. Colonies comprised of undifferentiated pluripotential stem cells contain tightly packed small cells with large nuclei, prominent nucleoli and a small rim of cytoplasm. After a week of culture, those colonies containing exclusively cells with an ES phenotype are individually removed, disaggregated as above, and passaged into fresh feeder wells. To ensure that the cell samples are free of differentiated cell types, individual colonies containing only ES type cells are again picked, disaggregated and transferred. After an additional week, the cultures are expanded by trypsinizing the whole well and passaging the pooled contents to a 3 cm feeder well containing 2 ml embryo culture medium. The cultures are fed every second day and transferred to larger dishes as the colonies grow large. When sufficient cells are available, they are ready for genetic manipulation and can be frozen and stored in liquid nitrogen. In all cases, individual ES cell clones will be karyotyped and tested for pluripotency in vitro by allowing them to grow in the absence of a feeder layer, a procedure that promotes in vitro differentiation. For production of chimeric animals, it is preferable to use ES cells with a male karyotype since a chimeric male can sire more offspring, potentially containing the transgene, than a chimeric female can produce, thereby decreasing the time to test for germline chimerism.

To produce chimeric and then transgenic animals from genetically modified ES cells, there are several intermediate steps. The genetically altered ES cells are introduced into 3.5 day p.c. C57BL/6 blastocysts. See, for example, FIG. 3, step #2. Following abdominal incision of 3.5 day pregnant black coat color C57BL/6 females, the uterine horns are severed at the cervix and trimmed from the mesometrium. The uterus is cut below the junction with the oviduct and transferred to a 35 mm petri plate containing M2 medium, as described in Hogan, B. et al. in: *Manipulating the Mouse Embryo: A Laboratory Manual,* Cold Spring Harbor Laboratory (1986). Blastocysts are recovered by flushing each uterine horn with about 1 ml of M2 medium using a 25 gauge needle. For introduction of the genetically modified ES cells of agouti coat color 129/SV$^+$/$^+$ origin into blastocysts of black coat color C57BL/6 origin, the blastocysts are individually held by slight negative pressure to a heat-polished holding pipette with the inner cell mass oriented towards the pipette orifice. An injection needle, optimally containing between 7 and 12 single ES cells, is inserted into the blastocoele. The cells are slowly expelled and the needle withdrawn. The blastocyst will collapse but will subsequently expand following 2–3 hours of culture. Injected blastocysts are transferred to drops of DMEM+10% fetal calf serum under oil and cultured at 37° C. Following reexpansion (about 2 to 3 hours) the chimeric blastocysts are surgically transferred into the uterine horns of 2.5 day p.c. pseudopregnant females. See FIG. 3, step #3.

For the implantation operation, surrogate mothers (about 2.5 day p.c.) are injected with 2.5% avertin (0.017 ml/mg body weight), the back is swabbed with 70% ethanol, and the skin and body wall of the back are cut, avoiding large blood vessels. The large fat pad attached to the ovary is identified, pulled outside of the body and fastened with a serafine clamp. The uterus is visualized under a dissecting microscope, and pierced with a 27 gauge needle below the junction with each oviduct. Optimally, 6 to 7 blastocysts will be expelled from the implanting pipette directly into each uterine horn via the channel produced by the needle. The serafine clamp is then removed, the fat pad, uterus, oviduct and ovary are placed back inside the body wall, which is closed with one or two stitches, and the skin sealed with autoclips. About 18–19 days later, mice are born. See FIG. 3, step #4.

Chimeric mice can be visually identified by patches of agouti coat color against the black coat color characteristic of C57BL/6 mice, which are the source of the best blastulae.

See FIG. 3. The agouti color is produced by the descendants of the 129/SV$^+$/+ ES cells. To confirm that the genetically altered ES cells have populated the germ line, male chimeras are back-crossed to blackcoat color C57BL/6 female mice. Heterozygote progeny will be totally agouti since the agouti phenotype is dominant over the C57BL/6 black coat color. See FIG. 3. The genotype of the agouti progeny can be either APRT$^+$/APRT$^+$, with one APRT gene coming from the chimera and the other coming from the C57BL/6 black female, or APRT$^+$/APRTNEO, with the APRTNEO deriving from the genetically modified ES cells that have populated the germ line of the male chimera. To discriminate between these two possibilities, agouti progeny will be tested for the presence of the APRTNEO fusion gene by cutting off about 1 cm of tail, extracting the DNA and digesting the DNA with BamHl, and performing a Southern blot using the neo gene as the radiolabeled probe. See FIG. 3. If the mouse is heterozygous and contains the APRTNEO fusion gene, a band about 9 kb will be apparent. If the mouse is APRT$^+$/APRT$^+$, there will be no band. The positive mouse will have an APRT$^+$/APRTNEO genotype.

Once it is determined that the chimeric mouse is a germ line chimera and can transmit the APRTNEO transgene, it will be bred to wild-type agouti coat color 129/SV$^+$/+ mice and heterozygotes will be identified by tail blots as above. See FIG. 3. Heterozygotes will be bred to one another to produce Aprt$^-$ mice with an APRTNEO/APRTNEO genotype. See FIG. 3. These mice are useful for cell ablation studies, for testing gene therapy delivery methodologies, for production of Aprt$^-$ mouse embryo fibroblast feeder cells, and as a source of new ES cell lines with an APRTNEO/APRTNEO genotype in a 129/SV$^+$/+ genetic background. Embryos that have an APRT$^+$/APRTNEO genotype are produced by mating APRTNEO/APRTNEO homozygous mice with wild-type mice and are useful for producing new ES cell lines, as previously described, having an APRT$^+$/APRTNEO genotype. See FIG. 3. This mating protocol represents a second way of producing APRT$^+$/APRTNEO ES cells that are useful for introducing a second homologous recombination targeting event in which the single functional APRT gene is replaced by an APRT gene containing a known mutation (e.g. mutants M1 through M6). These ES cells will have an APRT$^{Mx}$/APRT$^-$ genotype, will have an APRT$^-$ phenotype and can be selected in culture medium containing DAP or FA.

The mutant genes M1 through M6, and the frameshift mutant M7 are prepared from the cloned wild-type gene Dush, M. K. et al.: *Proc. Natl. Acad. USA*, 82:2731–2735 (1985), or as reported in U.S. Pat. No. 4,792,520, which are incorporated herein by reference in their entireties and as set forth herein in Example II.

Embryonic stem cells that are APRT$^+$/APRTNEO, produced from the recombination-mediated targeting with the APRTNEO construct in FIG. 1B and Table I, are electroporated with a mutant APRT$^{Mx}$ gene, such as those containing a single point mutation (e.g. M1–M7), and Aprt$^-$ ES cells are selected in medium containing DAP or 2-FA. For selection, the cells are cultured on APRTNEO/APRTNEO MEFs feeder cells derived from the previously described APRTNEO/APRTNEO mouse or in medium containing LIF in the absence of MEF feeder cells. Alternatively, APRT$^+$/APRTNEO ES cells, produced from APRT$^+$/APRTNEO blastocysts, are electroporated with a mutant APRT gene containing one of the single point mutations (e.g. M1–M7), and Aprt$^-$ ES cells are selected as above.

Mice that are APRT deficient with a genotype APRT$^{Mx}$/APRT$^{Mx}$ where Mx signifies a known, inactivating mutation in APRT, are the preferred animals for detection of reverse mutation at APRT by imaging, autoradiographic means, counting of radioactivity in whole animals or individual tissues, or other monitoring devices. To produce mice that are APRT$^{Mx}$/APRT$^{Mx}$ requires several intermediate steps that produce ES cells or mice with genotypes that also have individual, unique utility. See FIG. 3. One starts with pluripotent ES cells that are APRT$^+$/APRTNEO (FIG. 3, step #2 or step #12), whose construction by recombination-mediated gene targeting has been described. In one embodiment, these ES cells are electroporated with APRT genes containing known mutations such as M1 through M6, described above and in Example II, to target and inactivate the lone, remaining functional APRT allele. The genotype of the correctly targeted ES cell is APRT$^{Mx}$/APRTNEO (step #13, FIG. 3). One electroporation is carried out under conditions previously described and ES cells that are Aprt$^-$ are selected in medium containing DAP or FA. Because normal MEF feeder cells are Aprt$^+$ and will be adversely affected by DAP or FA, the ES cells are selected in the absence of MEF feeder cells but in the presence of leukemia inhibitory factor (LIF), which inhibits differentiation. After 48 to 72 hours in DAP or PA selection medium containing LIF, the Aprt$^-$ cells are placed back on MEF feeder cells for further maintenance and analysis. As an alternative to selection of Aprt$^-$ ES cells in the absence of feeder cells and in the presence of LIF, one can make Aprt$^-$ MEFs from mice with the genotype APRTNEO/APRTNEO (step #10, mouse C, FIG. 3) as will be described. These MEF feeder cells are resistant to the effects of DAP or FA and can serve as functional feeder cells for ES cell culture.

The Aprt$^-$ ES cells that arise and that are selected are of two types. Some will be correctly targeted with the mutant APRT gene (e.g. mutants M1–M6) and the others will have incurred a spontaneous, inactivating mutation in the APRT gene. These two types of events can be distinguished from one another by isolating DNA from individual, independently derived Aprt$^-$ ES cell colonies and amplifying the DNA flanking and including the known mutation by PCR. Since the known mutations are designed to create or destroy a diagnostic restriction site, the amplified DNA is subjected to digestion by the diagnostic restriction enzyme, and the gain or loss of the specific sites indicates whether or not the amplified DNA is from a clone which has incurred the proper targeting event. In the case of mutants M1 through M6, the site of mutation is a splice acceptor site and also destroys a unique Pstl restriction site. Amplification of DNA flanking and including the splice site mutation produces a fragment of defined size which is not cleaved by Pstl digestion in DNA from properly targeted cells, but is cleaved by Pstl digestion in DNA from cells with a spontaneous mutation in the APRT gene. It should be recalled that the starting ES cells are heterozygous at the APRT locus (APRT$^+$/APRTNEO) and that only one allele, that which is being targeted or which undergoes spontaneous mutation, will be amplified by PCR. There will be predominantly two types of cells: those correctly targeted and those with an unknown spontaneous mutation in the remaining intact APRT gene. The former are retained for injection into recipient blastocysts. The latter are characterized by PCR amplification and DNA sequencing of the spontaneously mutated APRT gene to determine the precise nature of the mutation. ES cells with known, characterized spontaneous mutations in the intact aprt gene are retained for injection into recipient blastocysts.

Cells that have been properly targeted or have incurred a mutation in the remaining functional aprt allele now have an APRT$^{Mx}$/APRTNEO genotype (step #13, FIG. 3). These cells, maintained in an undifferentiated condition by culture on MEF, are injected into the blastocoele of 3.5 day post-coitum C57BL/6 blastocysts. The blastocysts are prepared, injected and implanted into surrogate mothers as previously described.

Of the mice that are born, those that have agouti patches against the black background of C57BL/6 or are predominantly agouti are chimeric (striped mice, step #15, FIG. 3). In some of the chimeric mice, a proportion of the germ cells are of 129/SV$^+$+ origin which, when transmitted by mating to C57BL/6 mice (black mouse, step #16, FIG. 3), give rise to entirely agouti mice (unshaded mouse, step #17, FIG. 3). Germ cells of C57BL/6 genotype give rise to black mice (black mouse, step #17, FIG. 3). Preferably male chimeras will be mated with female C57BL/6 mice to produce a greater number of test progeny in a shorter time period than the reverse mating. Agouti mice derived from the former mating can have either an APRT$^{Mx}$/APRT$^+$ or an APRTNEO/APRT$^+$ genotype (unshaded mouse, step #17, FIG. 3). Mice with the APRT$^{Mx}$ allele are detected by PCR amplification of the DNA region containing the Mx mutation, and the presence or absence of the mutation is detected by the presence or absence of the diagnostic restriction site at the position of the mutated nucleotide.

In the example of the mutant genes M1–M6, the mutations destroy a PstI site rendering the amplified fragment from that allele insensitive to PstI digestion. Amplification from the wild-type allele will permit digestion with PstI. Thus 50% of the amplified DNA from mice with an APRT M1–M6/APRT$^+$ genotype can be cleaved with PstI. In mice with an APRTNEO/APRT$^+$ genotype, the APRTNEO allele will not support amplification since it will not bind the primer oligonucleotides used for amplifying the mutant APRT segment. Thus, all of the amplified fragment is digested with PstI. To confirm that the mouse does not have an APRTNEO/APRT$^+$ genotype, an amplification reaction specific for amplification of an APRT/NEO fusion fragment is performed as described earlier. If the mouse has an APRT$^{Mx}$/APRT$^+$ genotype, there will be no amplification. To confirm the precise nucleotide change in the APRT$^{Mx}$ allele of APRT$^{Mx}$/APRT$^+$ mice in the example of mutant genes M1–M6, the amplified, non PstI-digested DNA is recovered from the gel by standard methods and directly sequenced in the region of the mutation. Mice with the genotype APRT$^{Mx}$/APRT$^+$ are depicted in FIG. 3 (unshaded mouse D, step #18) and are sib-mated, if possible, or outbred to wild-type mice of selected strain such as 129/SV$^+$/+, C57BL/6 or C3H. Sib-mating of two mice with APRT$^{Mx}$/APRT$^+$ genotype (unshaded mice D$_1$ . . . D$_n$, step #19, FIG. 3) produces offspring of which 25% are APRT$^{Mx}$/APRT$^{Mx}$ (unshaded mouse E, step #20, FIG. 3). Outbreeding APRT$^{Mx}$/APRT$^+$ heterozygotes (unshaded mouse, step #18, FIG. 3) produces 50% APRT$^+$/APRT$^+$ and 50% APRT$^{Mx}$/APRT$^+$ heterozygotes. Heterozygotes (unshaded mice D$_1$, D$_2$ . . . D$_n$, step #19, FIG. 3) are mated to one. another to produce offspring of which 25% are APRT$^{Mx}$/APRT$^{Mx}$ homozygotes (unshaded mouse E, step #20, FIG. 3).

Homozygosity at the APRT locus, and the precise nature of the inactivating mutations, are confirmed by PCR amplification and DNA sequencing as before. Homozygous Aprt$^-$ mice with an APRT$^{Mx}$/APRT$^{Mx}$ genotype, where APRT$^{Mx}$ indicates any of several specific mutant APRT alleles, such as M1 through M6, are the preferred animals for detection of reverse mutations in cells and tissues by incorporation of marked substances that are metabolized by the APRT enzyme. Detection of mutation is by whole body or whole tissue imaging, autoradiography or counting of incorporated radiolabeled precursor. Mice with APRT$^+$/APRTNEO genotype (unshaded mouse A, step #7 and unshaded mouse B, step #8, FIG. 3) are the preferred animals for detection of mutation by forward mutagenesis.

For detection of mutation by reverse mutagenesis in mice with APRT$^{Mx}$/APRT$^{Mx}$ genotype, mice will be treated with known or unknown mutagens, such as EMS, known promutagens such as benzo[a]pyrene, complex mixtures with unknown mutagenic capacity, other substances with unknown mutagenic capacity, or workplace or other environments with unknown mutagenic hazards. Administration may be oral, topical, by inhalation, or by injection. Substances may be applied in a single dose, continuously or intermittently. Animals being tested can be adults, juveniles, or fetuses in utero. The interval between exposure to the substance or environment, and analysis of mutagenesis can range from, for example, 24 hrs. to more than 1 year. Preferably, the interval is between one and two weeks. For detection of mutation by imaging, the animals are injected with adenine analogs that are modified to contain a non-paramagnetic nucleus. Modifications include but are not limited to incorporation of $^{13}$C, $^2$H, $^3$H, $^{19}$F, $^{79}$Br or $^{15}$N into the adenine molecule. Cells with revertant APRT genes take up the modified adenine and retain it intracellularly by the addition of a ribose-phosphate to produce a modified AMP molecule that can be ultimately incorporated into nucleic acids. Modified adenine not taken up by the cells is cleared by the kidneys and excreted in the urine. Thus, 24 to 48 hours after administration, cells with revertant APRT genes will be selectively marked by the modified adenine whereas other cells and body components will lack the modified adenine. Cells that are labeled and are coupled to neighboring cells by gap junctions can transmit the modified adenine to their neighbors via the gap junctions, thereby enlarging the labeled focus. An APRT$^{Mx}$/APRT$^{Mx}$ animal treated in this manner can be scanned for mutations by imaging techniques.

In another embodiment, the animal can be injected with [$^{14}$C] or [$^3$H]-labeled adenine. Only those cells with revertant APRT genes have functional APRT enzyme and convert the radiolabeled adenine to radiolabeled AMP, thereby marking the revertant cells and their non-revertant neighbors to which they are coupled by gap junctions. The animals are allowed 24 hours or more to clear the radiolabeled adenine not taken up by revertant cells. They are then sacrificed and tissues removed, fixed and prepared for autoradiography. Individual radiolabeled cells and foci of radiolabeled cells are detected by silver grains in the autoradiographic photo emulsion overlying the cells.

In yet another embodiment, animals injected with radiolabeled adenine are allowed to clear the adenine and are sacrificed as above. Whole animals or individual tissues are disintegrated mechanically or by solubilization and are counted for radioactivity. The amount of radioactivity incorporated above background will be approximately proportional to the activity of a substance as a specific mutagen.

EXAMPLE II

Construction of a Mutant Mouse APRT Gene Containing a Specific Base-substitution The cloned mouse APRT gene, contained within a 3.1 kb fragment of mouse genomic DNA inserted into the bacterial plasmid pBR328, is designated pSAM-3.1. The pSAM-3.1 is virtually identical to the pSAM-4.4 (Table II). In fact, the pSAM-3.1 is contained in its entirety in the pSAM-4.4. The differences between the two recombinant plasmids are: the pSAM-4.4 includes an additional DNA segment on the order of about 1.3 kb which is a 3' flanking sequence distal to the polyadenylation site; and it contains 4358 nucleotides whereas the pSAM-3.1 contains 3070 nucleotides. The pSAM-3.1 begins at nucleotide 1 and ends at nucleotide 3070 in pSAM-4.4 as recited in Table II. The polyadenylation signal for the pSAM-3.1 is at nucleotides 3047–3052. The 5 exons, 4 introns and polyadenylation signal are in the same location for both and the pSAM-3.1 and the pSAM-4.4. See Dush, M. K. et al.: *Nucleic Acids Research*, 16(7) :8509–8524 (1988), Dush, M. K. et al.: *Proc. Natl. Acad. Sci. USA*, 82:2731–2735 (1985), and Sikela, J. M. et al.: *Gene*, 22:219–228 (1983), which are incorporated herein by reference in their entireties.

The coding regions and introns of the APRT gene as well as certain 5' and 3' untranslated regions have been sequenced in their entirety, and contain five exons and 4 introns. See Dush et al: *Proc. Natl. Acad. Sci. USA*, 82:2731–2735 (1981). The nucleotide sequence at one of the intron/exon junctions is the target for mutagenesis. The sequence surrounding and including the target site is 5' TTCCTGTCTGCAG/GCTGAG 3', and contains a Pst 1 restriction site (indicated by dashed line above sequence). The slash mark denotes the precise RNA splice site. The AG/G sequence that forms the splice site is requisite for splicing in all mammalian systems so far studied. These three nucleotides are highly conserved at intron/exon junctions and form part of a larger but less well-conserved consensus sequence. Alteration or deletion of one of these nucleotides inhibits splice formation at that site resulting in aberrant splicing and loss of functional protein encoded by that gene. As part of this method, the G, for example, that immediately precedes the splice point is converted to an A (transition) or a T or a C (transversions). Likewise, the preceding A (2 nucleotides 5' to the splice site) is converted to a G (transition) or a C or a T (transversion). The resulting transition or transversions have two effects. First of all, they interfere with RNA splicing, thereby blocking production of functional APRT. Secondly, they cause the loss of the Pst 1 site which serves as a useful diagnostic landmark. Regeneration of the Pst 1 by reversion site restores gene function and the Aprt$^+$ phenotype.

The preferred method which produces a targeted base substitution mutation in accordance with this invention closely follows the procedure described by Wallace, R. B. et al.: *Nucl. Acid Res.*, 9:3647–3656 (1981); and Zarucki-Schulz, T., et al.: *J. Biol. Chem.*, 257:11070–11077 (1982), which are incorporated in their entireties herein by reference. Nevertheless, other known suitable methods can also be employed herewith. The recombinant plasmid pSAM-3.1, which contains the intact APRT gene, is first made single stranded. Covalently closed circular pSAM-3.1 DNA is incubated with EcoRI in the presence of 150 ug/ml ethidium bromide. Under these conditions, the superhelical DNA is only nicked in one strand at the EcoRI site and becomes relaxed with greater than 95% efficiency. After removal of the ethidium bromide by isoamyl alcohol extraction, the DNA is deproteinized by phenol extraction, ethanol precipitated and fractionated on an alkaline sucrose gradient to recover single-stranded circular DNA. The sample is neutralized, ethanol precipitated, and treated with *E. coli* exonuclease III to hydrolyze any contaminating single-stranded linear molecules. The remaining circular single-stranded pSAM-3.1 DNA serves as the template for producing the mutant gene.

The nucleotide sequence at the intron/exon junction is 5'---CTGCAG/GCT---3' and is mutated to 5'---CTGCAA/GCT---3' (M1) or 5'---CTGCGG/GCT---3' (M2) or 5'---CTGCAT/GCT---3' (M3) or 5'---CTGCAC/GCT---3' (M4) 5'---CTGCCG/GCT---3' (M5) or 5'---CTGCTG/GCT---3' (M6) to produce the desired transitions or transversions. To this end, the following six octadecanucleotides 5'TCCTGTCTGCAA/GCTGAG3', 5'TCCTGTCTGCGG/GCTGAG3', 5'TCCTGRCTGCAT/GCTGAG3', 5'TCCTGTCTGCAC/GCT3', 5'TCCTGTCTGCG/GCTGAG3', 5'TCCTGTCTGATG/GCT3' are synthesized. Each of these oligonucleotides is complementary to the strand not shown at the splice region of interest except at the underlined nucleotide, which is the mutated site.

As an example, the oligonucleotides 5'TCCTGTCTGCAA/GCTGAG3' and 5'TCCTGTCTGCGG/GCTGA3' are phosphorylated at their 5' ends with T4 polynucleotide kinase, and hybridized with closed circular single-stranded pSAM-3.1 DNA. The hybridized oligonucleotide serves as a primer which is extended upon addition of *E. coli* DNApolymerase 1 (Klenow fragment), the four deoxynucleoside triphophosphates and ATP. The reaction mixture, which also includes T4 DNA Ligase, is incubated at 12° for 12 hours. The product contains repaired circular double-stranded pSAM-1 DNA that has a C:A mismatch in the one case and a G:T mismatch in the second case at the respective target sites.

The repaired plasmid DNA can be used to transform *E. coli* MC 1061 by conventional procedures. Transformants are selected preferably by their resistance to ampicillin. In principle, 50% of the transformants carry the normal APRT gene and 50% the mutated gene. Further, techniques such as identification of transformants containing the mutant gene include, for instance, the known presence of colony hybridization. Using mutant oligonucleotide as a hybridization probe after 5' end-labeling with gamma –[$^{32}$P] ATP and T4 polynucleotide kinase, it is possible to distinguish colonies containing mutant DNA complementary to the entire length of the hybridization probe from colonies that contain non-mutated DNA.

Transformant colonies grown on nitrocellulose filters are replica plated on nitrocellulose filters. Colonies on replica filters are prepared for hybridization with the [$^{32}$P] end-labeled octadecanucleotide that is used to produce the desired base substitution. The hybridization conditions, which are nonstringent, entail incubation for 16 hours at 55° C. in 6X NET (IX NET=150 mM NaCl, 1 mM EDTA, 15 mM Tris-HCl pH 7.5) containing 5X Denhardt's solution, 10% dextran sulfate, 250 ug/ml yeast tRNA, 0.5% nonidet NP-40 and 2 ug/ml radioactive probe. The filters are washed at 0° C. in four to six changes with 6X SSC (1XSSC=0.15M NaCl, 0.015 M Na citrate, pH 7.2), dried and exposed to XR-5 x-ray film and intensifing screen at –70° for 12 hours.

Colonies hybridizing with the probe are recovered from the master filter, expanded, and plasmid DNA prepared by conventional means. Since a colony can conceivably contain plasmids with both wild-type and mutant APRT DNA, this possibility is examined by digestion with Pst 1. The parental plasmid pSAM-1 has two Pst 1 sites, one in the vector and the second at the target splice junction. Digestion with Pst 1 generates two fragments, 2.7 kb and 3.5 kb in length. Plasmid containing mutant APRT DNA lacks the second site and yields only the linear 6.2 kb fragment upon Pst 1 digestion. Should colonies contain a mixture of wild-type and mutant plasmid DNAs, a second round of transformation with isolated plasmid DNA and rescreening of colonies should be performed as above to separate parental from mutant plasmids. As a final precaution, the nucleotide sequence containing the targeted site of the mutated gene is determined to ensure that only the desired mutation is introduced.

The mutations introduced into the pSAM3.1 plasmid are transferred to plasmid pSAM4.4 by cassette mutagenesis to produce a targeting vector with longer stretches of homology than pSAM3.1. As an example, mutants M1–M6 reside at positions 2486 and 2487 of pSAM3.1 and pSAM4.4, and are contained on a BamHl restriction fragment that extends from position 1983 to 2981 (see Table II). The wild-type APRT BamHl fragment from pSAM4.4 is removed and replaced with the BamHl fragment from mutant pSAM3.1, which is identical except for the individual mutations M1 through M6 at positions 2486 and 2487. The mutant APRT gene is separated from the vector after digestion with EcoRl and partial digestion with HindIII, which releases a 4.4 kb fragment, or after complete Xmnl digestion which releases a 3.6 kb fragment. The mutant APRT DNA is electroporated into APRT$^+$/APRTNEO ES cells (as described earlier), and APRT cells are selected in DAP or FA (as described above). Targeted ES cells with an APRT$^{Mx}$/APRTNEO genotype are distinguished from cells that become APRT by spontaneous mutation by Southern blot (as described earlier), and cloned APRT$^{Mx}$/APRTNEO ES cells are injected into host C57BL/6 3.5 day blastocysts as before. These are then implanted into the uterus of a pseudopregnant female to produce germline chimeric mice as described above. After mating to wild-type mice, transgenic progeny of germline chimeras will produce mice, 50% of which will have an APRT$^{Mx}$/APRT$^+$ genotype. Mice with an APRT$^{Mx}$/APRT$^{Mx}$ are produced by sib-mating (see FIG. 3). Mice with an APRT$^{Mx}$/APRT$^{Mx}$ genotype are used as tester mice for reverse mutation, and mice with an APRT$^{Mx}$/APRT$^+$ genotype are used as testers for forward mutation.

While the base substitution mutations of this Example II are produced by oligonucleotide site specific mutagenesis, it should be understood to those of skill in the art that such mutations can be produced by other known techniques, such as by polymerase chain reaction (PCR) amplification, as disclosed in Bowman, et al.: *Technique—J. Methods and Cell and Molecular Biology,* 2:254–260 (1990), which is incorporated herein by reference in its entirety.

The present invention may, of course, be carried out in other specific ways than those herein set forth without departing from the spirit and essential characteristics of the invention. For example, the present invention also applies to those ES cells or nonhuman animals which are nonfunctional hemizygous as a consequence of having one reporter gene deleted, spontaneously or intentionally, or functionally hemizygous as a consequence of X chromosome linkage. The present embodiments are, therefore, to be considered in all respects as illustrative and not restrictive and any changes coming within the meaning and equivalency range of the appended claims are to be embraced therein.

Having described our invention, we claim:

1. A transgenic mouse or its progeny, said transgenic mouse or its progeny having an endogenous gene modified by homologous recombination to produce a reporter gene for detecting the occurrence of mutations in said reporter gene in vivo, or for monitoring the efficacy of a gene or enzyme delivery systems or methods, said reporter gene having a genotype selected from a group consisting of:

reporter gene$^{Mx}$/reporter gene$^{Mx}$, reporter gene$^{Mx}$/reporter gene$^{My}$, reporter gene-marker gene/reporter gene-marker gene,
reporter gene$^{Mx}$/reporter gene-marker gene,
reporter gene$^{My}$/reporter gene-marker gene,
reporter gene$^{Mx}$/−,
reporter gene$^{My}$/−,
reporter gene-marker gene/−,
reporter gene$^{My}$/reporter gene$^{My}$,
reporter gene$^{Mx}$/+,
reporter gene$^{My}$/+,
reporter gene-marker gene/+, and
reporter gene$^+$/−,
wherein said endogenous gene is selected from the group consisting of the HPRT and the TK genes.

* * * * *

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 2529 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: join(67..204, 278..1091)

(xi) SEQUENCE DESCRIPTION: SEQ ID NO:1:

```
CCGGGATTGA CGTGAGTTTA GCGTGCTGAT ACCTACCTCC TCCCTGCCTC CTACACGCAC        60

GCGGCC ATG TCG GAA CCT GAG TTG AAA CTG GTG GCG CGG CGC ATC CGC          108
       Met Ser Glu Pro Glu Leu Lys Leu Val Ala Arg Arg Ile Arg
         1               5                  10

GTC TTC CCC GAC TTC CCA ATC CCG GGC GTG CTG TTC AGG TGC GGT CAC         156
Val Phe Pro Asp Phe Pro Ile Pro Gly Val Leu Phe Arg Cys Gly His
 15                  20                  25                  30

GAG CCG GCG AGG CGT TGG CGC TGT ACG CTC ATC CCC CGG CGC AGG CGG         204
Glu Pro Ala Arg Arg Trp Arg Cys Thr Leu Ile Pro Arg Arg Arg Arg
                 35                  40                  45

TAGGCAGCCT CGGGGATCTT GCGGGGCCTC TGCCCGGCCA CACGCGGGTC ACTCTCCTGT       264

CCTTGTTCCT AGG GAT GCT GCA GCC AAT ATG GGA TCG GCC ATT GAA CAA          313
           Asp Ala Ala Ala Asn Met Gly Ser Ala Ile Glu Gln
                             50                  55

GAT GGA TTG CAC GCA GGT TCT CCG GCC GCT TGG GTG GAG AGG CTA TTC         361
```

```
Asp Gly Leu His Ala Gly Ser Pro Ala Ala Trp Val Glu Arg Leu Phe
     60                  65                  70

GGC TAT GAC TGG GCA CAA CAG ACA ATC GGC TGC TCT GAT GCC GCC GTG      409
Gly Tyr Asp Trp Ala Gln Gln Thr Ile Gly Cys Ser Asp Ala Ala Val
 75                  80                  85                  90

TTC CGG CTG TCA GCG CAG GGG CGC CCG GTT CTT TTT GTC AAG ACC GAC      457
Phe Arg Leu Ser Ala Gln Gly Arg Pro Val Leu Phe Val Lys Thr Asp
                 95                 100                 105

CTG TCC GGT GCC CTG AAT GAA CTG CAG GAC GAG GCA GCG CGG CTA TCG      505
Leu Ser Gly Ala Leu Asn Glu Leu Gln Asp Glu Ala Ala Arg Leu Ser
             110                 115                 120

TGG CTG GCC ACG ACG GGC GTT CCT TGC GCA GCT GTG CTC GAC GTT GTC      553
Trp Leu Ala Thr Thr Gly Val Pro Cys Ala Ala Val Leu Asp Val Val
         125                 130                 135

ACT GAA GCG GGA AGG GAC TGG CTG CTA TTG GGC GAA GTG CCG GGG CAG      601
Thr Glu Ala Gly Arg Asp Trp Leu Leu Leu Gly Glu Val Pro Gly Gln
     140                 145                 150

GAT CTC CTG TCA TCT CAC CTT GCT CCT GCC GAG AAA GTA TCC ATC ATG      649
Asp Leu Leu Ser Ser His Leu Ala Pro Ala Glu Lys Val Ser Ile Met
155                 160                 165                 170

GCT GAT GCA ATG CGG CGG CTG CAT ACG CTT GAT CCG GCT ACC TGC CCA      697
Ala Asp Ala Met Arg Arg Leu His Thr Leu Asp Pro Ala Thr Cys Pro
                 175                 180                 185

TTC GAC CAC CAA GCG AAA CAT CGC ATC GAG CGA GCA CGT ACT CGG ATG      745
Phe Asp His Gln Ala Lys His Arg Ile Glu Arg Ala Arg Thr Arg Met
                190                 195                 200

GAA GCC GGT CTT GTC GAT CAG GAT GAT CTG GAC GAA GAG CAT CAG GGG      793
Glu Ala Gly Leu Val Asp Gln Asp Asp Leu Asp Glu Glu His Gln Gly
            205                 210                 215

CTC GCG CCA GCC GAA CTG TTC GCC AGG CTC AAG GCG CGC ATG CCC GAC      841
Leu Ala Pro Ala Glu Leu Phe Ala Arg Leu Lys Ala Arg Met Pro Asp
        220                 225                 230

GGC GAG GAT CTC GTC GTG ACC CAT GGC GAT GCC TGC TTG CCG AAT ATC      889
Gly Glu Asp Leu Val Val Thr His Gly Asp Ala Cys Leu Pro Asn Ile
235                 240                 245                 250

ATG GTG GAA AAT GGC CGC TTT TCT GGA TTC ATC GAC TGT GGC CGG CTG      937
Met Val Glu Asn Gly Arg Phe Ser Gly Phe Ile Asp Cys Gly Arg Leu
                255                 260                 265

GGT GTG GCG GAC CGC TAT CAG GAC ATA GCG TTG GCT ACC CGT GAT ATT      985
Gly Val Ala Asp Arg Tyr Gln Asp Ile Ala Leu Ala Thr Arg Asp Ile
                270                 275                 280

GCT GAA GAG CTT GGC GGC GAA TGG GCT GAC CGC TTC CTC GTG CTT TAC     1033
Ala Glu Glu Leu Gly Gly Glu Trp Ala Asp Arg Phe Leu Val Leu Tyr
            285                 290                 295

GGT ATC GCC GCT CCC GAT TCG CAG CGC ATC GCC TTC TAT CGC CTT CTT     1081
Gly Ile Ala Ala Pro Asp Ser Gln Arg Ile Ala Phe Tyr Arg Leu Leu
        300                 305                 310

GAC GAG TTCTTCTGAG GGATCGGCA ATAAAAAGAC AGAATAAAAC GCACGGGTGT       1137
Asp Glu Phe
315

TGGGTCGTTT GTTCGGATCC TTGTACTTTG TACACGTCCC ACACCCCTG GAGCATAGCA   1197

GAGCTGTGCT ACTGGAGATC AATAAACCGT TTTGATATGC ATGCCTGCTT CTCCTCAGTT   1257

TGTTGCATGG GTCACATTCC AGGCCTCCAG AGCGATACTA CAGGGACAAG GGGGCTCAGG   1317

TGGGAACCCA TAGGCTCAGC TTTGTATTGA AGCCACAACC CCTACTAGGG AGCAGATGTT   1377

ATCTCTGTCA GTCTCTGAGG CAGCTGACTA CATAAACAGG TTTATTGCTT CACTGTTCTA   1437

GGCCTGTTAT TCCATTAGGA TGGACGAGGA TGAAGCAGTG ACCCACAGCC ACTATATTTT   1497
```

-continued

```
TTTCTGTTGT TTGTCGAGAT GGGGTTTCTT AATATAACCA GCCCTGGCTA TTCTGGACTT    1557

GATTTGTAGC CCAGGCTGGC CTCAAACTTA AGAGGTCCAC TGCCTCTGCT TCTTGAGTGC    1617

TGGGATCAAA GTACGCACCG CAACACCCAG TTCACAGTCA CTATCTCAAA AAAGCTATTT    1677

TGTTGCAGGG CATGGTGTAT AGACCTTTAA TCCTAGTGCC TTGAAGGTAG CAGGCTGTT     1737

AAAATTCAAG GCCAACCTGG CTATATAGTT CCAAGGAGAG CCAGAGCTTT TAGAAAAAAT    1797

AAAAATTTAA AAAATATATA TCAAGCCAGG CATGGTGGCA CACACCTTTG ATCCCAGCAC    1857

TTGGGAGGCA GAGGCAGGGC GGATTTCTGA TCTACAGAAT GAGTTCCAGG ACAACCAGTT    1917

CTACAGAGAA ACCCTGTCTC AAAAAAAAAA AAAAAATCAC ATTCTGGGGA AGTGGGTGTT    1977

GGGGAAAGAG GGGGATGGGA GAGAGCCTGC GTCCCACCAG AGTTCTGGTG CTCCAGGAGG    2037

CTGGATACTT TTCACACTGC CCCAGTGTGA GGCTATCTGG CATGATGTTA AGCCAGTCTC    2097

CGGCACCCCA CACTGGATAT GGTGGAGGAG CTGAGAACAT AATAGGGACC CGGGCAGAAG    2157

GAAAGAGAGG GGGGGGAAGG GAGGGGTGCT GGGTGGAGTC CTTAGTCTGG TCCATGGCTG    2217

CAGCGTAGGA AGCCTTCTGG CAGGTTAAAA GTGCTCATTA GGAGAGCCTA TCCGATCATC    2277

ATTCAAACAC GGTGGGCCTT CATGATCAGA GACAGTCTAT GGTTTTAGAG CTTTATTGTA    2337

GAAAGGGAAG GAGAAAGAGA AGGTAGAAGG ACAGCCATGG CCACGTGGAG AGAGGGGGGA    2397

AGGGAAAGAG AAAAAAAGCC AGAGAGCTTA AGAGAGCGAG GAGGGGCCAA ACATCCCCTT    2457

ATAGTGGGCT TGCCATCTT GCTGTTGCTA GGTAACTGTG GGAAGGGAGT CTAGCCAGAA     2517

TGCCAGAAGC TT                                                        2529
```

(2) INFORMATION FOR SEQ ID NO:2:

(i) SEQUENCE CHARACTERISTICS:
        (A) LENGTH: 317 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ser Glu Pro Glu Leu Lys Leu Val Ala Arg Arg Ile Arg Val Phe
  1               5                  10                  15

Pro Asp Phe Pro Ile Pro Gly Val Leu Phe Arg Cys Gly His Glu Pro
             20                  25                  30

Ala Arg Arg Trp Arg Cys Thr Leu Ile Pro Arg Arg Arg Asp Ala
         35                  40                  45

Ala Ala Asn Met Gly Ser Ala Ile Glu Gln Asp Gly Leu His Ala Gly
     50                  55                  60

Ser Pro Ala Ala Trp Val Glu Arg Leu Phe Gly Tyr Asp Trp Ala Gln
 65                  70                  75                  80

Gln Thr Ile Gly Cys Ser Asp Ala Ala Val Phe Arg Leu Ser Ala Gln
                 85                  90                  95

Gly Arg Pro Val Leu Phe Val Lys Thr Asp Leu Ser Gly Ala Leu Asn
            100                 105                 110

Glu Leu Gln Asp Glu Ala Ala Arg Leu Ser Trp Leu Ala Thr Thr Gly
        115                 120                 125

Val Pro Cys Ala Ala Val Leu Asp Val Val Thr Glu Ala Gly Arg Asp
    130                 135                 140

Trp Leu Leu Leu Gly Glu Val Pro Gly Gln Asp Leu Leu Ser Ser His
145                 150                 155                 160

Leu Ala Pro Ala Glu Lys Val Ser Ile Met Ala Asp Ala Met Arg Arg
```

```
                         165                 170                 175
Leu His Thr Leu Asp Pro Ala Thr Cys Pro Phe Asp His Gln Ala Lys
                180                 185                 190
His Arg Ile Glu Arg Ala Arg Thr Arg Met Glu Ala Gly Leu Val Asp
            195                 200                 205
Gln Asp Asp Leu Asp Glu Glu His Gln Gly Leu Ala Pro Ala Glu Leu
        210                 215                 220
Phe Ala Arg Leu Lys Ala Arg Met Pro Asp Gly Glu Asp Leu Val Val
225                 230                 235                 240
Thr His Gly Asp Ala Cys Leu Pro Asn Ile Met Val Glu Asn Gly Arg
                245                 250                 255
Phe Ser Gly Phe Ile Asp Cys Gly Arg Leu Gly Val Ala Asp Arg Tyr
            260                 265                 270
Gln Asp Ile Ala Leu Ala Thr Arg Asp Ile Ala Glu Glu Leu Gly Gly
        275                 280                 285
Glu Trp Ala Asp Arg Phe Leu Val Leu Tyr Gly Ile Ala Ala Pro Asp
290                 295                 300
Ser Gln Arg Ile Ala Phe Tyr Arg Leu Leu Asp Glu Phe
305                 310                 315

(2) INFORMATION FOR SEQ ID NO:3:

(i) SEQUENCE CHARACTERISTICS:
        (A) LENGTH: 4358 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GAATTCATGC TCACGGGCTC ACAGGAAGGT CCAAGAAGGA ATGTTTAGAA TCCATTGGAC      60

CCTCCCCACA CCCTCTCCTT TGATGGAGCA TGGGCCAATT TGGAGGATAT CTTTTGAGTA     120

ATTGCAACTG CACTGAAGAT GATAATGGCC ATTATACTCA GAGGACAGTC TTTCCACACC     180

ACTACCTATA GACCCAAGTA CTGTGCTGGG AAGGTAGAAC CCCAGTTCTG TCTCTGGCTA     240

TCAGGACCTT CTGGTTCCAC CCCAAAACGA GGAGGGCACA TTCTGTTGCA ATGCACAGGA     300

GTGTCTGTGG TCTCAGAGAA GGCATTCCTT ACCCGCCCTG CTACCCTGCT TTCCCCTGCG     360

CTCTAGCCCA CACACAGTGC ACTCCCACCT CTGGACCTAA GACTATCCAT CAGCTCCCTT     420

CCGGGCTAAT TCCAGGAAAG CAGGGGCTGA ATCTCAGGCC CCTTGTACTA TGCGCGAGGG     480

AAGGAACGCA AGGCCAAACC ACTCCAGCGG ACCTGGGCAA GACCCGTCCC TGCTCCCCCA     540

GGTCCAGAAG ACTAGCCCCT GGAAAAGCAG GACTGAAAAA GCGTGTGTGG GGCAAAACCA     600

AAAAAGGATG GACATCGCAC ATCCCCTTTC CACCCATATA TCTTTGAGGT AGGGATGCTT     660

GTGTTTAGGC AGCTCAAGAA ATCTAACCCC TGACTCAGGC CCCACACACA CCTCGCAGAG     720

GCCCCGCCTC TCAGCCTGTC CGCCCCTCG TGCTAGACCA ACCCGCACCC AGAAGCCCCG      780

CCCATCGAGG ACGCTCCGCC CTTGTTCCCC CCGGGATTGA CGTGAGTTTA GCGTGCTGAT     840

ACCTACCTCC TCCCTGCCTC CTACACGCAC GCGGCCATGT CGGAACCTGA GTTGAAACTG     900

GTGGCGCGGC GCATCCGCGT CTTCCCCGAC TTCCCAATCC CGGGCGTGCT GTTCAGGTGC     960

GGTCACGAGC CGGCGAGGCG TTGGCGCTGT ACGCTCATCC CCCGGCGCAG GCGGTAGGCA    1020

GCCTCGGGGA TCTTGCGGGG CCTCTGCCCG GCCACACGCG GGTCACTCTC CTGTCCTTGT    1080

TCCTAGGGAT ATCTCGCCCC TCTTGAAAGA CCCGGACTCC TTCCGAGCTT CCATCCGCCT    1140
```

-continued

```
CTTGGCCAGT CACCTGAAGT CCACGCACAG CGGCAAGATC GACTACATCG CAGGCGAGTG    1200

GCCTTGCTAG GTCGTGCTCG TCCCCCACGG TCCTAGCCCC TATCCCCTTT CCCCCTCGTG    1260

TCACCCACAG TCTGCCCCAC ACCCATCCAT TCTTCTTCGA CCTCTGACAC TTCCTCCTTG    1320

GTTCCTCACT GCCTTGGACG CTTGTTCACC CTGGATGAAC TATGTAGGAG TCTCCCTTCC    1380

CTGCTAGGTA CCCTAAGGCA TCTGCCCTCG GTGCTTGTTC CTAGAGACGA ACTCTGCTCT    1440

GTCCTTGTGT CCAGAACCAG GCCTCCCTCT TTTAGGGCAC AAAGCTGGCC AGCATCCTGA    1500

CAGCAGGCTG GGAGACCCTG GAACCTCCAG ATGACGGACA TCCTTGCTTA GGGGTAGCCT    1560

CTGGGATGAA CTAGATACTA AAAATTAGGT AACCTTGGTT GGGCGTGGCG TGCCTGGGCA    1620

GACCTCAAGC CTGGTAGCTT CAGGGGCTGT TTCTCCCCAG GACTACACCG GGGCATCTTT    1680

CTCTTGTTCC CTCACACAAG CTTGTGTTAA ACAACTGCTG TCTACTTGGC TCCATGCCTG    1740

AGCTTGAGAA ACACCCTAGG ACAGCTGAAT GTCCACCAGG AGTGTCCAGA GGGAGGGTGG    1800

GCACCCCAGA GAACAGAGTG GCCTTGGTAA GTGCTCGGGG ACCACAGACT TTGCCACTTC    1860

ACTTCCTATT GGTACCCTTG GCCATGCTCC AGAAATTAGG GCATGTATGT ATCCTTCCCA    1920

CGACAGCTAG ATGCTGCATT TGAAGGTGGC AAGACCACCA TAGGTGGCCC TGAGCTGTTC    1980

AGAAGGCAGG TAGGATCCCC AAGGCTGAGA TGATGAGTTG ATGGCTACCC AGTAGCCATC    2040

AACGTTCTTC TAACCGTAGT CAGCAAGACC TAGTGTTCCT AGCAAGTGTT GACCTCGCCC    2100

ATACTTGGCC TCTAGATTCC CATGCCCCTC AGCTCCATCC CACAACCTTC CCTCCTTACC    2160

CTAACAGGTC TAGACTCCAG GGGCTTCCTG TTTGGCCCTT CCCTAGCTCA GGAGCTGGGC    2220

GTGGGCTGTG TGCTCATCCG GAAACAGGGG AAGCTGCCGG GCCCCACTGT GTCAGCCTCC    2280

TATTCTCTGG AGTATGGGAA GGTAAGCGAG CTGTGTGTAG AGGAAGGGCA GGGTCTTATC    2340

ACGGCTACCA GTGTCTAGGA GTAAATGTGG GTGCTCAGAG AGGTTGAGAC ATTGGGTCAG    2400

GTTTACACCA CCCAGAAACG CTCGAGCCTA GGGAGGTGGC CACTTGTTCG CGCCTAGACT    2460

CTGTCTTACA CTACTTCCTG TCTGCAGGCT GAGCTGGAAA TCCAGAAAGA TGCCTTGGAA    2520

CCCGGGCAGA GAGTGGTCAT TGTGGATGAC CTCCTGGCCA CAGGAGGTAA AGAACCAACC    2580

CAAGACAAAC AGACTTCAAA GGGCCAGACC CTGTCCTGGG TGCTGACTAA GCAAAGAGCT    2640

TGAACACCTC CTCTTTCTCT GTCCCTTCCC CCCAGGAACC ATGTTTGCGG CCTGTGACCT    2700

GCTGCACCAG CTCCGGGCTG AAGTGGTGGA GTGTGTGAGC CTGGTGGAGC TGACCTCGCT    2760

GAAGGGCAGG GAGAGGCTAG GACCTATACC ATTCTTCTCT CTCCTCCAGT ATGACTGAGG    2820

AGCTGGCTAG ATGGTCACAC CCCTGCTCCC AGCAGCACTA GGAACTGCTT GGTGGCTCAG    2880

CCTAGGCGCC TAAGTGACCT TTGTGAGCTA CCGGCCGCCC TTTTGTGAGT GTTATCACTC    2940

ATTCCTTTGG TCAGCTGATC CGCCGTGCCT GTGGACCCCT GGATCCTTGT ACTTTGTACA    3000

CGTCCCACAC ACCCTGGAGC ATAGCAGAGC TGTGCTACTG GAGATCAATA AACCGTTTTG    3060

ATATGCATGC CTGCTTCTCC TCAGTTTGTT GCATGGGTCA CATTCCAGGC CTCCAGAGCG    3120

ATACTACAGG GACAAGGGGG CTCAGGTGGG AACCCATAGG CTCAGCTTTG TATTGAAGCC    3180

ACAACCCCTA CTAGGGAGCA GATGTTATCT CTGTCAGTCT CTGAGGCAGC TGACTACATA    3240

AACAGGTTTA TTGCTTCACT GTTCTAGGCC TGTTATTCCA TTAGGATGGA CGAGGATGAA    3300

GCAGTGACCC ACAGCCACTA TATTTTTTTC TGTTGTTTGT CGAGATGGGG TTTCTTAATA    3360

TAACCAGCCC TGGCTATTCT GGACTTGATT TGTAGCCCAG GCTGGCCTCA AACTTAAGAG    3420

GTCCACTGCC TCTGCTTCTT GAGTGCTGGG ATCAAAGTAC GCACCGCAAC ACCCAGTTCA    3480
```

-continued

```
CAGTCACTAT CTCAAAAAAG CTATTTTGTT GCAGGGCATG GTGTATAGAC CTTTAATCCT      3540

AGTGCCTTGA AGGTAGGCAG GCTGTTAAAA TTCAAGGCCA ACCTGGCTAT ATAGTTCCAA      3600

GGAGAGCCAG AGCTTTTAGA AAAATAAAA ATTTAAAAAA TATATATCAA GCCAGGCATG       3660

GTGGCACACA CCTTTGATCC CAGCACTTGG GAGGCAGAGG CAGGGCGGAT TTCTGATCTA      3720

CAGAATGAGT TCCAGGACAA CCAGTTCTAC AGAGAAACCC TGTCTCAAAA AAAAAAAAAA      3780

AATCACATTC TGGGGAAGTG GGTGTTGGGG AAAGAGGGGG ATGGGAGAGA GCCTGCGTCC      3840

CACCAGAGTT CTGGTGCTCC AGGAGGCTGG ATACTTTTCA CACTGCCCCA GTGTGAGGCT      3900

ATCTGGCATG ATGTTAAGCC AGTCTCCGGC ACCCCACACT GGATATGGTG GAGGAGCTGA      3960

GAACATAATA GGGACCCGGG CAGAAGGAAA GAGAGGGGGG GGAAGGGAGG GGTGCTGGGT      4020

GGAGTCCTTA GTCTGGTCCA TGGCTGCAGC GTAGGAAGCC TTCTGGCAGG TTAAAAGTGC      4080

TCATTAGGAG AGCCTATCCG ATCATCATTC AAACACGGTG GGCCTTCATG ATCAGAGACA      4140

GTCTATGGTT TTAGAGCTTT ATTGTAGAAA GGGAAGGAGA AAGAGAAGGT AGAAGGACAG      4200

CCATGGCCAC GTGGAGAGAG GGGGGAAGGG AAACACAAAA AAACCCAGAG AGCTTAAGAG      4260

AGCGAGGAGG GGCCAAACAT CCCCTTATAG TGGGCTTTGC CATCTTGCTG TTGCTAGGTA      4320

ACTGTGGGAA GGGAGTCTAG CCAGAATGCC AGAAGCTT                             4358
```

(2) INFORMATION FOR SEQ ID NO:4:

(i) SEQUENCE CHARACTERISTICS:
        (A) LENGTH: 5363 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(1087..1188, 3247..3306, 3493..3570)

(xi) SEQUENCE DESCRIPTION: SEQ ID NO:4:

```
GAATTCATGC TCACGGGCTC ACAGGAAGGT CCAAGAAGGA ATGTTTAGAA TCCATTGGAC        60

CCTCCCCACA CCCTCTCCTT TGATGGAGCA TGGGCCAATT TGGAGGATAT CTTTTGAGTA       120

ATTGCAACTG CACTGAAGAT GATAATGGCC ATTATACTCA GAGGACAGTC TTTCCACACC       180

ACTACCTATA GACCCAAGTA CTGTGCTGGG AAGGTAGAAC CCCAGTTCTG TCTCTGGCTA       240

TCAGGACCTT CTGGTTCCAC CCCAAAACGA GGAGGGCACA TTCTGTTGCA ATGCACAGGA       300

GTGTCTGTGG TCTCAGAGAA GGCATTCCTT ACCCGCCCTG CTACCCTGCT TTCCCCTGCG       360

CTCTAGCCCA CACACAGTGC ACTCCCACCT CTGGACCTAG ACTATCCATC AGCTCCCTTC       420

CGGTAATTTC AGGAAAGCAG GGGCTGAATC TCAGGCCCTT GTACTATGCG CGAGGGAAGG       480

AACGCAAGGC CAAACCACTC CAGCGGACCT GGGCAAGACC CGTCCCTGCT CCCCCAGGTC       540

CAGAAGACTA GCCCCTGGAA AAGCAGGACT GAAAAGCGT GTGTGGGGCA AAACCAAAAA        600

AGGATGGACA TCGCACATCC CCTTTCCACC CATATATCTT TGAGGTAGGG ATGCTTGTGT       660

TTAGGCAGCT CAAGAAATCT AACCCCTGAC TCAGGCCCCA CACACACCTC GCAGAGGCCC       720

CGCCTCTCAG CCTGTCCCGC CCCTCGTGCT AGACCAACCC GCACCCAGAA GCCCCGCCCA       780

TCGAGGACGC TCCGCCCTTG TTCCCCCCGG GATTGACGTG AGTTTAGCGT GCTGATACCT       840

ACCTCCTCCC TGCCTCCTAC ACGCACGCGG CCATGTCGGA ACCTGAGTTG AAACTGGTGG       900

CGCGGCGCAT CCGCGTCTTC CCCGACTTCC CAATCCCGGG CGTGCTGTTC AGGTGCGGTC       960
```

```
ACGAGCCGGC GAGGCGTTGG CGCTGTACGC TCATCCCCCG GCGCAGGCGG TAGGCAGCCT      1020

CGGGGATCTT GCGGGGCCTC TGCCCGGCCA CACGCGGGTC ACTCTCCTGT CCTTGTTCCT      1080

AGGGAT ATC TCG CCC CTC TTG AAA GAC CCG GAC TCC TTC CGA GCT TCC         1128
       Ile Ser Pro Leu Leu Lys Asp Pro Asp Ser Phe Arg Ala Ser
        1               5                   10

ATC CGC CTC TTG GCC AGT CAC CTG AAG TCC ACG CAC AGC GGC AAG ATC        1176
Ile Arg Leu Leu Ala Ser His Leu Lys Ser Thr His Ser Gly Lys Ile
 15              20              25                  30

GAC TAC ATC GCA GGCGAGTGGC CTTGCTAGGT CGTGCTCGTC CCCCACGGTC            1228
Asp Tyr Ile Ala

CTAGCCCCTA TCCCCTTTCC CCCTCGTGTC ACCCACAGTC TGCCCCACAC CCATCCATTC      1288

TTCTTCGACC TCTGACACTT CCTCCTTGGT TCCTCACTGC CTTGGACGCT TGTTCACCCT      1348

GGATGAACTA TGTAGGAGTC TCCCTTCCCT GCTAGGTACC CTAAGGCATC TGCCCTCGGT      1408

GCTTGTTCCT AGAGACGAAC TCTGCTCTGT CCTTGTGTCC AGAACCAGGC CTCCCTCTTT      1468

TAGGGCACAA AGCTGGCCAG CATCCTGACA GCAGGCTGGG AGACCCTGGA ACCTCCAGAT      1528

GACGGACATC CTTGCTTAGG GGTAGCCTCT GGGATGAACT AGATACTAAA AATTAGGTAA      1588

CCTTGGTTGG GCGTGGCGTG CCTGGGCAGA CCTCAAGCCT GGTAGCTTCA GGGGCTGTTT      1648

CTCCCCAGGA CTACACCGGG GCATCTTTCT CTTGTTCCCT CACACAAGCT TGTGTTAAAC      1708

AACTGCTGTC TACTTGGCTC CATGCCTGAG CTTGAGAAAC ACCCTAGGAC AGCTGAATGT      1768

CCACCAGGAG TGTCCAGAGG GAGGGTGGGC ACCCCAGAGA ACAGAGTGGC CTTGGTAAGT      1828

GCTCGGGGAC CACAGACTTT GCCACTTCAC TTCCTATTGG TACCCTTGGC CATGCTCCAG      1888

AAATTAGGGC ATGTATGTAT CCTTCCCACG ACAGCTAGAT GCTGCATTTG AAGGTGGCAA      1948

GACCACCATA GGTGGCCCTG AGCTGTTCAG AAGGCAGGTA GGATCCCCAA GGCTGAGATG      2008

ATGAGTTGAT GGCTACCCAG TAGCCATCAA CGTTCTTCTA ACCGTAGTCA GCAAGACCTA      2068

GTGTTCCTAG CAAGTGTTGA CCTCGCCCAT ACTTGGCCTC TAGATTCCCA TGCCCCTCAG      2128

CTCCATCCCA CAACCTTCCC TCCTTACCCT AACAGGTCTA GACTCCAGGG GCTTCCTGTT      2188

TGGCCCTTCC CTAGCTCAGG AGCTGGGCGT GGGCTGTGTG CTCATCCGGG ATCTGATCAA      2248

GAGACAGGAT GAGGATCGTT TCGCATGATT GAACAAGATG GATTGCACGC AGGTTCTCCG      2308

GCCGCTTGGG TGGAGAGGCT ATTCGGCTAT GACTGGGCAC AACAGACAAT CGGCTGCTCT      2368

GATGCCGCCG TGTTCCGGCT GTCAGCGCAG GGGCGCCCGG TTCTTTTTGT CAAGACCGAC      2428

CTGTCCGGTG CCCTGAATGA ACTGCAGGAC GAGGCAGCGC GGCTATCGTG GCTGGCCACG      2488

ACGGGCGTTC CTTGCGCAGC TGTGCTCGAC GTTGTCACTG AAGCGGGAAG GGACTGGCTG      2548

CTATTGGGCG AAGTGCCGGG GCAGGATCTC CTGTCATCTC ACCTTGCTCC TGCCGAGAAA      2608

GTATCCATCA TGGCTGATGC AATGCGGCGG CTGCATACGC TTGATCCGGC TACCTGCCCA      2668

TTCGACCACC AAGCGAAACA TCGCATCGAG CGAGCACGTA CTCGGATGGA AGCCGGTCTT      2728

GTCGATCAGG ATGATCTGGA CGAAGAGCAT CAGGGGCTCG CGCCAGCCGA ACTGTTCGCC      2788

AGGCTCAAGG CGCGCATGCC CGACGGCGAG GATCTCGTCG TGACCCATGG CGATGCCTGC      2848

TTGCCGAATA TCATGGTGGA AAATGGCCGC TTTTCTGGAT TCATCGACTG TGGCCGGCTG      2908

GGTGTGGCGG ACCGCTATCA GGACATAGCG TTGGCTACCC GTGATATTGC TGAAGAGCTT      2968

GGCGGCGAAT GGGCTGACCG CTTCCTCGTG CTTTACGGTA TCGCCGCTCC CGATTCGCAG      3028

CGCATCGCCT TCTATCGCCT TCTTGACGAG TTCTTCTGAG CGGGACTCTG GGGTTCGAAA      3088

TGACCGACCA AGCGACGCCC AACCTGCCAT CACGAGATTT CGATTCCACC GCCGCCTTCT      3148
```

-continued

```
ATGAAAGGTT GGGCTTCGGA ATCGTTTTCC GGGACGCCGG CTGGATGATC CTCCAGCGCG    3208

GGGATCTCAT GCTGGAGTTC TTCGCCCACC CCGGCCGG AAA CAG GGG AAG CTG       3261
                                        Lys Gln Gly Lys Leu
                                                        35

CCG GGC CCC ACT GTG TCA GCC TCC TAT TCT CTG GAG TAT GGG AAG         3306
Pro Gly Pro Thr Val Ser Ala Ser Tyr Ser Leu Glu Tyr Gly Lys
 40              45                  50

GTAAGCGAGC TGTGTGTAGA GGAAGGGCAG GGTCTTATCA CGGCTACCAG TGTCTAGGAG    3366

TAAATGTGGG TGCTCAGAGA GGTTGAGACA TTGGGTCAGG TTTACACCAC CCAGAAACGC    3426

TCGAGCCTAG GGAGGTGGCC ACTTGTTCGC GCCTAGACTC TGTCTTACAC TACTTCCTGT    3486

CTGCAG GCT GAG CTG GAA ATC CAG AAA GAT GCC TTG GAA CCC GGG CAG      3534
       Ala Glu Leu Glu Ile Gln Lys Asp Ala Leu Glu Pro Gly Gln
        55                  60                  65

AGA GTG GTC ATT GTG GAT GAC CTC CTG GCC ACA GGA GGTAAAGAAC          3580
Arg Val Val Ile Val Asp Asp Leu Leu Ala Thr Gly
 70                  75                  80

CAACCCAAGA CAAACAGACT TCAAAGGGCC AGACCCTGTC CTGGGTGCTG ACTAAGCAAA    3640

GAGCTTGAAC ACCTCCTCCT TCTCTGTCCC TTCCCCCCAG GAACCATGTT TGCGGCCTGT    3700

GACCTGCTGC ACCAGCTCCG GGCTGAAGTG GTGGAGTGTG TGAGCCTGGT GGAGCTGACC    3760

TCGCTGAAGG GCAGGGAGAG GCTAGGACCT ATACCATTCT TCTCTCTCCT CCAGTATGAC    3820

TGAGGAGCTG GCTAGATGGT CACACCCCTG CTCCCAGCAG CACTAGGAAC TGCTTGGTGG    3880

CTCAGCCTAG GCGCCTAAGT GACCTTTGTG AGCTACCGGC CGCCCTTTTG TGAGTGTTAT    3940

CACTCATTCC TTTGGTCAGC TGATCCGCCG TGCCTGTGGA CCCCTGGATC CTTGTACTTT    4000

GTACACGTGC CACACACCCT GGAGCATAGC AGAGCTGTGC TACTGAGAT CAATAAACCG     4060

TTTTGATATG CATGCCTGCT TCTCCTCAGT TTGTTGCATG GGTCACATTC CAGGCCTCCA    4120

GAGCGATACT ACAGGGACAA GGGGGCTCAG GTGGAACCC ATAGGCTCAG CTTTGTATTG     4180

AAGCCACAAC CCCTACTAGG GAGCAGATGT TATCTCTGTC AGTCTCTGAG GCAGCTGACT    4240

ACATAAACAG GTTTATTGCT TCACTGTTCT AGGCCTGTTA TTCCATTAGG ATGGACGAGG    4300

ATGAAGCAGT GACCCACAGC CACTATATTT TTTTCTGTTG TTTGTCGAGA TGGGGTTTCT    4360

TAATATAACC AGCCCTGGCT ATTCTGGACT TGATTTGTAG CCCAGGCTGG CCTCAAACTT    4420

AAGAGGTCCA CTGCCTCTGC TTCTTGAGTG CTGGGATCAA AGTACGCACC GCAACACCCA    4480

GTTCACAGTC ACTATCTCAA AAAAGCTATT TTGTTGCAGG GCATGGTGTA TAGACCTTTA    4540

ATCCTAGTGC CTTGAAGGTA GGCAGGCTGT TAAAATTCAA GGCCAACCTG GCTATATAGT    4600

TCCAAGGAGA GCCAGAGCTT TTAGAAAAAA TAAAAATTTA AAAATATAT ATCAAGCCAG     4660

GCATGGTGGC ACACACCTTT GATCCCAGCA CTTGGGAGGC AGAGGCAGGG CGGATTTCTG    4720

ATCTACAGAA TGAGTTCCAG ACAACCAGT TCTACAGAGA AACCCTGTCT CAAAAAAAA     4780

AAAAAAATCA CATTCTGGGG AAGTGGGTGT TGGGGAAAGA GGGGGATGGG AGAGAGCCTG    4840

CGTCCCACCA GAGTTCTGGT GCTCCAGGAG GCTGGATACT TTTCACACTG CCCCAGTGTG    4900

AGGCTATCTG GCATGATGTT AAGCCAGTCT CCGGCACCCC ACACTGGATA TGGTGGAGGA    4960

GCTGAGAACA TAATAGGGAC CCGGGCAGAA GGAAAGAGAG GGGGGGGAAG GGAGGGGTGC    5020

TGGGTGGAGT CCTTAGTCTG GTCCATGGCT GCAGCGTAGG AAGCCTTCTG GCAGGTTAAA    5080

AGTGCTCATT AGGAGAGCCT ATCCGATCAT CATTCAAACA CGGTGGGCCT TCATGATCAG    5140

AGACAGTCTA TGGTTTTAGA GCTTTATTGT AGAAAGGGAA GGAGAAAGAG AAGGTAGAAG    5200

GACAGCCATG GCCACGTGGA GAGAGGGGGG AAGGGAAAGA GAAAAAAAGC CAGAGAGCTT    5260
```

```
AAGAGAGCGA GGAGGGGCCA AACATCCCCT TATAGTGGGC TTTGCCATCT TGCTGTTGCT      5320

AGGTAACTGT GGGAAGGGAG TCTAGCCAGA ATGCCAGAAG CTT                       5363
```

(2) INFORMATION FOR SEQ ID NO:5:

(i) SEQUENCE CHARACTERISTICS:
        (A) LENGTH: 80 amino acids
        (B) TYPE: amino acid
        (D) TOPOLOGY: linear (ii) MOLECULE TYPE: protein (xi) SEQUENCE DESCRIPTION: SEQ ID NO:5:

```
Ile Ser Pro Leu Leu Lys Asp Pro Asp Ser Phe Arg Ala Ser Ile Arg
 1               5                  10                  15

Leu Leu Ala Ser His Leu Lys Ser Thr His Ser Gly Lys Ile Asp Tyr
            20                  25                  30

Ile Ala Lys Gln Gly Lys Leu Pro Gly Pro Thr Val Ser Ala Ser Tyr
        35                  40                  45

Ser Leu Glu Tyr Gly Lys Ala Glu Leu Glu Ile Gln Lys Asp Ala Leu
    50                  55                  60

Glu Pro Gly Gln Arg Val Val Ile Val Asp Asp Leu Leu Ala Thr Gly
65                  70                  75                  80
```

(2) INFORMATION FOR SEQ ID NO:6:

(i) SEQUENCE CHARACTERISTICS:
        (A) LENGTH: 5363 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(2163..2201, 2273..3064, 3680..3823)
        (D) OTHER INFORMATION: /note= "Seq Id No 6 represents the DNA
           sequence corresponding to Seq Id No 4 showing the second
           peptide coded for therein."

(xi) SEQUENCE DESCRIPTION: SEQ ID NO:6:

```
GAATTCATGC TCACGGGCTC ACAGGAAGGT CCAAGAAGGA ATGTTTAGAA TCCATTGGAC        60

CCTCCCCACA CCCTCTCCTT TGATGGAGCA TGGGCCAATT TGGAGGATAT CTTTTGAGTA       120

ATTGCAACTG CACTGAAGAT GATAATGGCC ATTATACTCA GAGGACAGTC TTTCCACACC       180

ACTACCTATA GACCCAAGTA CTGTGCTGGG AAGGTAGAAC CCCAGTTCTG TCTCTGGCTA       240

TCAGGACCTT CTGGTTCCAC CCCAAAACGA GGAGGGCACA TTCTGTTGCA ATGCACAGGA       300

GTGTCTGTGG TCTCAGAGAA GGCATTCCTT ACCCGCCCTG CTACCCTGCT TTCCCCTGCG       360

CTCTAGCCCA CACACAGTGC ACTCCCACCT CTGGACCTAG ACTATCCATC AGCTCCCTTC       420

CGGTAATTTC AGGAAAGCAG GGGCTGAATC TCAGGCCCTT GTACTATGCG CGAGGGAAGG       480

AACGCAAGGC CAAACCACTC CAGCGGACCT GGGCAAGACC CGTCCCTGCT CCCCCAGGTC       540

CAGAAGACTA GCCCCTGGAA AAGCAGGACT GAAAAAGCGT GTGTGGGCA AAACCAAAAA        600

AGGATGGACA TCGCACATCC CCTTTCCACC CATATATCTT TGAGGTAGGG ATGCTTGTGT       660

TTAGGCAGCT CAAGAAATCT AACCCCTGAC TCAGGCCCCA CACACACCTC GCAGAGGCCC       720

CGCCTCTCAG CCTGTCCCGC CCCTCGTGCT AGACCAACCC GCACCCAGAA GCCCCGCCCA       780

TCGAGGACGC TCCGCCCTTG TTCCCCCCGG GATTGACGTG AGTTTAGCGT GCTGATACCT       840
```

```
ACCTCCTCCC TGCCTCCTAC ACGCACGCGG CCATGTCGGA ACCTGAGTTG AAACTGGTGG      900

CGCGGCGCAT CCGCGTCTTC CCCGACTTCC CAATCCCGGG CGTGCTGTTC AGGTGCGGTC      960

ACGAGCCGGC GAGGCGTTGG CGCTGTACGC TCATCCCCCG GCGCAGGCGG TAGGCAGCCT     1020

CGGGGATCTT GCGGGGCCTC TGCCCGGCCA CACGCGGGTC ACTCTCCTGT CCTTGTTCCT     1080

AGGGATATCT CGCCCCTCTT GAAAGACCCG GACTCCTTCC GAGCTTCCAT CCGCCTCTTG     1140

GCCAGTCACC TGAAGTCCAC GCACAGCGGC AAGATCGACT ACATCGCAGG CGAGTGGCCT     1200

TGCTAGGTCG TGCTCGTCCC CCACGGTCCT AGCCCCTATC CCCTTTCCCC CTCGTGTCAC     1260

CCACAGTCTG CCCCACACCC ATCCATTCTT CTTCGACCTC TGACACTTCC TCCTTGGTTC     1320

CTCACTGCCT TGGACGCTTG TTCACCCTGG ATGAACTATG TAGGAGTCTC CCTTCCCTGC     1380

TAGGTACCCT AAGGCATCTG CCCTCGGTGC TTGTTCCTAG AGACGAACTC TGCTCTGTCC     1440

TTGTGTCCAG AACCAGGCCT CCCTCTTTTA GGGCACAAAG CTGGCCAGCA TCCTGACAGC     1500

AGGCTGGGAG ACCCTGGAAC CTCCAGATGA CGGACATCCT TGCTTAGGGG TAGCCTCTGG     1560

GATGAACTAG ATACTAAAAA TTAGGTAACC TTGGTTGGGC GTGGCGTGCC TGGGCAGACC     1620

TCAAGCCTGG TAGCTTCAGG GGCTGTTTCT CCCCAGGACT ACACCGGGGC ATCTTTCTCT     1680

TGTTCCCTCA CACAAGCTTG TGTTAAACAA CTGCTGTCTA CTTGGCTCCA TGCCTGAGCT     1740

TGAGAAACAC CCTAGGACAG CTGAATGTCC ACCAGGAGTG TCCAGAGGGA GGGTGGGCAC     1800

CCCAGAGAAC AGAGTGGCCT TGGTAAGTGC TCGGGGACCA CAGACTTTGC CACTTCACTT     1860

CCTATTGGTA CCCTTGGCCA TGCTCCAGAA ATTAGGGCAT GTATGTATCC TTCCCACGAC     1920

AGCTAGATGC TGCATTTGAA GGTGGCAAGA CCACCATAGG TGGCCCTGAG CTGTTCAGAA     1980

GGCAGGTAGG ATCCCCAAGG CTGAGATGAT GAGTTGATGG CTACCCAGTA GCCATCAACG     2040

TTCTTCTAAC CGTAGTCAGC AAGACCTAGT GTTCCTAGCA AGTGTTGACC TCGCCCATAC     2100

TTGGCCTCTA GATTCCCATG CCCCTCAGCT CCATCCCACA ACCTTCCCTC CTTACCCTAA     2160

CA GGT CTA GAC TCC AGG GGC TTC CTG TTT GGC CCT TCC CTA GCTCAGGAGC     2211
   Gly Leu Asp Ser Arg Gly Phe Leu Phe Gly Pro Ser Leu
    1               5                   10

TGGGCGTGGG CTGTGTGCTC ATCCGGGATC TGATCAAGAG ACAGGATGAG GATCGTTTCG     2271

C ATG ATT GAA CAA GAT GGA TTG CAC GCA GGT TCT CCG GCC GCT TGG         2317
  Met Ile Glu Gln Asp Gly Leu His Ala Gly Ser Pro Ala Ala Trp
      15                  20                  25

GTG GAG AGG CTA TTC GGC TAT GAC TGG GCA CAA CAG ACA ATC GGC TGC       2365
Val Glu Arg Leu Phe Gly Tyr Asp Trp Ala Gln Gln Thr Ile Gly Cys
     30                  35                  40

TCT GAT GCC GCC GTG TTC CGG CTG TCA GCG CAG GGG CGC CCG GTT CTT       2413
Ser Asp Ala Ala Val Phe Arg Leu Ser Ala Gln Gly Arg Pro Val Leu
 45                  50                  55                  60

TTT GTC AAG ACC GAC CTG TCC GGT GCC CTG AAT GAA CTG CAG GAC GAG       2461
Phe Val Lys Thr Asp Leu Ser Gly Ala Leu Asn Glu Leu Gln Asp Glu
                 65                  70                  75

GCA GCG CGG CTA TCG TGG CTG GCC ACG ACG GGC GTT CCT TGC GCA GCT       2509
Ala Ala Arg Leu Ser Trp Leu Ala Thr Thr Gly Val Pro Cys Ala Ala
         80                  85                  90

GTG CTC GAC GTT GTC ACT GAA GCG GGA AGG GAC TGG CTG CTA TTG GGC       2557
Val Leu Asp Val Val Thr Glu Ala Gly Arg Asp Trp Leu Leu Leu Gly
     95                 100                 105

GAA GTG CCG GGG CAG GAT CTC CTG TCA TCT CAC CTT GCT CCT GCC GAG       2605
Glu Val Pro Gly Gln Asp Leu Leu Ser Ser His Leu Ala Pro Ala Glu
110                 115                 120
```

-continued

```
AAA GTA TCC ATC ATG GCT GAT GCA ATG CGG CGG CTG CAT ACG CTT GAT    2653
Lys Val Ser Ile Met Ala Asp Ala Met Arg Arg Leu His Thr Leu Asp
125             130             135             140

CCG GCT ACC TGC CCA TTC GAC CAC CAA GCG AAA CAT CGC ATC GAG CGA    2701
Pro Ala Thr Cys Pro Phe Asp His Gln Ala Lys His Arg Ile Glu Arg
                145             150             155

GCA CGT ACT CGG ATG GAA GCC GGT CTT GTC GAT CAG GAT GAT CTG GAC    2749
Ala Arg Thr Arg Met Glu Ala Gly Leu Val Asp Gln Asp Asp Leu Asp
        160             165             170

GAA GAG CAT CAG GGG CTC GCG CCA GCC GAA CTG TTC GCC AGG CTC AAG    2797
Glu Glu His Gln Gly Leu Ala Pro Ala Glu Leu Phe Ala Arg Leu Lys
            175             180             185

GCG CGC ATG CCC GAC GGC GAG GAT CTC GTC GTG ACC CAT GGC GAT GCC    2845
Ala Arg Met Pro Asp Gly Glu Asp Leu Val Val Thr His Gly Asp Ala
190             195             200

TGC TTG CCG AAT ATC ATG GTG GAA AAT GGC CGC TTT TCT GGA TTC ATC    2893
Cys Leu Pro Asn Ile Met Val Glu Asn Gly Arg Phe Ser Gly Phe Ile
205             210             215             220

GAC TGT GGC CGG CTG GGT GTG GCG GAC CGC TAT CAG GAC ATA GCG TTG    2941
Asp Cys Gly Arg Leu Gly Val Ala Asp Arg Tyr Gln Asp Ile Ala Leu
                225             230             235

GCT ACC CGT GAT ATT GCT GAA GAG CTT GGC GGC GAA TGG GCT GAC CGC    2989
Ala Thr Arg Asp Ile Ala Glu Glu Leu Gly Gly Glu Trp Ala Asp Arg
        240             245             250

TTC CTC GTG CTT TAC GGT ATC GCC GCT CCC GAT TCG CAG CGC ATC GCC    3037
Phe Leu Val Leu Tyr Gly Ile Ala Ala Pro Asp Ser Gln Arg Ile Ala
            255             260             265

TTC TAT CGC CTT CTT GAC GAG TTC TTC TGAGCGGGAC TCTGGGGTTC          3084
Phe Tyr Arg Leu Leu Asp Glu Phe Phe
270             275

GAAATGACCG ACCAAGCGAC GCCCAACCTG CCATCACGAG ATTTCGATTC CACCGCCGCC  3144

TTCTATGAAA GGTTGGGCTT CGGAATCGTT TTCCGGACG CCGGCTGGAT GATCCTCCAG   3204

CGCGGGGATC TCATGCTGGA GTTCTTCGCC CACCCCGGCC GGAAACAGGG GAAGCTGCCG  3264

GGCCCCACTG TGTCAGCCTC CTATTCTCTG GAGTATGGGA AGGTAAGCGA GCTGTGTGTA  3324

GAGGAAGGGC AGGGTCTTAT CACGGCTACC AGTGTCTAGG AGTAAATGTG GGTGCTCAGA  3384

GAGGTTGAGA CATTGGGTCA GGTTTACACC ACCCAGAAAC GCTCGAGCCT AGGGAGGTGG  3444

CCACTTGTTC GCGCCTAGAC TCTGTCTTAC ACTACTTCCT GTCTGCAGGC TGAGCTGGAA  3504

ATCCAGAAAG ATGCCTTGGA ACCCGGGCAG AGAGTGGTCA TTGTGGATGA CCTCCTGGCC  3564

ACAGGAGGTA AGAACCAAC CCAAGACAAA CAGACTTCAA AGGGCCAGAC CCTGTCCTGG   3624

GTGCTGACTA AGCAAAGAGC TTGAACACCT CCTCCTTCTC TGTCCCTTCC CCCA GGA    3682
                                                             Gly

ACC ATG TTT GCG GCC TGT GAC CTG CTG CAC CAG CTC CGG GCT GAA GTG    3730
Thr Met Phe Ala Ala Cys Asp Leu Leu His Gln Leu Arg Ala Glu Val
    280             285             290

GTG GAG TGT GTG AGC CTG GTG GAG CTG ACC TCG CTG AAG GGC AGG GAG    3778
Val Glu Cys Val Ser Leu Val Glu Leu Thr Ser Leu Lys Gly Arg Glu
295             300             305             310

AGG CTA GGA CCT ATA CCA TTC TTC TCT CTC CTC CAG TAT GAC TGAGGAGCTG 3830
Arg Leu Gly Pro Ile Pro Phe Phe Ser Leu Leu Gln Tyr Asp
                315             320             325

GCTAGATGGT CACACCCCTG CTCCCAGCAG CACTAGGAAC TGCTTGGTGG CTCAGCCTAG  3890

GCGCCTAAGT GACCTTTGTG AGCTACCGGC CGCCCTTTTG TGAGTGTTAT CACTCATTCC  3950

TTTGGTCAGC TGATCCGCCG TGCCTGTGGA CCCCTGGATC CTTGTACTTT GTACACGTGC  4010
```

```
CACACACCCT GGAGCATAGC AGAGCTGTGC TACTGGAGAT CAATAAACCG TTTTGATATG   4070

CATGCCTGCT TCTCCTCAGT TTGTTGCATG GGTCACATTC CAGGCCTCCA GAGCGATACT   4130

ACAGGGACAA GGGGGCTCAG GTGGGAACCC ATAGGCTCAG CTTTGTATTG AAGCCACAAC   4190

CCCTACTAGG GAGCAGATGT TATCTCTGTC AGTCTCTGAG GCAGCTGACT ACATAAACAG   4250

GTTTATTGCT TCACTGTTCT AGGCCTGTTA TTCCATTAGG ATGGACGAGG ATGAAGCAGT   4310

GACCCACAGC CACTATATTT TTTTCTGTTG TTTGTCGAGA TGGGGTTTCT TAATATAACC   4370

AGCCCTGGCT ATTCTGGACT TGATTTGTAG CCCAGGCTGG CCTCAAACTT AAGAGGTCCA   4430

CTGCCTCTGC TTCTTGAGTG CTGGGATCAA AGTACGCACC GCAACACCCA GTTCACAGTC   4490

ACTATCTCAA AAAAGCTATT TTGTTGCAGG GCATGGTGTA TAGACCTTTA ATCCTAGTGC   4550

CTTGAAGGTA GGCAGGCTGT TAAAATTCAA GGCCAACCTG GCTATATAGT TCCAAGGAGA   4610

GCCAGAGCTT TTAGAAAAAA TAAAAATTTA AAAAATATAT ATCAAGCCAG GCATGGTGGC   4670

ACACACCTTT GATCCCAGCA CTTGGGAGGC AGAGGCAGGG CGGATTTCTG ATCTACAGAA   4730

TGAGTTCCAG GACAACCAGT TCTACAGAGA AACCCTGTCT CAAAAAAAAA AAAAAAATCA   4790

CATTCTGGGG AAGTGGGTGT TGGGGAAAGA GGGGGATGGG AGAGAGCCTG CGTCCCACCA   4850

GAGTTCTGGT GCTCCAGGAG GCTGGATACT TTTCACACTG CCCCAGTGTG AGGCTATCTG   4910

GCATGATGTT AAGCCAGTCT CCGGCACCCC ACACTGGATA TGGTGGAGGA GCTGAGAACA   4970

TAATAGGGAC CCGGGCAGAA GGAAAGAGAG GGGGGGGAAG GGAGGGGTGC TGGGTGGAGT   5030

CCTTAGTCTG GTCCATGGCT GCAGCGTAGG AAGCCTTCTG GCAGGTTAAA AGTGCTCATT   5090

AGGAGAGCCT ATCCGATCAT CATTCAAACA CGGTGGGCCT TCATGATCAG AGACAGTCTA   5150

TGGTTTTAGA GCTTTATTGT AGAAAGGGAA GGAGAAAGAG AAGGTAGAAG GACAGCCATG   5210

GCCACGTGGA GAGAGGGGGG AAGGGAAAGA GAAAAAAAGC CAGAGAGCTT AAGAGAGCGA   5270

GGAGGGGCCA AACATCCCCT TATAGTGGGC TTTGCCATCT TGCTGTTGCT AGGTAACTGT   5330

GGGAAGGGAG TCTAGCCAGA ATGCCAGAAG CTT                                5363
```

(2) INFORMATION FOR SEQ ID NO:7:

(i) SEQUENCE CHARACTERISTICS:
        (A) LENGTH: 324 amino acids
        (B) TYPE: amino acid
        (D) TOPOLOGY: linear (ii) MOLECULE TYPE: protein (xi) SEQUENCE DESCRIPTION: SEQ ID NO:7:

```
Gly Leu Asp Ser Arg Gly Phe Leu Phe Gly Pro Ser Leu Met Ile Glu
 1               5                  10                  15

Gln Asp Gly Leu His Ala Gly Ser Pro Ala Ala Trp Val Glu Arg Leu
            20                  25                  30

Phe Gly Tyr Asp Trp Ala Gln Gln Thr Ile Gly Cys Ser Asp Ala Ala
        35                  40                  45

Val Phe Arg Leu Ser Ala Gln Gly Arg Pro Val Leu Phe Val Lys Thr
    50                  55                  60

Asp Leu Ser Gly Ala Leu Asn Glu Leu Gln Asp Glu Ala Ala Arg Leu
65                  70                  75                  80

Ser Trp Leu Ala Thr Thr Gly Val Pro Cys Ala Ala Val Leu Asp Val
                85                  90                  95

Val Thr Glu Ala Gly Arg Asp Trp Leu Leu Leu Gly Glu Val Pro Gly
            100                 105                 110
```

```
Gln Asp Leu Leu Ser Ser His Leu Ala Pro Ala Glu Lys Val Ser Ile
        115                 120                 125

Met Ala Asp Ala Met Arg Arg Leu His Thr Leu Asp Pro Ala Thr Cys
130                 135                 140

Pro Phe Asp His Gln Ala Lys His Arg Ile Glu Arg Ala Arg Thr Arg
145                 150                 155                 160

Met Glu Ala Gly Leu Val Asp Gln Asp Leu Asp Glu Glu His Gln
                165                 170                 175

Gly Leu Ala Pro Ala Glu Leu Phe Ala Arg Leu Lys Ala Arg Met Pro
                180                 185                 190

Asp Gly Glu Asp Leu Val Val Thr His Gly Asp Ala Cys Leu Pro Asn
        195                 200                 205

Ile Met Val Glu Asn Gly Arg Phe Ser Gly Phe Ile Asp Cys Gly Arg
        210                 215                 220

Leu Gly Val Ala Asp Arg Tyr Gln Asp Ile Ala Leu Ala Thr Arg Asp
225                 230                 235                 240

Ile Ala Glu Glu Leu Gly Gly Glu Trp Ala Asp Arg Phe Leu Val Leu
                245                 250                 255

Tyr Gly Ile Ala Ala Pro Asp Ser Gln Arg Ile Ala Phe Tyr Arg Leu
                260                 265                 270

Leu Asp Glu Phe Phe Gly Thr Met Phe Ala Ala Cys Asp Leu Leu His
        275                 280                 285

Gln Leu Arg Ala Glu Val Val Glu Cys Val Ser Leu Val Glu Leu Thr
290                 295                 300

Ser Leu Lys Gly Arg Glu Arg Leu Gly Pro Ile Pro Phe Phe Ser Leu
305                 310                 315                 320

Leu Gln Tyr Asp (2) INFORMATION FOR SEQ ID NO:8:

(i) SEQUENCE CHARACTERISTICS:
        (A) LENGTH: 5363 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(873..953, 2202..2276)
        (D) OTHER INFORMATION: /note= "Seq Id No 8 represents the DNA
            sequence corresponding to Seq Id No 4 showing the third
            peptide coded for therein."

(xi) SEQUENCE DESCRIPTION: SEQ ID NO:8:

GAATTCATGC TCACGGGCTC ACAGGAAGGT CCAAGAAGGA ATGTTTAGAA TCCATTGGAC      60

CCTCCCCACA CCCTCTCCTT TGATGGAGCA TGGGCCAATT TGGAGGATAT CTTTTGAGTA     120

ATTGCAACTG CACTGAAGAT GATAATGGCC ATTATACTCA GAGGACAGTC TTTCCACACC     180

ACTACCTATA GACCCAAGTA CTGTGCTGGG AAGGTAGAAC CCCAGTTCTG TCTCTGGCTA     240

TCAGGACCTT CTGGTTCCAC CCCAAAACGA GGAGGGCACA TTCTGTTGCA ATGCACAGGA     300

GTGTCTGTGG TCTCAGAGAA GGCATTCCTT ACCCGCCCTG CTACCCTGCT TTCCCCTGCG     360

CTCTAGCCCA CACACAGTGC ACTCCCACCT CTGGACCTAG ACTATCCATC AGCTCCCTTC     420

CGGTAATTTC AGGAAAGCAG GGGCTGAATC TCAGGCCCTT GTACTATGCG CGAGGGAAGG     480

AACGCAAGGC CAAACCACTC CAGCGGACCT GGGCAAGACC CGTCCCTGCT CCCCCAGGTC     540
```

-continued

| | |
|---|---|
| CAGAAGACTA GCCCCTGGAA AAGCAGGACT GAAAAAGCGT GTGTGGGGCA AAACCAAAAA | 600 |
| AGGATGGACA TCGCACATCC CCTTTCCACC CATATATCTT TGAGGTAGGG ATGCTTGTGT | 660 |
| TTAGGCAGCT CAAGAAATCT AACCCCTGAC TCAGGCCCCA CACACACCTC GCAGAGGCCC | 720 |
| CGCCTCTCAG CCTGTCCCGC CCCTCGTGCT AGACCAACCC GCACCCAGAA GCCCCGCCCA | 780 |
| TCGAGGACGC TCCGCCCTTG TTCCCCCCGG GATTGACGTG AGTTTAGCGT GCTGATACCT | 840 |
| ACCTCCTCCC TGCCTCCTAC ACGCACGCGG CC ATG TCG GAA CCT GAG TTG AAA | 893 |
|   Met Ser Glu Pro Glu Leu Lys | |
|   1                       5 | |
| CTG GTG GCG CGG CGC ATC CGC GTC TTC CCC GAC TTC CCA ATC CCG GGC | 941 |
| Leu Val Ala Arg Arg Ile Arg Val Phe Pro Asp Phe Pro Ile Pro Gly | |
|   10              15              20 | |
| GTG CTG TTC AGG TGCGGTCACG AGCCGGCGAG GCGTTGGCGC TGTACGCTCA | 993 |
| Val Leu Phe Arg | |
|    25 | |
| TCCCCCGGCG CAGGCGGTAG GCAGCCTCGG GGATCTTGCG GGGCCTCTGC CCGGCCACAC | 1053 |
| GCGGGTCACT CTCCTGTCCT TGTTCCTAGG GATATCTCGC CCCTCTTGAA AGACCCGGAC | 1113 |
| TCCTTCCGAG CTTCCATCCG CCTCTTGGCC AGTCACCTGA AGTCCACGCA CAGCGGCAAG | 1173 |
| ATCGACTACA TCGCAGGCGA GTGGCCTTGC TAGGTCGTGC TCGTCCCCCA CGGTCCTAGC | 1233 |
| CCCTATCCCC TTTCCCCCTC GTGTCACCCA CAGTCTGCCC CACACCCATC CATTCTTCTT | 1293 |
| CGACCTCTGA CACTTCCTCC TTGGTTCCTC ACTGCCTTGG ACGCTTGTTC ACCCTGGATG | 1353 |
| AACTATGTAG GAGTCTCCCT TCCCTGCTAG GTACCCTAAG GCATCTGCCC TCGGTGCTTG | 1413 |
| TTCCTAGAGA CGAACTCTGC TCTGTCCTTG TGTCCAGAAC CAGGCCTCCC TCTTTTAGGG | 1473 |
| CACAAAGCTG GCCAGCATCC TGACAGCAGG CTGGAGACCC CTGGAACCTC CAGATGACGG | 1533 |
| ACATCCTTGC TTAGGGGTAG CCTCTGGGAT GAACTAGATA CTAAAAATTA GGTAACCTTG | 1593 |
| GTTGGGCGTG GCGTGCCTGG GCAGACCTCA AGCCTGGTAG CTTCAGGGGC TGTTTCTCCC | 1653 |
| CAGGACTACA CCGGGGCATC TTTCTCTTGT TCCCTCACAC AAGCTTGTGT TAAACAACTG | 1713 |
| CTGTCTACTT GGCTCCATGC CTGAGCTTGA GAAACACCCT AGGACAGCTG AATGTCCACC | 1773 |
| AGGAGTGTCC AGAGGGAGGG TGGGCACCCC AGAGAACAGA GTGGCCTTGG TAAGTGCTCG | 1833 |
| GGGACCACAG ACTTTGCCAC TTCACTTCCT ATTGGTACCC TTGGCCATGC TCCAGAAATT | 1893 |
| AGGGCATGTA TGTATCCTTC CCACGACAGC TAGATGCTGC ATTTGAAGGT GGCAAGACCA | 1953 |
| CCATAGGTGG CCCTGAGCTG TTCAGAAGGC AGGTAGGATC CCCAAGGCTG AGATGATGAG | 2013 |
| TTGATGGCTA CCCAGTAGCC ATCAACGTTC TTCTAACCGT AGTCAGCAAG ACCTAGTGTT | 2073 |
| CCTAGCAAGT GTTGACCTCG CCCATACTTG GCCTCTAGAT TCCCATGCCC CTCAGCTCCA | 2133 |
| TCCCACAACC TTCCCTCCTT ACCCTAACAG GTCTAGACTC CAGGGCTTC CTGTTTGGCC | 2193 |
| CTTCCCTA GCT CAG GAG CTG GGC GTG GGC TGT GTG CTC ATC CGG GAT CTG | 2243 |
|         Ala Gln Glu Leu Gly Val Gly Cys Val Leu Ile Arg Asp Leu | |
|              30              35              40 | |
| ATC AAG AGA CAG GAT GAG GAT CGT TTC GCA TGATTGAACA AGATGGATTG | 2293 |
| Ile Lys Arg Gln Asp Glu Asp Arg Phe Ala | |
|    45                      50 | |
| CACGCAGGTT CTCCGGCCGC TTGGGTGGAG AGGCTATTCG GCTATGACTG GGCACAACAG | 2353 |
| ACAATCGGCT GCTCTGATGC CGCCGTGTTC CGGCTGTCAG CGCAGGGGCG CCCGGTTCTT | 2413 |
| TTTGTCAAGA CCGACCTGTC CGGTGCCCTG AATGAACTGC AGGACGAGGC AGCGCGGCTA | 2473 |
| TCGTGGCTGG CCACGACGGG CGTTCCTTGC GCAGCTGTGC TCGACGTTGT CACTGAAGCG | 2533 |
| GGAAGGGACT GGCTGCTATT GGGCGAAGTG CCGGGGCAGG ATCTCCTGTC ATCTCACCTT | 2593 |

-continued

```
GCTCCTGCCG AGAAAGTATC CATCATGGCT GATGCAATGC GGCGGCTGCA TACGCTTGAT    2653

CCGGCTACCT GCCCATTCGA CCACCAAGCG AAACATCGCA TCGAGCGAGC ACGTACTCGG    2713

ATGGAAGCCG GTCTTGTCGA TCAGGATGAT CTGGACGAAG AGCATCAGGG GCTCGCGCCA    2773

GCCGAACTGT TCGCCAGGCT CAAGGCGCGC ATGCCCGACG GCGAGGATCT CGTCGTGACC    2833

CATGGCGATG CCTGCTTGCC GAATATCATG GTGGAAAATG GCCGCTTTTC TGGATTCATC    2893

GACTGTGGCC GGCTGGGTGT GGCGGACCGC TATCAGGACA TAGCGTTGGC TACCCGTGAT    2953

ATTGCTGAAG AGCTTGGCGG CGAATGGGCT GACCGCTTCC TCGTGCTTTA CGGTATCGCC    3013

GCTCCCGATT CGCAGCGCAT CGCCTTCTAT CGCCTTCTTG ACGAGTTCTT CTGAGCGGGA    3073

CTCTGGGGTT CGAAATGACC GACCAAGCGA CGCCCAACCT GCCATCACGA GATTTCGATT    3133

CCACCGCCGC CTTCTATGAA AGGTTGGGCT TCGGAATCGT TTTCCGGGAC GCCGGCTGGA    3193

TGATCCTCCA GCGCGGGGAT CTCATGCTGG AGTTCTTCGC CCACCCCGGC CGGAAACAGG    3253

GGAAGCTGCC GGGCCCCACT GTGTCAGCCT CCTATTCTCT GGAGTATGGG AAGGTAAGCG    3313

AGCTGTGTGT AGAGGAAGGG CAGGGTCTTA TCACGGCTAC CAGTGTCTAG GAGTAAATGT    3373

GGGTGCTCAG AGAGGTTGAG ACATTGGGTC AGGTTTACAC CACCCAGAAA CGCTCGAGCC    3433

TAGGGAGGTG GCCACTTGTT CGCGCCTAGA CTCTGTCTTA CACTACTTCC TGTCTGCAGG    3493

CTGAGCTGGA AATCCAGAAA GATGCCTTGG AACCCGGGCA GAGAGTGGTC ATTGTGGATG    3553

ACCTCCTGGC CACAGGAGGT AAAGAACCAA CCCAAGACAA ACAGACTTCA AAGGGCCAGA    3613

CCCTGTCCTG GGTGCTGACT AAGCAAAGAG CTTGAACACC TCCTCCTTCT CTGTCCCTTC    3673

CCCCCAGGAA CCATGTTTGC GGCCTGTGAC CTGCTGCACC AGCTCCGGGC TGAAGTGGTG    3733

GAGTGTGTGA GCCTGGTGGA GCTGACCTCG CTGAAGGGCA GGGAGAGGCT AGGACCTATA    3793

CCATTCTTCT CTCTCCTCCA GTATGACTGA GGAGCTGGCT AGATGGTCAC ACCCCTGCTC    3853

CCAGCAGCAC TAGGAACTGC TTGGTGGCTC AGCCTAGGCG CCTAAGTGAC CTTTGTGAGC    3913

TACCGGCCGC CCTTTTGTGA GTGTTATCAC TCATTCCTTT GGTCAGCTGA TCCGCCGTGC    3973

CTGTGGACCC CTGGATCCTT GTACTTTGTA CACGTGCCAC ACACCCTGGA GCATAGCAGA    4033

GCTGTGCTAC TGGAGATCAA TAAACCGTTT TGATATGCAT GCCTGCTTCT CCTCAGTTTG    4093

TTGCATGGGT CACATTCCAG GCCTCCAGAG CGATACTACA GGGACAAGGG GGCTCAGGTG    4153

GGAACCCATA GGCTCAGCTT TGTATTGAAG CCACAACCCC TACTAGGGAG CAGATGTTAT    4213

CTCTGTCAGT CTCTGAGGCA GCTGACTACA TAAACAGGTT TATTGCTTCA CTGTTCTAGG    4273

CCTGTTATTC CATTAGGATG GACGAGGATG AAGCAGTGAC CCACAGCCAC TATATTTTTT    4333

TCTGTTGTTT GTCGAGATGG GGTTTCTTAA TATAACCAGC CCTGGCTATT CTGGACTTGA    4393

TTTGTAGCCC AGGCTGGCCT CAAACTTAAG AGGTCCACTG CCTCTGCTTC TTGAGTGCTG    4453

GGATCAAAGT ACGCACCGCA ACACCCAGTT CACAGTCACT ATCTCAAAAA AGCTATTTTG    4513

TTGCAGGGCA TGGTGTATAG ACCTTTAATC CTAGTGCCTT GAAGGTAGGC AGGCTGTTAA    4573

AATTCAAGGC CAACCTGGCT ATATAGTTCC AAGGAGAGCC AGAGCTTTTA GAAAAAATAA    4633

AAATTTAAAA AATATATATC AAGCCAGGCA TGGTGGCACA CACCTTTGAT CCCAGCACTT    4693

GGGAGGCAGA GGCAGGCGG ATTTCTGATC TACAGAATGA GTTCCAGGAC AACCAGTTCT    4753

ACAGAGAAAC CCTGTCTCAA AAAAAAAAA AAAATCACAT TCTGGGAAG TGGGTGTTGG    4813

GGAAAGAGGG GGATGGGAGA GAGCCTGCGT CCCACCAGAG TTCTGGTGCT CCAGGAGGCT    4873

GGATACTTTT CACACTGCCC CAGTGTGAGG CTATCTGGCA TGATGTTAAG CCAGTCTCCG    4933
```

-continued

```
GCACCCCACA CTGGATATGG TGGAGGAGCT GAGAACATAA TAGGGACCCG GGCAGAAGGA    4993

AAGAGAGGGG GGGGAAGGGA GGGGTGCTGG GTGGAGTCCT TAGTCTGGTC CATGGCTGCA    5053

GCGTAGGAAG CCTTCTGGCA GGTTAAAAGT GCTCATTAGG AGAGCCTATC CGATCATCAT    5113

TCAAACACGG TGGGCCTTCA TGATCAGAGA CAGTCTATGG TTTTAGAGCT TTATTGTAGA    5173

AAGGGAAGGA GAAAGAGAAG GTAGAAGGAC AGCCATGGCC ACGTGGAGAG AGGGGGGAAG    5233

GGAAAGAGAA AAAAAGCCAG AGAGCTTAAG AGAGCGAGGA GGGGCCAAAC ATCCCCTTAT    5293

AGTGGGCTTT GCCATCTTGC TGTTGCTAGG TAACTGTGGG AAGGGAGTCT AGCCAGAATG    5353

CCAGAAGCTT                                                           5363
```

(2) INFORMATION FOR SEQ ID NO:9:

(i) SEQUENCE CHARACTERISTICS:
        (A) LENGTH: 51 amino acids
        (B) TYPE: amino acid
        (D) TOPOLOGY: linear (ii) MOLECULE TYPE: protein (xi) SEQUENCE DESCRIPTION: SEQ ID NO:9:

```
Met Ser Glu Pro Glu Leu Lys Leu Val Ala Arg Arg Ile Arg Val Phe
 1               5                  10                  15

Pro Asp Phe Pro Ile Pro Gly Val Leu Phe Arg Ala Gln Glu Leu Gly
             20                  25                  30

Val Gly Cys Val Leu Ile Arg Asp Leu Ile Lys Arg Gln Asp Glu Asp
         35                  40                  45

Arg Phe Ala
     50
```

(2) INFORMATION FOR SEQ ID NO:10:

(i) SEQUENCE CHARACTERISTICS:
        (A) LENGTH: 3628 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(123..224, 2529..2606)

(xi) SEQUENCE DESCRIPTION: SEQ ID NO:10:

```
GCCGGCGAGG CGTTGGCGCT GTACGCTCAT CCCCCGGCGC AGGCGGTAGG CAGCCTCGGG      60

GATCTTGCGG GGCCTCTGCC CGGCCACACG CGGGTCACTC TCCTGTCCTT GTTCCTAGGG     120

AT ATC TCG CCC CTC TTG AAA GAC CCG GAC TCC TTC CGA GCT TCC ATC        167
   Ile Ser Pro Leu Leu Lys Asp Pro Asp Ser Phe Arg Ala Ser Ile
    1               5                  10                  15

CGC CTC TTG GCC AGT CAC CTG AAG TCC ACG CAC AGC GGC AAG ATC GAC       215
Arg Leu Leu Ala Ser His Leu Lys Ser Thr His Ser Gly Lys Ile Asp
                 20                  25                  30

TAC ATC GCA GGCGAGTGGC CTTGCTAGGT CGTGCTCGTC CCCCACGGTC               264
Tyr Ile Ala

CTAGCCCCTA TCCCCTTTCC CCCTCGTGTC ACCCACAGTC TGCCCCACAC CCATCCATTC     324

TTCTTCGACC TCTGACACTT CCTCCTTGGT TCCTCACTGC CTTGGACGCT TGTTCACCCT     384

GGATGAACTA TGTAGGAGTC TCCCTTCCCT GCTAGGTACC CTAAGGCATC TGCCCTCGGT     444

GCTTGTTCCT AGAGACGAAC TCTGCTCTGT CCTTGTGTCC AGAACCAGGC CTCCCTCTTT     504
```

-continued

```
TAGGGCACAA AGCTGGCCAG CATCCTGACA GCAGGCTGGG AGACCCTGGA ACCTCCAGAT      564
GACGGACATC CTTGCTTAGG GGTAGCCTCT GGGATGAACT AGATACTAAA AATTAGGTAA      624
CCTTGGTTGG GCGTGGCGTG CCTGGGCAGA CCTCAAGCCT GGTAGCTTCA GGGGCTGTTT      684
CTCCCCAGGA CTACACCGGG GCATCTTTCT CTTGTTCCCT CACACAAGCT TGTGTTAAAC      744
AACTGCTGTC TACTTGGCTC CATGCCTGAG CTTGAGAAAC ACCCTAGGAC AGCTGAATGT      804
CCACCAGGAG TGTCCAGAGG GAGGGTGGGC ACCCCAGAGA ACAGAGTGGC CTTGGTAAGT      864
GCTCGGGGAC CACAGACTTT GCCACTTCAC TTCCTATTGG TACCCTTGGC CATGCTCCAG      924
AAATTAGGGC ATGTATGTAT CCTTCCCACG ACAGCTAGAT GCTGCATTTG AAGGTGGCAA      984
GACCACCATA GGTGGCCCTG AGCTGTTCAG AAGGCAGGTA GGATCCCCAA GGCTGAGATG     1044
ATGAGTTGAT GGCTACCCAG TAGCCATCAA CGTTCTTCTA ACCGTAGTCA GCAAGACCTA     1104
GTGTTCCTAG CAAGTGTTGA CCTCGCCCAT ACTTGGCCTC TAGATTCCCA TGCCCCTCAG     1164
CTCCATCCCA CAACCTTCCC TCCTTACCCT AACAGGTCTA GACTCCAGGG GCTTCCTGTT     1224
TGGCCCTTCC CTAGCTCAGG AGCTGGGCGT GGGCTGTGTG CTCATCCGGG ATCTGATCAA     1284
GAGACAGGAT GAGGATCGTT TCGCATGATT GAACAAGATG GATTGCACGC AGGTTCTCCG     1344
GCCGCTTGGG TGGAGAGGCT ATTCGGTAT GACTGGGCAC AACAGACAAT CGGCTGCTCT     1404
GATGCCGCCG TGTTCCGGCT GTCAGCGCAG GGGCGCCCGG TTCTTTTTGT CAAGACCGAC     1464
CTGTCCGGTG CCCTGAATGA ACTGCAGGAC GAGGCAGCGC GGCTATCGTG GCTGGCCACG     1524
ACGGGCGTTC CTTGCGCAGC TGTGCTCGAC GTTGTCACTG AAGCGGGAAG GGACTGGCTG     1584
CTATTGGGCG AAGTGCCGGG GCAGGATCTC CTGTCATCTC ACCTTGCTCC TGCCGAGAAA     1644
GTATCCATCA TGGCTGATGC AATGCGGCGG CTGCATACGC TTGATCCGGC TACCTGCCCA     1704
TTCGACCACC AAGCGAAACA TCGCATCGAG CGAGCACGTA CTCGGATGGA AGCCGGTCTT     1764
GTCGATCAGG ATGATCTGGA CGAAGAGCAT CAGGGGCTCG CGCCAGCCGA ACTGTTCGCC     1824
AGGCTCAAGG CGCGCATGCC CGACGGCGAG GATCTCGTCG TGACCCATGG CGATGCCTGC     1884
TTGCCGAATA TCATGGTGGA AAATGGCCGC TTTTCTGGAT TCATCGACTG TGGCCGGCTG     1944
GGTGTGGCGG ACCGCTATCA GGACATAGCG TTGGCTACCC GTGATATTGC TGAAGAGCTT     2004
GGCGGCGAAT GGGCTGACCG CTTCCTCGTG CTTTACGGTA TCGCCGCTCC CGATTCGCAG     2064
CGCATCGCCT TCTATCGCCT TCTTGACGAG TTCTTCTGAG CGGGACTCTG GGGTTCGAAA     2124
TGACCGACCA AGCGACGCCC AACCTGCCAT CACGAGATTT CGATTCCACC GCCGCCTTCT     2184
ATGAAAGGTT GGGCTTCGGA ATCGTTTTCC GGGACGCCGG CTGGATGATC CTCCAGCGCG     2244
GGGATCTCAT GCTGGAGTTC TTCGCCCACC CCGGCCGGAA ACAGGGGAAG CTGCCGGGCC     2304
CCACTGTGTC AGCCTCCTAT TCTCTGGAGT ATGGGAAGGT AAGCGAGCTG TGTGTAGAGG     2364
AAGGGCAGGG TCTTATCACG GCTACCAGTG TCTAGGAGTA AATGTGGGTG CTCAGAGAGG     2424
TTGAGACATT GGGTCAGGTT TACACCACCC AGAAACGCTC GAGCCTAGGG AGGTGGCCAC     2484
TTGTTCGCGC CTAGACTCTG TCTTACACTA CTTCCTGTCT GCAG GCT GAG CTG GAA     2540
                                                   Ala Glu Leu Glu
                                                            35
ATC CAG AAA GAT GCC TTG GAA CCC GGG CAG AGA GTG GTC ATT GTG GAT     2588
Ile Gln Lys Asp Ala Leu Glu Pro Gly Gln Arg Val Val Ile Val Asp
     40                  45                  50
GAC CTC CTG GCC ACA GGA GGTAAAGAAC CAACCCAAGA CAAACAGACT             2636
Asp Leu Leu Ala Thr Gly
 55              60
```

```
                                                      -continued

TCAAAGGGCC AGACCCTGTC CTGGGTGCTG ACTAAGCAAA GAGCTTGAAC ACCTCCTCCT      2696

TCTCTGTCCC TTCCCCCCAG GAACCATGTT TGCGGCCTGT GACCTGCTGC ACCAGCTCCG      2756

GGCTGAAGTG GTGGAGTGTG TGAGCCTGGT GGAGCTGACC TCGCTGAAGG GCAGGGAGAG      2816

GCTAGGACCT ATACCATTCT TCTCTCTCCT CCAGTATGAC TGAGGAGCTG GCTAGATGGT      2876

CACACCCCTG CTCCCAGCAG CACTAGGAAC TGCTTGGTGG CTCAGCCTAG GCGCCTAAGT      2936

GACCTTTGTG AGCTACCGGC CGCCCTTTTG TGAGTGTTAT CACTCATTCC TTTGGTCAGC      2996

TGATCCGCCG TGCCTGTGGA CCCCTGGATC CTTGTACTTT GTACACGTGC CACACACCCT      3056

GGAGCATAGC AGAGCTGTGC TACTGGAGAT CAATAAACCG TTTTGATATG CATGCCTGCT      3116

TCTCCTCAGT TTGTTGCATG GGTCACATTC CAGGCCTCCA GAGCGATACT ACAGGGACAA      3176

GGGGGCTCAG GTGGGAACCC ATAGGCTCAG CTTTGTATTG AAGCCACAAC CCCTACTAGG      3236

GAGCAGATGT TATCTCTGTC AGTCTCTGAG GCAGCTGACT ACATAAACAG GTTTATTGCT      3296

TCACTGTTCT AGGCCTGTTA TTCCATTAGG ATGGACGAGG ATGAAGCAGT GACCCACAGC      3356

CACTATATTT TTTTCTGTTG TTTGTCGAGA TGGGGTTTCT TAATATAACC AGCCCTGGCT      3416

ATTCTGGACT TGATTTGTAG CCCAGGCTGG CCTCAAACTT AAGAGGTCCA CTGCCTCTGC      3476

TTCTTGAGTG CTGGGATCAA AGTACGCACC GCAACACCCA GTTCACAGTC ACTATCTCAA      3536

AAAAGCTATT TTGTTGCAGG GCATGGTGTA TAGACCTTTA ATCCTAGTGC CTTGAAGGTA      3596

GGCAGGCTGT TAAAATTCAA GGCCAACCTG GC                                   3628

(2) INFORMATION FOR SEQ ID NO:11:

(i) SEQUENCE CHARACTERISTICS:
        (A) LENGTH: 60 amino acids
        (B) TYPE: amino acid
        (D) TOPOLOGY: linear (ii) MOLECULE TYPE: protein (xi) SEQUENCE DESCRIPTION: SEQ ID NO:11:

Ile Ser Pro Leu Leu Lys Asp Pro Asp Ser Phe Arg Ala Ser Ile Arg
  1               5                  10                  15

Leu Leu Ala Ser His Leu Lys Ser Thr His Ser Gly Lys Ile Asp Tyr
             20                  25                  30

Ile Ala Ala Glu Leu Glu Ile Gln Lys Asp Ala Leu Glu Pro Gly Gln
         35                  40                  45

Arg Val Val Ile Val Asp Asp Leu Leu Ala Thr Gly
     50                  55                  60

(2) INFORMATION FOR SEQ ID NO:12:

(i) SEQUENCE CHARACTERISTICS:
        (A) LENGTH: 3628 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(1309..1737, 1786..2100, 2716..2859)
        (D) OTHER INFORMATION: /note= "Seq Id No 12 represents the DNA
            sequence corresponding to Seq Id No 10 showing the second
            peptide coded for therein."

(xi) SEQUENCE DESCRIPTION: SEQ ID NO:12:

GCCGGCGAGG CGTTGGCGCT GTACGCTCAT CCCCCGGCGC AGGCGGTAGG CAGCCTCGGG        60
```

```
GATCTTGCGG GGCCTCTGCC CGGCCACACG CGGGTCACTC TCCTGTCCTT GTTCCTAGGG      120

ATATCTCGCC CCTCTTGAAA GACCCGGACT CCTTCCGAGC TTCCATCCGC CTCTTGGCCA      180

GTCACCTGAA GTCCACGCAC AGCGGCAAGA TCGACTACAT CGCAGGCGAG TGGCCTTGCT      240

AGGTCGTGCT CGTCCCCCAC GGTCCTAGCC CCTATCCCCT TTCCCCCTCG TGTCACCCAC      300

AGTCTGCCCC ACACCCATCC ATTCTTCTTC GACCTCTGAC ACTTCCTCCT TGGTTCCTCA      360

CTGCCTTGGA CGCTTGTTCA CCCTGGATGA ACTATGTAGG AGTCTCCCTT CCCTGCTAGG      420

TACCCTAAGG CATCTGCCCT CGGTGCTTGT TCCTAGAGAC GAACTCTGCT CTGTCCTTGT      480

GTCCAGAACC AGGCCTCCCT CTTTTAGGGC ACAAAGCTGG CCAGCATCCT GACAGCAGGC      540

TGGGAGACCC TGGAACCTCC AGATGACGGA CATCCTTGCT TAGGGGTAGC CTCTGGGATG      600

AACTAGATAC TAAAAATTAG GTAACCTTGG TTGGGCGTGG CGTGCCTGGG CAGACCTCAA      660

GCCTGGTAGC TTCAGGGGCT GTTTCTCCCC AGGACTACAC CGGGGCATCT TTCTCTTGTT      720

CCCTCACACA AGCTTGTGTT AAACAACTGC TGTCTACTTG GCTCCATGCC TGAGCTTGAG      780

AAACACCCTA GGACAGCTGA ATGTCCACCA GGAGTGTCCA GAGGGAGGGT GGGCACCCCA      840

GAGAACAGAG TGGCCTTGGT AAGTGCTCGG GGACCACAGA CTTTGCCACT TCACTTCCTA      900

TTGGTACCCT TGGCCATGCT CCAGAAATTA GGGCATGTAT GTATCCTTCC CACGACAGCT      960

AGATGCTGCA TTTGAAGGTG GCAAGACCAC CATAGGTGGC CCTGAGCTGT TCAGAAGGCA     1020

GGTAGGATCC CCAAGGCTGA GATGATGAGT TGATGGCTAC CCAGTAGCCA TCAACGTTCT     1080

TCTAACCGTA GTCAGCAAGA CCTAGTGTTC CTAGCAAGTG TTGACCTCGC CCATACTTGG     1140

CCTCTAGATT CCCATGCCCC TCAGCTCCAT CCCACAACCT TCCCTCCTTA CCCTAACAGG     1200

TCTAGACTCC AGGGGCTTCC TGTTTGGCCC TTCCCTAGCT CAGGAGCTGG GCGTGGGCTG     1260

TGTGCTCATC CGGGATCTGA TCAAGAGACA GGATGAGGAT CGTTTCGC ATG ATT GAA     1317
                                                     Met Ile Glu
                                                        1

CAA GAT GGA TTG CAC GCA GGT TCT CCG GCC GCT TGG GTG GAG AGG CTA      1365
Gln Asp Gly Leu His Ala Gly Ser Pro Ala Ala Trp Val Glu Arg Leu
     5                  10                  15

TTC GGC TAT GAC TGG GCA CAA CAG ACA ATC GGC TGC TCT GAT GCC GCC      1413
Phe Gly Tyr Asp Trp Ala Gln Gln Thr Ile Gly Cys Ser Asp Ala Ala
 20                  25                  30                  35

GTG TTC CGG CTG TCA GCG CAG GGG CGC CCG GTT CTT TTT GTC AAG ACC      1461
Val Phe Arg Leu Ser Ala Gln Gly Arg Pro Val Leu Phe Val Lys Thr
                 40                  45                  50

GAC CTG TCC GGT GCC CTG AAT GAA CTG CAG GAC GAG GCA GCG CGG CTA      1509
Asp Leu Ser Gly Ala Leu Asn Glu Leu Gln Asp Glu Ala Ala Arg Leu
             55                  60                  65

TCG TGG CTG GCC ACG ACG GGC GTT CCT TGC GCA GCT GTG CTC GAC GTT      1557
Ser Trp Leu Ala Thr Thr Gly Val Pro Cys Ala Ala Val Leu Asp Val
         70                  75                  80

GTC ACT GAA GCG GGA AGG GAC TGG CTG CTA TTG GGC GAA GTG CCG GGG      1605
Val Thr Glu Ala Gly Arg Asp Trp Leu Leu Leu Gly Glu Val Pro Gly
     85                  90                  95

CAG GAT CTC CTG TCA TCT CAC CTT GCT CCT GCC GAG AAA GTA TCC ATC      1653
Gln Asp Leu Leu Ser Ser His Leu Ala Pro Ala Glu Lys Val Ser Ile
100                 105                 110                 115

ATG GCT GAT GCA ATG CGG CGG CTG CAT ACG CTT GAT CCG GCT ACC TGC      1701
Met Ala Asp Ala Met Arg Arg Leu His Thr Leu Asp Pro Ala Thr Cys
                120                 125                 130

CCA TTC GAC CAC CAA GCG AAA CAT CGC ATC GAG CGA GCACGTACTC           1747
Pro Phe Asp His Gln Ala Lys His Arg Ile Glu Arg
```

-continued

```
                  135                 140
GGATGGAAGC CGGTCTTGTC GATCAGGATG ATCTGGAC GAA GAG CAT CAG GGG           1800
                                          Glu Glu His Gln Gly
                                                          145

CTC GCG CCA GCC GAA CTG TTC GCC AGG CTC AAG GCG CGC ATG CCC GAC        1848
Leu Ala Pro Ala Glu Leu Phe Ala Arg Leu Lys Ala Arg Met Pro Asp
    150                 155                 160

GGC GAG GAT CTC GTC GTG ACC CAT GGC GAT GCC TGC TTG CCG AAT ATC        1896
Gly Glu Asp Leu Val Val Thr His Gly Asp Ala Cys Leu Pro Asn Ile
165                 170                 175                 180

ATG GTG GAA AAT GGC CGC TTT TCT GGA TTC ATC GAC TGT GGC CGG CTG        1944
Met Val Glu Asn Gly Arg Phe Ser Gly Phe Ile Asp Cys Gly Arg Leu
                185                 190                 195

GGT GTG GCG GAC CGC TAT CAG GAC ATA GCG TTG GCT ACC CGT GAT ATT        1992
Gly Val Ala Asp Arg Tyr Gln Asp Ile Ala Leu Ala Thr Arg Asp Ile
            200                 205                 210

GCT GAA GAG CTT GGC GGC GAA TGG GCT GAC CGC TTC CTC GTG CTT TAC        2040
Ala Glu Glu Leu Gly Gly Glu Trp Ala Asp Arg Phe Leu Val Leu Tyr
        215                 220                 225

GGT ATC GCC GCT CCC GAT TCG CAG CGC ATC GCC TTC TAT CGC CTT CTT        2088
Gly Ile Ala Ala Pro Asp Ser Gln Arg Ile Ala Phe Tyr Arg Leu Leu
    230                 235                 240

GAC GAG TTC TTC TGAGCGGGAC TCTGGGGTTC GAAATGACCG ACCAAGCGAC            2140
Asp Glu Phe Phe
245

GCCCAACCTG CCATCACGAG ATTTCGATTC CACCGCCGCC TTCTATGAAA GGTTGGGCTT      2200

CGGAATCGTT TTCCGGGACG CCGGCTGGAT GATCCTCCAG CGCGGGGATC TCATGCTGGA      2260

GTTCTTCGCC CACCCCGGCC GGAAACAGGG GAAGCTGCCG GGCCCCACTG TGTCAGCCTC      2320

CTATTCTCTG GAGTATGGGA AGGTAAGCGA GCTGTGTGTA GAGGAAGGGC AGGGTCTTAT      2380

CACGGCTACC AGTGTCTAGG AGTAAATGTG GGTGCTCAGA GAGGTTGAGA CATTGGGTCA      2440

GGTTTACACC ACCCAGAAAC GCTCGAGCCT AGGGAGGTGG CCACTTGTTC GCGCCTAGAC      2500

TCTGTCTTAC ACTACTTCCT GTCTGCAGGC TGAGCTGGAA ATCCAGAAAG ATGCCTTGGA      2560

ACCCGGGCAG AGAGTGGTCA TTGTGGATGA CCTCCTGGCC ACAGGAGGTA AGAACCAAC       2620

CCAAGACAAA CAGACTTCAA AGGGCCAGAC CCTGTCCTGG GTGCTGACTA AGCAAAGAGC      2680

TTGAACACCT CCTCCTTCTC TGTCCCTTCC CCCA GGA ACC ATG TTT GCG GCC          2733
                                    Gly Thr Met Phe Ala Ala
                                                250

TGT GAC CTG CTG CAC CAG CTC CGG GCT GAA GTG GTG GAG TGT GTG AGC        2781
Cys Asp Leu Leu His Gln Leu Arg Ala Glu Val Val Glu Cys Val Ser
255                 260                 265                 270

CTG GTG GAG CTG ACC TCG CTG AAG GGC AGG GAG AGG CTA GGA CCT ATA        2829
Leu Val Glu Leu Thr Ser Leu Lys Gly Arg Glu Arg Leu Gly Pro Ile
                275                 280                 285

CCA TTC TTC TCT CTC CTC CAG TAT GAC TGAGGAGCTG GCTAGATGGT              2876
Pro Phe Phe Ser Leu Leu Gln Tyr Asp
            290                 295

CACACCCCTG CTCCCAGCAG CACTAGGAAC TGCTTGGTGG CTCAGCCTAG GCGCCTAAGT      2936

GACCTTTGTG AGCTACCGGC CGCCCTTTTG TGAGTGTTAT CACTCATTCC TTTGGTCAGC      2996

TGATCCGCCG TGCCTGTGGA CCCCTGGATC CTTGTACTTT GTACACGTGC CACACACCCT      3056

GGAGCATAGC AGAGCTGTGC TACTGGAGAT CAATAAACCG TTTTGATATG CATGCCTGCT      3116

TCTCCTCAGT TTGTTGCATG GGTCACATTC CAGGCCTCCA GAGCGATACT ACAGGGACAA      3176

GGGGGCTCAG GTGGGAACCC ATAGGCTCAG CTTTGTATTG AAGCCACAAC CCCTACTAGG      3236
```

-continued

```
GAGCAGATGT TATCTCTGTC AGTCTCTGAG GCAGCTGACT ACATAAACAG GTTTATTGCT      3296

TCACTGTTCT AGGCCTGTTA TTCCATTAGG ATGGACGAGG ATGAAGCAGT GACCCACAGC      3356

CACTATATTT TTTTCTGTTG TTTGTCGAGA TGGGGTTTCT TAATATAACC AGCCCTGGCT      3416

ATTCTGGACT TGATTTGTAG CCCAGGCTGG CCTCAAACTT AAGAGGTCCA CTGCCTCTGC      3476

TTCTTGAGTG CTGGGATCAA AGTACGCACC GCAACACCCA GTTCACAGTC ACTATCTCAA      3536

AAAAGCTATT TTGTTGCAGG GCATGGTGTA TAGACCTTTA ATCCTAGTGC CTTGAAGGTA      3596

GGCAGGCTGT TAAAATTCAA GGCCAACCTG GC                                    3628
```

(2) INFORMATION FOR SEQ ID NO:13:

(i) SEQUENCE CHARACTERISTICS:
        (A) LENGTH: 295 amino acids
        (B) TYPE: amino acid
        (D) TOPOLOGY: linear (ii) MOLECULE TYPE: protein (xi) SEQUENCE DESCRIPTION: SEQ ID NO:13:

```
Met Ile Glu Gln Asp Gly Leu His Ala Gly Ser Pro Ala Ala Trp Val
 1               5                  10                  15

Glu Arg Leu Phe Gly Tyr Asp Trp Ala Gln Gln Thr Ile Gly Cys Ser
                20                  25                  30

Asp Ala Ala Val Phe Arg Leu Ser Ala Gln Gly Arg Pro Val Leu Phe
            35                  40                  45

Val Lys Thr Asp Leu Ser Gly Ala Leu Asn Glu Leu Gln Asp Glu Ala
        50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
               100                 105                 110

Val Ser Ile Met Ala Asp Ala Met Arg Arg Leu His Thr Leu Asp Pro
           115                 120                 125

Ala Thr Cys Pro Phe Asp His Gln Ala Lys His Arg Ile Glu Arg Glu
       130                 135                 140

Glu His Gln Gly Leu Ala Pro Ala Glu Leu Phe Ala Arg Leu Lys Ala
145                 150                 155                 160

Arg Met Pro Asp Gly Glu Asp Leu Val Val Thr His Gly Asp Ala Cys
               165                 170                 175

Leu Pro Asn Ile Met Val Glu Asn Gly Arg Phe Ser Gly Phe Ile Asp
           180                 185                 190

Cys Gly Arg Leu Gly Val Ala Asp Arg Tyr Gln Asp Ile Ala Leu Ala
       195                 200                 205

Thr Arg Asp Ile Ala Glu Glu Leu Gly Gly Glu Trp Ala Asp Arg Phe
   210                 215                 220

Leu Val Leu Tyr Gly Ile Ala Ala Pro Asp Ser Gln Arg Ile Ala Phe
225                 230                 235                 240

Tyr Arg Leu Leu Asp Glu Phe Phe Gly Thr Met Phe Ala Ala Cys Asp
               245                 250                 255

Leu Leu His Gln Leu Arg Ala Glu Val Val Glu Cys Val Ser Leu Val
           260                 265                 270

Glu Leu Thr Ser Leu Lys Gly Arg Glu Arg Leu Gly Pro Ile Pro Phe
```

```
                275                 280                 285
Phe Ser Leu Leu Gln Tyr Asp
        290                 295

(2) INFORMATION FOR SEQ ID NO:14:

(i) SEQUENCE CHARACTERISTICS:
        (A) LENGTH: 3628 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(1199..1309, 1738..1785)
        (D) OTHER INFORMATION: /note= "Seq Id No 14 represents the DNA
            sequence corresponding to Seq Id No 10 showing the third
            peptide coded for therein."

(xi) SEQUENCE DESCRIPTION: SEQ ID NO:14:

GCCGGCGAGG CGTTGGCGCT GTACGCTCAT CCCCCGGCGC AGGCGGTAGG CAGCCTCGGG      60

GATCTTGCGG GGCCTCTGCC CGGCCACACG CGGGTCACTC TCCTGTCCTT GTTCCTAGGG     120

ATATCTCGCC CCTCTTGAAA GACCCGGACT CCTTCCGAGC TTCCATCCGC CTCTTGGCCA     180

GTCACCTGAA GTCCACGCAC AGCGGCAAGA TCGACTACAT CGCAGGCGAG TGGCCTTGCT     240

AGGTCGTGCT CGTCCCCCAC GGTCCTAGCC CCTATCCCCT TTCCCCCTCG TGTCACCCAC     300

AGTCTGCCCC ACACCCATCC ATTCTTCTTC GACCTCTGAC ACTTCCTCCT TGGTTCCTCA     360

CTGCCTTGGA CGCTTGTTCA CCCTGGATGA ACTATGTAGG AGTCTCCCTT CCCTGCTAGG     420

TACCCTAAGG CATCTGCCCT CGGTGCTTGT TCCTAGAGAC GAACTCTGCT CTGTCCTTGT     480

GTCCAGAACC AGGCCTCCCT CTTTTAGGGC ACAAAGCTGG CCAGCATCCT GACAGCAGGC     540

TGGGAGACCC TGGAACCTCC AGATGACGGA CATCCTTGCT TAGGGGTAGC CTCTGGGATG     600

AACTAGATAC TAAAAATTAG GTAACCTTGG TTGGGCGTGG CGTGCCTGGG CAGACCTCAA     660

GCCTGGTAGC TTCAGGGGCT GTTTCTCCCC AGGACTACAC CGGGGCATCT TTCTCTTGTT     720

CCCTCACACA AGCTTGTGTT AAACAACTGC TGTCTACTTG GCTCCATGCC TGAGCTTGAG     780

AAACACCCTA GGACAGCTGA ATGTCCACCA GGAGTGTCCA GAGGGAGGGT GGGCACCCCA     840

GAGAACAGAG TGGCCTTGGT AAGTGCTCGG GGACCACAGA CTTTGCCACT TCACTTCCTA     900

TTGGTACCCT TGGCCATGCT CCAGAAATTA GGGCATGTAT GTATCCTTCC CACGCACAGCT    960

AGATGCTGCA TTTGAAGGTG GCAAGACCAC CATAGGTGGC CCTGAGCTGT TCAGAAGGCA    1020

GGTAGGATCC CCAAGGCTGA GATGATGAGT TGATGGCTAC CCAGTAGCCA TCAACGTTCT    1080

TCTAACCGTA GTCAGCAAGA CCTAGTGTTC CTAGCAAGTG TTGACCTCGC CCATACTTGG    1140

CCTCTAGATT CCCATGCCCC TCAGCTCCAT CCCACAACCT TCCCTCCTTA CCCTAACA     1198

GGT CTA GAC TCC AGG GGC TTC CTG TTT GGC CCT TCC CTA GCT CAG GAG      1246
Gly Leu Asp Ser Arg Gly Phe Leu Phe Gly Pro Ser Leu Ala Gln Glu
  1               5                  10                  15

CTG GGC GTG GGC TGT GTG CTC ATC CGG GAT CTG ATC AAG AGA CAG GAT      1294
Leu Gly Val Gly Cys Val Leu Ile Arg Asp Leu Ile Lys Arg Gln Asp
             20                  25                  30

GAG GAT CGT TTC GCA TGATTGAACA AGATGGATTG CACGCAGGTT CTCCGGCCGC      1349
Glu Asp Arg Phe Ala
        35

TTGGGTGGAG AGGCTATTCG GCTATGACTG GGCACAACAG ACAATCGGCT GCTCTGATGC    1409
```

-continued

```
CGCCGTGTTC CGGCTGTCAG CGCAGGGGCG CCCGGTTCTT TTTGTCAAGA CCGACCTGTC      1469

CGGTGCCCTG AATGAACTGC AGGACGAGGC AGCGCGGCTA TCGTGGCTGG CCACGACGGG      1529

CGTTCCTTGC GCAGCTGTGC TCGACGTTGT CACTGAAGCG GGAAGGGACT GGCTGCTATT      1589

GGGCGAAGTG CCGGGGCAGG ATCTCCTGTC ATCTCACCTT GCTCCTGCCG AGAAAGTATC      1649

CATCATGGCT GATGCAATGC GGCGGCTGCA TACGCTTGAT CCGGCTACCT GCCCATTCGA      1709

CCACCAAGCG AAACATCGCA TCGAGCGA GCA CGT ACT CGG ATG GAA GCC GGT         1761
                                Ala Arg Thr Arg Met Glu Ala Gly
                                 40                          45

CTT GTC GAT CAG GAT GAT CTG GAC GAAGAGCATC AGGGGCTCGC GCCAGCCGAA       1815
Leu Val Asp Gln Asp Asp Leu Asp
              50

CTGTTCGCCA GGCTCAAGGC GCGCATGCCC GACGGCGAGG ATCTCGTCGT GACCCATGGC      1875

GATGCCTGCT TGCCGAATAT CATGGTGGAA AATGGCCGCT TTTCTGGATT CATCGACTGT      1935

GGCCGGCTGG GTGTGGCGGA CCGCTATCAG GACATAGCGT TGGCTACCCG TGATATTGCT      1995

GAAGAGCTTG GCGGCGAATG GGCTGACCGC TTCCTCGTGC TTTACGGTAT CGCCGCTCCC      2055

GATTCGCAGC GCATCGCCTT CTATCGCCTT CTTGACGAGT TCTTCTGAGC GGGACTCTGG      2115

GGTTCGAAAT GACCGACCAA GCGACGCCCA ACCTGCCATC ACGAGATTTC GATTCCACCG      2175

CCGCCTTCTA TGAAAGGTTG GCTTCGGAA TCGTTTTCCG GGACGCCGGC TGGATGATCC       2235

TCCAGCGCGG GGATCTCATG CTGGAGTTCT TCGCCCACCC CGGCCGGAAA CAGGGGAAGC      2295

TGCCGGGCCC CACTGTGTCA GCCTCCTATT CTCTGGAGTA TGGGAAGGTA AGCGAGCTGT      2355

GTGTAGAGGA AGGGCAGGGT CTTATCACGG CTACCAGTGT CTAGGAGTAA ATGTGGGTGC      2415

TCAGAGAGGT TGAGACATTG GGTCAGGTTT ACACCACCCA GAAACGCTCG AGCCTAGGGA      2475

GGTGGCCACT TGTTCGCGCC TAGACTCTGT CTTACACTAC TTCCTGTCTG CAGGCTGAGC      2535

TGGAAATCCA GAAAGATGCC TTGGAACCCG GGCAGAGAGT GGTCATTGTG GATGACCTCC      2595

TGGCCACAGG AGGTAAAGAA CCAACCCAAG ACAAACAGAC TTCAAAGGGC CAGACCCTGT      2655

CCTGGGTGCT GACTAAGCAA AGAGCTTGAA CACCTCCTCC TTCTCTGTCC CTTCCCCCCA      2715

GGAACCATGT TTGCGGCCTG TGACCTGCTG CACCAGCTCC GGGCTGAAGT GGTGGAGTGT      2775

GTGAGCCTGG TGGAGCTGAC CTCGCTGAAG GGCAGGGAGA GGCTAGGACC TATACCATTC      2835

TTCTCTCTCC TCCAGTATGA CTGAGGAGCT GGCTAGATGG TCACACCCCT GCTCCCAGCA      2895

GCACTAGGAA CTGCTTGGTG GCTCAGCCTA GGCGCCTAAG TGACCTTTGT GAGCTACCGG      2955

CCGCCCTTTT GTGAGTGTTA TCACTCATTC CTTTGGTCAG CTGATCCGCC GTGCCTGTGG      3015

ACCCCTGGAT CCTTGTACTT TGTACACGTG CCACACACCC TGGAGCATAG CAGAGCTGTG      3075

CTACTGGAGA TCAATAAACC GTTTTGATAT GCATGCCTGC TTCTCCTCAG TTTGTTGCAT      3135

GGGTCACATT CCAGGCCTCC AGAGCGATAC TACAGGGACA AGGGGCTCA GGTGGGAACC       3195

CATAGGCTCA GCTTTGTATT GAAGCCACAA CCCCTACTAG GGAGCAGATG TTATCTCTGT      3255

CAGTCTCTGA GGCAGCTGAC TACATAAACA GGTTTATTGC TTCACTGTTC TAGGCCTGTT      3315

ATTCCATTAG GATGGACGAG GATGAAGCAG TGACCCACAG CCACTATATT TTTTTCTGTT      3375

GTTTGTCGAG ATGGGGTTTC TTAATATAAC CAGCCCTGGC TATTCTGGAC TTGATTTGTA      3435

GCCCAGGCTG GCCTCAAACT TAAGAGGTCC ACTGCCTCTG CTTCTTGAGT GCTGGGATCA      3495

AAGTACGCAC CGCAACACCC AGTTCACAGT CACTATCTCA AAAAAGCTAT TTGTTGCAG       3555

GGCATGGTGT ATAGACCTTT AATCCTAGTG CCTTGAAGGT AGGCAGGCTG TTAAAATTCA      3615

AGGCCAACCT GGC                                                        3628
```

(2) INFORMATION FOR SEQ ID NO:15:

(i) SEQUENCE CHARACTERISTICS:
        (A) LENGTH: 53 amino acids
        (B) TYPE: amino acid
        (D) TOPOLOGY: linear (ii) MOLECULE TYPE: protein (xi) SEQUENCE DESCRIPTION: SEQ ID NO:15:

```
Gly Leu Asp Ser Arg Gly Phe Leu Phe Gly Pro Ser Leu Ala Gln Glu
 1               5                  10                  15

Leu Gly Val Gly Cys Val Leu Ile Arg Asp Leu Ile Lys Arg Gln Asp
            20                  25                  30

Glu Asp Arg Phe Ala Ala Arg Thr Arg Met Glu Ala Gly Leu Val Asp
        35                  40                  45

Gln Asp Asp Leu Asp
    50
```

(2) INFORMATION FOR SEQ ID NO:16:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..9
        (D) OTHER INFORMATION: /note= "This sesequence represents mutation of base 2487 of Seq Id No 3"

(xi) SEQUENCE DESCRIPTION: SEQ ID NO:16:

CTGCAAGCT                                                               9

(2) INFORMATION FOR SEQ ID NO:17:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..9
        (D) OTHER INFORMATION: /note= "This sequence represents mutation of base 2487 of Seq Id No 3"

(xi) SEQUENCE DESCRIPTION: SEQ ID NO:17:

CTGCGGGCT                                                               9

(2) INFORMATION FOR SEQ ID NO:18:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (genomic)

(ix) FEATURE:

-continued

```
        (A) NAME/KEY: misc_feature
        (B) LOCATION: 1..9
        (D) OTHER INFORMATION: /note= "This sequence represents
            mutation of base 2487 of Seq Id No 3"

(xi) SEQUENCE DESCRIPTION: SEQ ID NO:18:

CTGCATGCT                                                             9

(2) INFORMATION FOR SEQ ID NO:19:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..9
        (D) OTHER INFORMATION: /note= "This sequence represents
            mutation of base 2487 of Seq Id No 3"

(xi) SEQUENCE DESCRIPTION: SEQ ID NO:19:

CTGCACGCT                                                             9

(2) INFORMATION FOR SEQ ID NO:20:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..9
        (D) OTHER INFORMATION: /note= "This sequence represents
            mutation of base 2486 of Seq Id No 3"

(xi) SEQUENCE DESCRIPTION: SEQ ID NO:20:

CTGCCGGCT                                                             9

(2) INFORMATION FOR SEQ ID NO:21:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..9
        (D) OTHER INFORMATION: /note= "This sequence represents
            mutation of base 2486 of Seq Id No 3"

(xi) SEQUENCE DESCRIPTION: SEQ ID NO:21:

CTGCTGGCT                                                             9
```